(12) United States Patent
Dimov et al.

(10) Patent No.: US 10,300,090 B2
(45) Date of Patent: May 28, 2019

(54) COMPOSITIONS OF HEMATOPOIETIC STEM CELL TRANSPLANTS

(71) Applicant: Orca Biosystems, Inc., Menlo Park, CA (US)

(72) Inventors: Ivan K. Dimov, Menlo Park, CA (US); Nathaniel Fernhoff, Menlo Park, CA (US); Kevin Sheehan, Menlo Park, CA (US)

(73) Assignee: Orca Biosystems, Inc., Menlo Park, CA (US)

( * ) Notice: Subject to any disclaimer, the term of this patent is extended or adjusted under 35 U.S.C. 154(b) by 0 days.

(21) Appl. No.: 15/922,709

(22) Filed: Mar. 15, 2018

(65) Prior Publication Data
US 2018/0264039 A1    Sep. 20, 2018

Related U.S. Application Data

(60) Provisional application No. 62/471,769, filed on Mar. 15, 2017.

(51) Int. Cl.
| | |
|---|---|
| *A61K 35/17* | (2015.01) |
| *A61P 3/00* | (2006.01) |
| *A61P 37/02* | (2006.01) |
| *A61P 7/06* | (2006.01) |
| *A61P 21/00* | (2006.01) |
| *A61P 35/02* | (2006.01) |
| *C12N 5/0783* | (2010.01) |
| *C12N 5/0789* | (2010.01) |

(52) U.S. Cl.
CPC .............. *A61K 35/17* (2013.01); *A61P 3/00* (2018.01); *A61P 7/06* (2018.01); *A61P 21/00* (2018.01); *A61P 35/02* (2018.01); *A61P 37/02* (2018.01); *C12N 5/0636* (2013.01); *C12N 5/0637* (2013.01); *C12N 5/0638* (2013.01); *C12N 5/0646* (2013.01); *C12N 5/0647* (2013.01)

(58) Field of Classification Search
CPC ............ C07K 16/2878; C07K 16/2833; C07K 16/2866; C07K 16/2887; C07K 2317/76; C07K 2319/30; C07K 16/28; A61K 35/12; A61K 35/26; A61K 35/39; A61K 39/395; A61K 45/06; A61K 2300/00; A61K 35/28; A61K 31/436; A61K 31/675; A61K 35/44; A61K 35/50; A61K 38/1825; A61K 2035/124; A61K 35/15; A61K 2035/122; A61K 38/217; A61K 8/982; A61K 38/18; A61K 38/185; A61K 38/1866; A61K 38/19; A61K 38/22; A61K 38/55; A61K 39/001; A61K 2039/5154; A61K 35/51; A61K 35/17; A01K 2217/15; A01K 2227/108; A01K 2267/025; A01K 67/0275; A01K 2217/052; A01K 2217/075; A01K 2217/206; A01K 2227/105; A01K 2267/0362; A01K 67/0276; A01K 67/0278; C12N 15/113; C12N 2310/10; C12N 2310/20; C12N 5/0676; C12N 5/0677; C12N 15/8509; C12N 2502/02; C12N 2830/40; C12N 5/0018; C12N 9/1051; C12N 2501/22; C12N 5/0636; C12N 5/0647; C12N 2501/23; C12N 2501/24; C12N 2501/25; C12N 2501/26; C12N 2502/11; C12N 5/0634; C12N 5/0645; C12N 5/0648; C12N 5/0087; C12N 5/0637; C12N 5/0638; C12N 5/064; C12N 5/0646; C12Y 204/01087; Y02A 50/414; A61F 2/022; A61M 2202/097; A61M 5/14244; A61M 5/14276; A61M 5/1452; A61Q 19/08; A61Q 7/00; A61P 21/00; A61P 35/02; A61P 37/02; A61P 3/00; A61P 7/06
See application file for complete search history.

(56) References Cited

U.S. PATENT DOCUMENTS

| | | |
|---|---|---|
| 5,514,340 A | 5/1996 | Lansdorp et al. |
| 5,858,358 A | 1/1999 | June et al. |

(Continued)

FOREIGN PATENT DOCUMENTS

| | | |
|---|---|---|
| EP | 1185867 B1 | 3/2005 |
| EP | 2352816 B1 | 6/2015 |

(Continued)

OTHER PUBLICATIONS

Bleakley et al., "Engineering Human Peripheral Blood Stem Cell Grafts that Are Depleted of Naïve T Cells and Retain Functional Pathogen-Specific Memory T Cells," *Biol Blood Marrow Transplant* 20:705-716, 2014.
Bleakley et al., "Outcomes of acute leukemia patients transplanted with naive T cell—depleted stem cell grafts," *The Journal of Clinical Investigation* 125(7):2677-2689, 2015.
Chaidos et al., "Graft invariant natural killer T-cell dose predicts risk of acute graft-versus-host disease in allogeneic hematopoietic stem cell transplantation," *Blood* 119(21):5030-5036, 2012. (8 pages).
Chen et al., "High-throughput analysis and protein engineering using microcapillary arrays," *Nature Chemical Biology* 12:76-81, 2016. (9 pages).

(Continued)

*Primary Examiner* — Deborah K Ware
(74) *Attorney, Agent, or Firm* — Wilson Sonsini Goodrich & Rosati

(57) ABSTRACT

The present disclosure provides distinct therapeutic populations of cells that form a pharmaceutical composition useful in hematopoietic stem/progenitor cell transplant. For example, the present disclosure provides a therapeutic population of cells, comprising an enriched population of hematopoietic stem/progenitor cells, memory T cells, regulatory T cells, and wherein the population of cells is depleted of naïve conventional αβ-T cells. The present disclosure further provides methods of treatment using the therapeutic population of cells. In other embodiments, the present disclosure provides methods of producing a therapeutic population of cells.

24 Claims, 26 Drawing Sheets

(56) References Cited

U.S. PATENT DOCUMENTS

| | | | |
|---|---|---|---|
| 5,928,639 | A | 7/1999 | Slavin |
| 6,537,807 | B1 | 3/2003 | Smith et al. |
| 6,544,506 | B2 | 4/2003 | Reisner |
| 7,651,855 | B2 | 1/2010 | Blazar et al. |
| 8,277,811 | B2 | 10/2012 | Zeng |
| 8,632,768 | B2 | 1/2014 | Ildstad et al. |
| 8,926,964 | B2 | 1/2015 | Hariri et al. |
| 8,951,793 | B2 | 2/2015 | Tran et al. |
| 9,156,912 | B2 | 10/2015 | Matsushima et al. |
| 9,452,184 | B2 | 9/2016 | Ildstad et al. |
| 9,523,076 | B2 | 12/2016 | Schoenbrunn et al. |
| 9,738,872 | B2 | 8/2017 | Reisner et al. |
| 9,795,604 | B2 | 10/2017 | Byrd et al. |
| 9,896,659 | B2 | 2/2018 | Perry et al. |
| 2002/0127208 | A1 | 9/2002 | Waller et al. |
| 2003/0147865 | A1 | 8/2003 | Salomon et al. |
| 2003/0223998 | A1 | 12/2003 | Lamb, Jr. et al. |
| 2004/0137617 | A1 | 7/2004 | Luxembourg et al. |
| 2004/0228845 | A1 | 11/2004 | Ildstad |
| 2005/0118142 | A1 | 6/2005 | Ildstad |
| 2005/0214265 | A1 | 9/2005 | Iidstad |
| 2006/0018885 | A1 | 1/2006 | Ildstad |
| 2006/0222633 | A1 | 10/2006 | Shlomchik et al. |
| 2007/0237752 | A1 | 10/2007 | Christensen et al. |
| 2008/0032401 | A1 | 2/2008 | Edinger et al. |
| 2008/0038231 | A1 | 2/2008 | Rodgerson et al. |
| 2008/0095749 | A1 | 4/2008 | Aggarwal et al. |
| 2008/0292601 | A1 | 11/2008 | Song |
| 2009/0130067 | A1 | 5/2009 | Buscher et al. |
| 2009/0297471 | A1 | 12/2009 | Markovic et al. |
| 2010/0111905 | A1 | 5/2010 | Balber |
| 2011/0059050 | A1 | 3/2011 | Cetrulo et al. |
| 2011/0110909 | A1 | 5/2011 | Ildstad et al. |
| 2011/0298883 | A1 | 12/2011 | Ohyama |
| 2012/0177621 | A1 | 7/2012 | Strober et al. |
| 2012/0269774 | A1* | 10/2012 | Ichim ............... A61K 35/28 424/93.7 |
| 2014/0011690 | A1 | 1/2014 | Dimov et al. |
| 2014/0212398 | A1 | 7/2014 | Reisner et al. |
| 2014/0308250 | A1 | 10/2014 | Handgretinger et al. |
| 2014/0369974 | A1 | 12/2014 | Reisner et al. |
| 2016/0040123 | A1 | 2/2016 | Kanemura et al. |
| 2016/0166613 | A1 | 6/2016 | Spencer et al. |
| 2016/0175358 | A1 | 6/2016 | Jakobovits et al. |
| 2016/0184367 | A1 | 6/2016 | Sackstein |
| 2016/0185861 | A1 | 6/2016 | Bedoya et al. |
| 2016/0245805 | A1 | 8/2016 | Baer et al. |
| 2016/0279171 | A1 | 9/2016 | Gurney et al. |
| 2017/0121684 | A1 | 5/2017 | Zuniga-Pflucker et al. |
| 2017/0216417 | A1 | 8/2017 | Cohen et al. |
| 2017/0246277 | A1 | 8/2017 | Schneck et al. |
| 2017/0296588 | A1 | 10/2017 | Ichim et al. |
| 2018/0153145 | A1 | 6/2018 | Gilson et al. |
| 2018/0161370 | A1 | 6/2018 | Faustman |

FOREIGN PATENT DOCUMENTS

| | | |
|---|---|---|
| EP | 2606120 B1 | 10/2015 |
| EP | 3037522 A1 | 6/2016 |
| EP | 3097917 A1 | 11/2016 |
| EP | 2558857 B1 | 9/2017 |
| WO | WO-2004018996 A2 | 3/2004 |
| WO | WO-2014015312 A1 | 1/2014 |
| WO | WO-2015127190 A1 | 8/2015 |
| WO | WO-2016133907 A1 | 8/2016 |
| WO | WO-2017023753 A1 | 2/2017 |
| WO | WO-2017035375 A1 | 3/2017 |
| WO | WO-2017042170 A1 | 3/2017 |
| WO | WO-2017048809 A1 | 3/2017 |
| WO | WO-2017078807 A1 | 5/2017 |
| WO | WO-2017094008 A1 | 6/2017 |
| WO | WO-2017096347 A1 | 6/2017 |
| WO | WO-2017127755 A1 | 7/2017 |
| WO | WO-2017132446 A1 | 8/2017 |
| WO | WO-2017156365 A1 | 9/2017 |
| WO | WO-2018013993 A1 | 1/2018 |
| WO | 2018/053485 A4 | 3/2018 |
| WO | WO-2018170335 A1 | 9/2018 |

OTHER PUBLICATIONS

Cozzo et al., "Cutting Edge: Self-Peptides Drive the Peripheral Expansion of CD4$^+$CD25$^+$ Regulatory T Cells," *The Journal of Immunology* 171:5678-5682, 2003. (6 pages).

Exley et al., "Adoptive Transfer of Invariant NKT Cells as Immunotherapy for Advanced Melanoma: a Phase 1 Clinical Trial," American Association for Cancer Research, downloaded from http://clincancerres.aacrjournals.org on Mar. 9, 2018, 27 pages.

Hoffmann et al., "Donor-type CD4$^+$CD25$^+$ Regulatory T Cells Suppress Lethal Acute Graft-Versus-Host Disease after Allogeneic Bone Marrow Transplantation," *Journal of Experimental Medicine* 196(3):389-399, 2002.

Ianni et al., "Immunoselection and clinical use of T regulatory cells in HLA-haploidentical stem cell transplantation," *Best Practice & Research Clinical Haematology* 24:459-466, 2011.

Ianni et al., "Tregs prevent GVHD and promote immune reconstitution in HLA-haploidentical transplantation," *Blood* 117(14):3921-3928, 2011. (9 pages.).

Liu et al., "CD127 expression inversely correlates with FoxP3 and suppressive function of human CD4$^+$ T reg cells," *The Journal of Experimental Medicine* 203(7): 1701-1711, 2006.

Magenau et al., "Frequency of CD4$^+$CD25$^{hi}$FOXP3$^+$Regulatory T Cells Has Diagnostic and Prognostic Value as a Biomarker for Acute Graft-versus-Host-Disease," *Biol Blood Marrow Transplant* 16:907-914, 2010.

Martelli et al., "HLA-haploidentical transplantation with regulatory and conventional T-cell adoptive immunotherapy prevents acute leukemia relapse," *Blood* 124(4):638-644, 2014. (8 pages).

Montoya et al., "Characterization of human invariant natural killer T subsets in health and disease using a novel invariant natural killer T cell-clonotypic monoclonal antibody, 6B11," *Immunology* 122:1-14, 2007.

Orca Biosystems, Inc., "Methods and Apparatuses for Sorting Target Particles," International Application No. PCT/US2017/061414, filed Nov. 13, 2017, corresponds to U.S. Appl. No. 62/421,979, 146 pages.

Patel et al. "Clinical grade isolation of regulatory T cells from G-CSF mobilized peripheral blood improves with initial depletion of monocytes," *Am J Blood Res* 5(2): 79-85, 2015.

Peters et al., "Clinical Grade Treg: GMP Isolation, Improvement of Purity by CD127$^{pos}$ Depletion, Treg Expansion, and Treg Cryopreservation," *PLoS One* 3(9):e3161, 2008. (10 pages).

Restifo, "Big bang theory of stem-like T cells confirmed," *Blood* 124(4):476-477, 2014. (3 pages).

Rowe et al., "Engineering Hematopoietic Stem Cells: Lessons from Development," *Cell Stem Cell* 18:707-720, 2016.

Schneidawind et al., "CD4$^+$ invariant natural killer T cells protect from murine GVHD lethality through expansion of donor CD4$^+$CD25$^+$FoxP3$^+$ regulatory T cells," *Blood* 124(22):3320-3328, 2014. (10 pages).

Schneidawind et al., "Third-party CD4$^+$ invariant natural killer T cells protect from murine GVHD lethality," *Blood* 125(22):3491-3500, 2015. (11 pages).

Seddiki et al., "Expression of interleukin (IL)-2 and IL-7 receptors discriminates between human regulatory and activated T cells," *The Journal of Experimental Medicine* 203(7): 1693-1700, 2006.

Taylor et al., "The infusion of ex vivo activated and expanded CD4$^+$CD25$^+$ immune regulatory cells inhibits graft-versus-host disease lethality," *Blood* 99(10):3493-3499, 2002. (8 pages.).

Tran et al., "Optimized Processing of Growth Factor Mobilized Peripheral Blood CD34+ Products by Counterflow Centrifugal Elutriation," *Stem Cells Translational Medicine* 1:422-429, 2012.

Triplett et al., "Rapid memory T-cell reconstitution recapitulating CD45RA-depleted haploidentical transplant graft content in patients with hematologic malignancies" *Bone Marrow Transplantation* 50:968-977, 2015.

(56) References Cited

OTHER PUBLICATIONS

Xiong, "Immuno-Magnetic T Cell Depletion for Allogeneic Hematological Stem Cell Transplantation," doctoral dissertation, The Ohio State University, 2008, 253 pages.

Ayello, et al. Familial Haploidentical (FHI) Allogeneic Stem Cell Transplantation (AlloSCT) Utilizing CD34 Enrichment and PB MNC Addback in Children and Adolescents with High Risk Sickle Cell Disease (SCD): Rapid Engraftment, Immune Cell Reconstitution, and Sustained Donor Chimerism (IND 14359). Blood 2016 128:1245.

Keever-Taylor, et al. Characteristics of CliniMACS® System CD34-Enriched T Cell-Depleted Grafts in a Multi-Center Trial for Acute Myeloid Leukemia-Blood and Marrow Transplant Clinical Trials Network (BMT CTN) Protocol 0303. Biol Blood Marrow Transplant. May 2012; 18(5): 690-697.

PCTUS2018/022755 International Search Report and Written Opinion dated Jun. 26, 2018.

Schaap, et al. A randomized trial comparing CD34 enriched grafts versus CD3/CD19 depleted grafts in partial T-cell depleted allogeneic stem cell transplantation. Bone Marrow Transplantation. 2010; 45(2):S76.

Bleakley, et al., Naive T cell depletion to prevent graft-versus-host disease. National Institutes of Health. 2015. Fiscal Year 2014.

Bleakley, et al., Naive T cell depletion to prevent graft-versus-host disease. National Institutes of Health. 2015. Fiscal Year 2015.

Bleakley, et al., Naive T cell depletion to prevent graft-versus-host disease. National Institutes of Health. 2015. Fiscal Year 2016.

Bleakley, et al., Naive T cell depletion to prevent graft-versus-host disease. National Institutes of Health. 2015. Fiscal Year 2017.

Golubovskaya, et al., Different subsets of T cells, memory, effector functions, and CAR-T immunotherapy. Cancers 2016, 8, 36; doi:10.3390/cancers8030036.

Stemcell Technologies, Frequencies of cell types in human peripheral blood. 2017, Version 4.0.0, Document #23629, 1 Page.

Takahashi, et al., CD4+ T cells in aged or thymectomized recipients of allogeneic stem cell transplantations. Biol Res (2015) 48:41.

Anderson et al., "Memory CD4$^{30}$ T cells do not induce graft-versus-host disease," *The Journal of Clinical Investigation* 112(1):101-108, 2003.

Choi, et al. Current and emerging strategies for the prevention of graft versus host disease. Nat Rev Clin Oncol. Sep. 2014; 11(9): 536-547.

\* cited by examiner

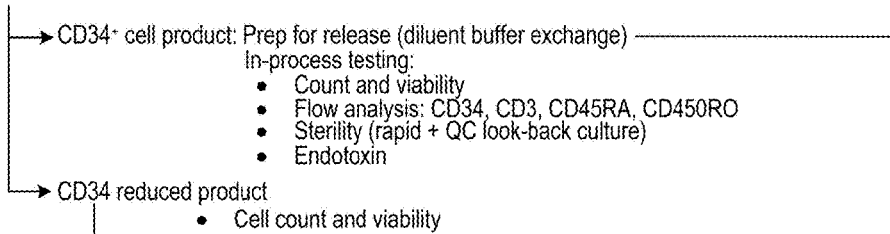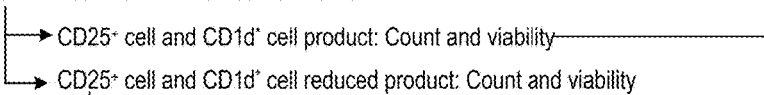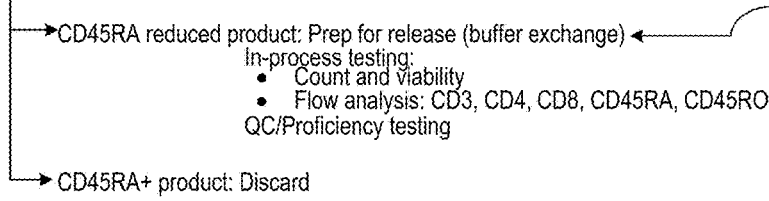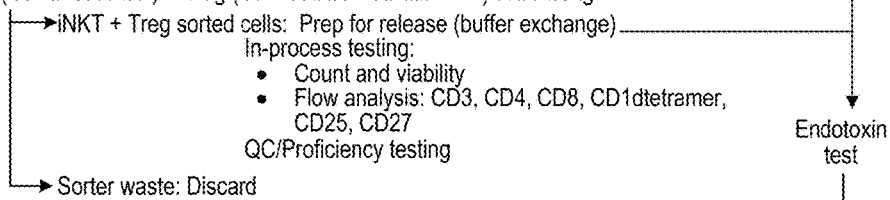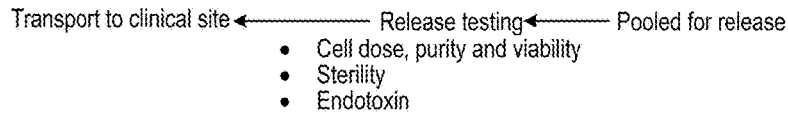
FIG. 14

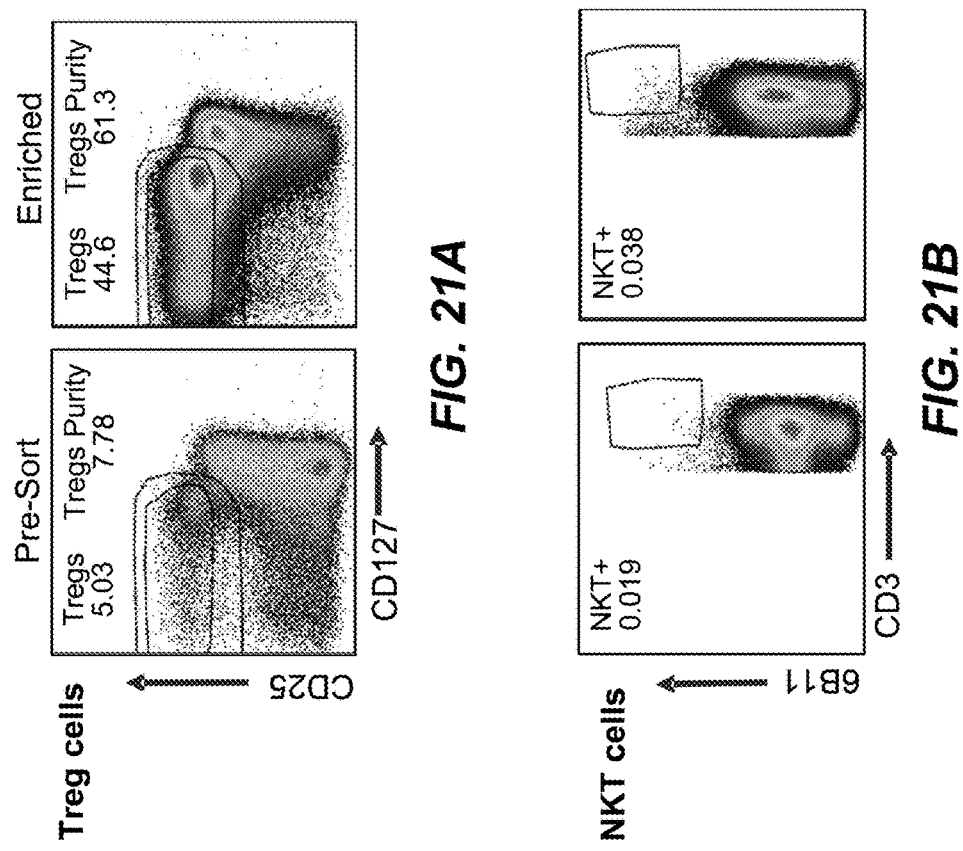

US 10,300,090 B2

COMPOSITIONS OF HEMATOPOIETIC STEM CELL TRANSPLANTS

CROSS REFERENCE TO RELATED APPLICATION

This application claims the benefit under 35 U.S.C. § 119(e) to U.S. Provisional Application No. 62/471,769, filed Mar. 15, 2017, which application is hereby incorporated by reference in its entirety.

BACKGROUND

Allogeneic hematopoietic stem cell transplantation (HSCT) generally involves transferring the hematopoietic cells from an immunologically compatible healthy person (the donor) to a patient after a conditioning regimen. Healthy hematopoietic stem cells (HSC) can replace the damaged hematopoietic tissue of a patient, and specific donor derived immune cells can have a therapeutic effect on cancer, infections, and immunological diseases. However, the current methods of allogeneic HSCT include either a heterogeneous mixture of cells that include contaminating, non-therapeutic cells or a purified, but limited mixture of cells that lacks the potential therapeutic benefit of a complete graft. In the former scenario, while many of the non-therapeutic cells contaminating the therapeutically relevant cells are harmless, even a small population of a specific errant cell type can cause severely adverse consequences in the recipient. For example, residual tumor cells, or teratoma initiating cells, that contaminate a population of transplanted cells can seed a tumor in a patient. In another example, subsets of circulating T cells can initiate graft-versus-host-disease (GVHD) a serious and often fatal complication of allogeneic HSCT. In these instances, the pathology arising from the contaminating cells supersedes the therapeutic benefits of other T cells introduced during transplantation. In many cases allogeneic HSC T is a curative therapy for the underlying disorder, however when contaminating cells of the graft react against to their new host environment, it is indeed the medical treatment that does harm to the patient. Therefore, there is a high, unmet need for HSC transplant compositions with a reduced number of deleterious cells and an optimal mixture of therapeutic cells.

SUMMARY

In some embodiments disclosed herein is a pharmaceutical composition, comprising one or more unit doses of a cellular graft, wherein each unit dose of the cellular graft comprises populations of therapeutic cells for each kilogram (kg) of body weight of a subject receiving the cellular graft. In some embodiments, the populations of therapeutic cells of each unit dose comprise more than $3 \times 10^5$ hematopoietic stem/progenitor cells (HSPC), more than $3 \times 10^5$ memory T cells (Tmem), more than $5 \times 10^5$ regulatory T cells (Treg), and less than $3 \times 10^5$ naïve conventional αβ-T cells. In some embodiments, the unit dose further comprises $0.5 \times 10^3$ to $2000 \times 10^3$ invariant natural killer T (iNKT) cells. In some embodiments, the HSPC are CD3$^+$, the Tmem are CD3$^+$ CD45RA$^-$ CD45RO$^+$, the Treg are CD4$^+$CD25$^+$CD127$^{-/lo}$, CD45RA$^+$, or a combination thereof, and the naïve conventional αβ-T cells are CD3$^+$CD45RA$^+$CD25$^-$ Va24Ja18$^-$. In some embodiments, the iNKT are CD3$^+$Vα24Jα18$^+$.

In some embodiments, the pharmaceutical composition disclosed herein comprises a population of therapeutic cells that is enriched for HSPC), memory T cells (Tmem), and Treg, and wherein the population of cells is depleted of naïve conventional αβ-T cells, wherein the population of therapeutic cells comprises a ratio of naïve conventional αβ-T cells to Treg less than 1:5. In some embodiments, the pharmaceutical composition further comprises invariant iNKT and the population of therapeutic cells comprises a ratio of naïve conventional αβ-T cells to iNKT less than 100:1. In some embodiments, the population of therapeutic cells comprises, a ratio of naïve conventional αβ-T cells to HSPC that is less than 1:400; and a ratio of naïve conventional αβ-T cells to Tmem less than 1:800. In some embodiments, the population of therapeutic cells comprises iNKT and population of therapeutic cells comprises a ratio of naïve conventional αβ-T cells to HSPC less than 1:400; a ratio of naïve conventional αβ-T cells to Tmem less than 1:800; and a ratio of naïve conventional αβ-T cells to iNKT is less than 100:1. In some embodiments, the population of therapeutic cells comprises a ratio of naïve conventional αβ-T cells to HSPC less than 1:400. In some embodiments, the population of therapeutic cells comprises a ratio of naïve conventional αβ-T cells to Tmem less than 1:3.

In some embodiments disclosed herein is a method of treating a disease or disorder, comprising administering a therapeutic population of cells to a subject in need thereof, wherein the therapeutic population of cells comprises HSPC at a concentration of $1.0 \times 10^6$ to $50 \times 10^6$ cells/kg of subject weight, Tmem at a concentration of $0.1 \times 10^6$ to $1000 \times 10^6$ cells/kg of subject weight, Treg at a concentration of $0.1 \times 10^6$ to $1000 \times 10^6$ cells/kg of subject weight, and naïve conventional αβ-T at a concentration of less than $3 \times 10^5$ cells/kg of subject weight. In some embodiments, the therapeutic population of cells further comprises iNKT cells at a concentration of $0.5 \times 10^3$ to $2000 \times 10^3$ cells/kg of subject weight.

In some embodiments, disclosed herein is a method of producing a pharmaceutical composition comprising, processing at a least one sample to provide a population of therapeutic cells by:

A. contacting the sample with a binding molecule that specifically binds CD34 under conditions to provide a population enriched for CD34$^+$ cells and a population of CD34-depleted cells, recovering the population enriched for CD34$^+$ cells, and recovering the population of CD34-depleted cells; and B. contacting the population of CD34-depleted cells with a binding molecule that specifically binds CD25 under conditions to provide a population enriched for CD25$^+$ cells and a population of CD25-depleted cells, recovering the population enriched for CD25$^+$ cells, and recovering the population of CD25-depleted cells; and C. contacting the population of CD25-depleted cells with a binding molecule that specifically binds CD45RA under conditions to provide a population enriched for CD45RA$^+$ cells and a population of CD45RA-depleted cells, and recovering a population of CD45RA-depleted cells; and D. formulating the population enriched for CD34+ cells, the population enriched for CD25$^+$ cells and the population of CD45-depleted cells as a pharmaceutical composition suitable for administration to a subject.

BRIEF DESCRIPTION OF THE DRAWINGS

FIG. 1A shows a schematic representation of a process for producing a sculpted graft cellular composition. FIG. 1B shows a schematic representation of a process for producing a sculpted graft cellular composition.

FIG. 2A shows a schematic representation of a process for producing a sculpted graft cellular composition. FIG. 2B shows a schematic representation of a process for producing a sculpted graft cellular composition.

FIG. 14 shows a schematic representation of a process for producing a sculpted graft cellular composition.

FIG. 17A. Kaplan-Meier curves of percent survival over time. FIG. 17B. Final outcomes assessed as overall survival, relapse, engraftment failure, and GVHD. FIG. 17C. Exemplary micrograph of J774 GPF-Luc tumors in the spleen dissected from a HSCT mouse. FIG. 17D. Representative bioluminescent image comparing presence of GFP+ cells generated using a Xenogen IVIS100 on day +10.

FIG. 21A-B depicts enrichment of regulatory T cells and iNKT cells from peripheral blood monocytes (PBMCs) using MACS. FIG. 21A shows flow cytometry data showing the % purity and % yield of Tregs in pre-sort PBMCs and enriched populations.

FIG. 21B shows flow cytometry data showing the % purity and % yield of iNKT cells in the pre-sort PBMCs and enriched populations.

FIG. 22A shows % yield of CD3$^+$CD45RO$^+$ cells and ratio of naïve T:memory T cells produced using magnetic sorting of PBMCs. FIG. 22B shows flow cytometry data showing CD45RO and CD45RA cells in pooled PBMCs and CD45RA depleted samples.

FIG. 23A shows flow cytometry analysis of magnetically separated CD25+ cells demonstrating efficient separation of CD25+ CD127+ Treg and characterizing the subpopulations of memory Treg and naïve Treg cells. FIG. 23B shows exemplary performance of the magnetic separation strategy for Treg and naïve Treg from two donors.

FIG. 24A shows binding of the 6B11.1, 6B11.2, and 6B11.3 biotinylated antibodies to samples for three separate donors at increasing concentrations of 6B11 antibody from zero to 1 µg/µL. FIG. 24B shows flow cytometry analysis of 6B11 biotin/streptavidin PE-Cy7 staining and CD127 APC staining to a sample using a no-6B11 control or 6B11 antibody that was biotinylated with biotin at 100 µM (condition 1), 250 µM (condition 2), or 1 mM (condition 3).

DETAILED DESCRIPTION

Figure 1A:
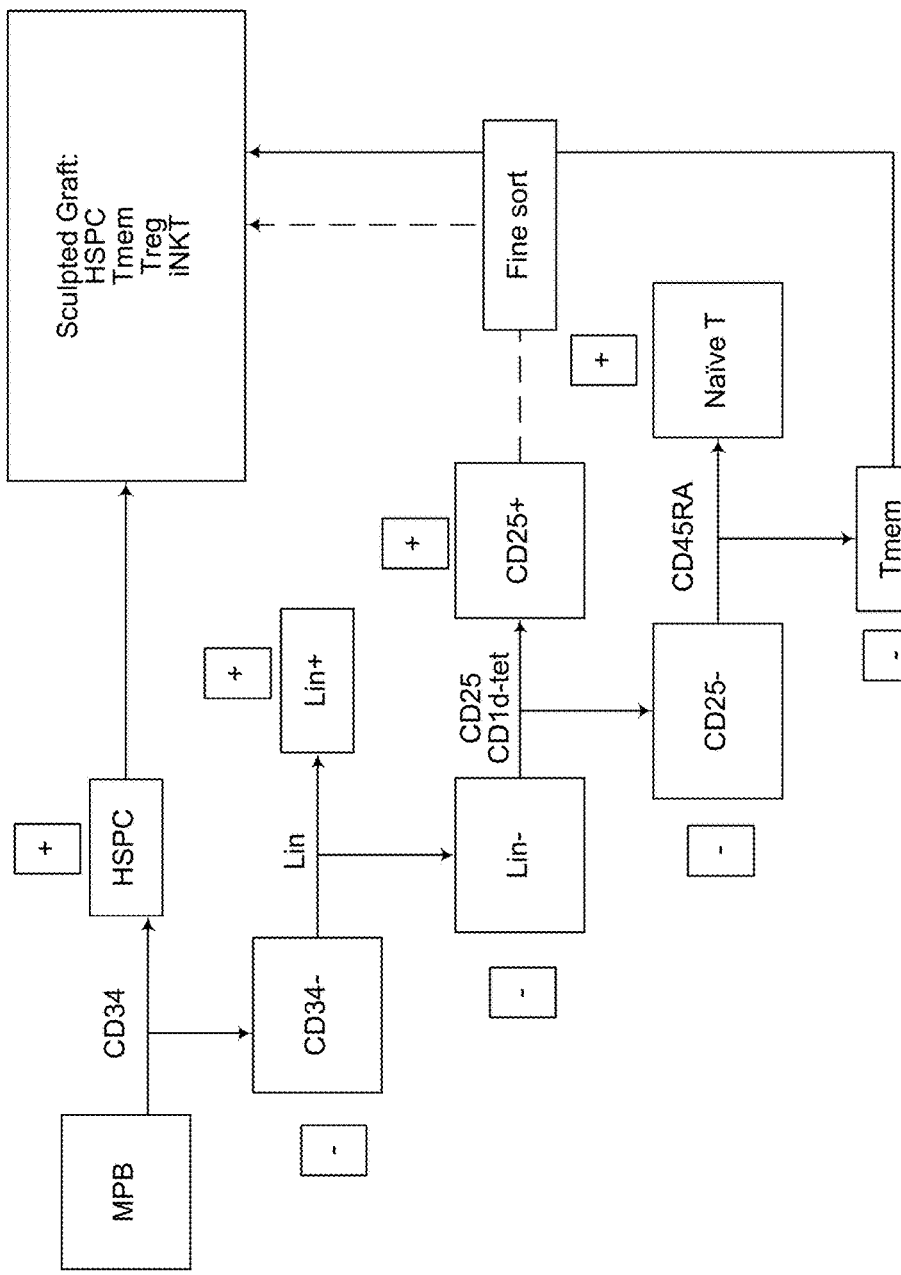
FIG. 1A-B.
Figure 1B:
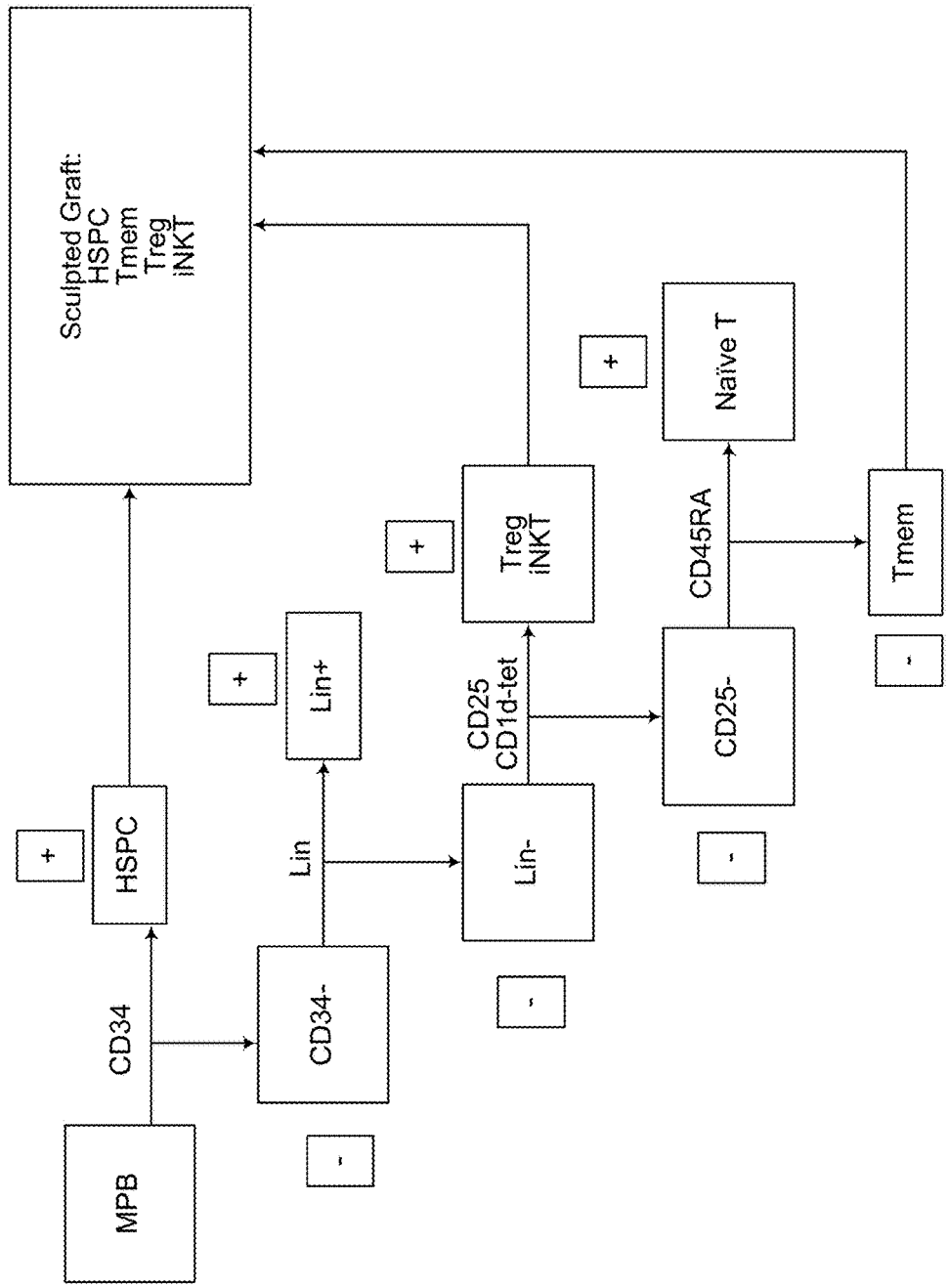

In certain embodiments, the present disclosure provides distinct therapeutic populations of cells that form a pharmaceutical composition useful in hematopoietic stem/progenitor cell transplant. For example, some embodiments of the present disclosure provides a therapeutic population of cells, comprising an enriched population of hematopoietic stem/progenitor cells (HSPC), memory T cells (Tmem), regulatory T cells (Treg), and wherein the population of cells is depleted of naïve conventional αβ-T cells. In some embodiments, the therapeutic population of cells further comprises invariant Natural Killer T (iNKT) cells. The present disclosure further provides methods of treatment using the therapeutic population of cells. In other embodiments, the present disclosure provides methods of producing a therapeutic population of cells.

The therapeutic cell populations have been sculpted to enrich the number of cells with therapeutic benefit and deplete the cell populations that are detrimental to a graft recipient (e.g., induce secondary disease). HSPC provide for short term benefits of reconstitution of blood and immune system functions such as restoring red blood cell, platelet, and neutrophil counts. Durable engraftment of HSPC provides for reconstitution of adaptive immune functions by producing T cell and B cell populations. Donor T cells as a general population are both beneficial and detrimental to engraftment. Tmem cells provide a benefit because Tmem mediate both Graft vs. Infection effects and Graft vs. Leukemia effects with a reduced risk of Graft versus Host Disease (GVHD). Naïve and memory Treg cells provide a benefit because Tregs help prevent graft rejection and prevent GVHD. In contrast, naïve conventional T cells are a cause of GVHD and improper immune reconstitution. Therefore, reducing or eliminating naïve conventional T cells in the sculpted graft disclosed herein enhances the therapeutic benefit by reducing the incidence of GVHD in the graft recipient.

Definitions

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, the term "therapeutic cell" refers to a cell that is selected or administered to a subject based on the ability of the cell to offer a therapeutic benefit to a subject. Exemplary therapeutic cells include hematopoietic stem/progenitor cells, memory T cells, regulatory T cells, and invariant natural killer T cells. A population of therapeutic cells can include more than one type of therapeutic cell, e.g., HSPC, Tmem, Treg, iNKT or any combination thereof. A population of therapeutic cells can comprise essentially a single therapeutic cell type. In the context of a population of therapeutic cells, a percentage (%) of therapeutic cells refers to the percent of a cell-type that is included in a combination or composition of therapeutic cells in which the total number of therapeutic cells adds up to 100% and the specific therapeutic cell type represents a portion of the total number of therapeutic cells. For example, a population therapeutic cells comprising 30% HSPC indicates that approximately 30% of the total population of therapeutic cells is HSPC. A population of therapeutic cells can exist within a larger population of cells that have a neutral effect on the subject and the neutral cells are not included in the calculation of total therapeutic cells.

As used herein, the term "hematopoietic stem/progenitor cells" or "HSPC" refer to hematopoietic stem cells and/or hematopoietic progenitor cells that express increased levels of phenotypic markers CD34, CD133, CD90, or any combination thereof, relative to other types of hematopoietic cells (e.g., the cells are positive for expression of the phenotypic marker as determined by flow cytometry, western blot, or other methods known in the art). Also, the HSPC can be negative for an expressed marker relative to other types of hematopoietic cells. For example, such markers include CD19, TCRα, TCRβ, CD45RA, Lin, CD38, or any combination thereof. Preferably, the HSPC are CD34$^+$ cells and/or CD19$^-$ TCRα$^-$. HSPC can self-renew or can differentiate into (i) myeloid progenitor cells, which ultimately give rise to monocytes and macrophages, neutrophils, basophils, eosinophils, erythrocytes, megakaryocytes/platelets, or dendritic cells; or (ii) lymphoid progenitor cells which ultimately give rise to T-cells, B-cells, and lymphocyte-like cells called natural killer cells (NK-cells). For a general discussion of hematopoiesis and HSPC differentiation, see Rowe et al. *Cell Stem Cell*. 2016. 18:707-720.

As used herein, the term "naïve conventional αβ-T cells" or "naïve Tcon" refers to a non-antigen experienced T cell that expresses the phenotypic markers TCRα/β, CD45RA, and expresses medium to high levels of CD127 (CD127$^+$), and does not express or has low expression of CD45RO and CD25. In some embodiments, naïve Tcon are characterized by the expression of phenotypic markers of naïve Tcon including TCRα, TCRβ, CD3, CD4 or CD8, CD62L, CCR7, CD28, CD127, and CD45RA. In some embodiments a naïve Tcon is CD3$^+$ CD25$^-$ CD45RA$^+$ and comprises a polymorphic TCRα, and a polymorphic TCRβ. In some embodiments, naïve Tcon are not naïve T regulatory cells, as defined herein. Naïve Tcon cells do not express the Vα24Jα18 TCR found on iNKT cells.

As used herein, the term "regulatory T cell" or "Treg" refers to a subclass of T cell that is capable of suppressing autoimmune reactions and expresses the phenotypic markers CD4, CD25, and has no or low expression of CD127. Treg also express FOXP3, however, CD127 expression has been demonstrated to correlate inversely with FOXP3 expression on CD4$^+$CD25$^+$ cells, and the CD4$^+$CD25$^+$CD127$^{-/low}$ phenotype is considered to be an acceptable surrogate marker for Tregs and a practical alternative to intracellular staining for FOXP3 (Cozzo C, et al. *J. Immunol.* 2003 Dec. 1; 171:5678-82; Liu W, et al. *J Exp. Med.* 2006. 203(7):1701-1711; Seddiki N, et al. *J Exp. Med.* 2006; 203(7):1693-1700). Tregs can include at least two subclasses referred to herein as naïve Tregs and memory Tregs.

As used herein, the term "naïve Treg" is a non-antigen experienced regulatory T cell that expresses the phenotypic markers CD4, CD25, and CD45RA as a primary cell, and does not express or has low expression of CD45RO and CD127. Naïve Tregs are advantageous because the cells have higher plasticity for responding to antigens than antigen experienced Tregs. In addition, naïve Tregs have increased longevity compared to antigen experienced Tregs.

As used herein, the term "memory Treg" is an antigen experienced regulatory T cell that is capable of providing suppressive effects on autoimmunity and expresses the phenotypic markers CD4, CD25, and CD45RO and does not express or has low expression of CD127 and CD45RA.

As used herein, the term "memory T cell" or "Tmem" refers to antigen experienced T cells that express the phenotypic markers TCRα, TCRβ, CD3, CD4 or CD8, CD95, and IL-2Rβ. Memory T cells provide immunity and are capable of persisting for a long period of time in an inactive state. Memory T cells are able to rapidly acquire effector functions upon re-challenge with antigen. A population of memory T cells can include the any combination of the subclasses T central memory cells ($T_{CM}$) and T effector memory cells ($T_{EM}$).

As used herein, "T central memory cell" or "$T_{CM}$" refers to an antigen experienced T cell that expresses the phenotypic markers CD4 or CD8, CD62L, CD45RO, CCR7, IL-2Rβ, CD28, CD127, and CD95 and does not express or has low expression of CD45RA as compared to naïve Tcon cells. Central memory T cells can differentiate into $T_{EM}$ cells following antigen re-challenge.

As used herein, "T effector memory cell" or "$T_{EM}$" refers to an antigen experienced T cell that expresses the phenotypic markers CD4 or CD8, CD45RO, CD127, IL-2Rβ, and CD95, and does not express or has low expression of CD45RA, CD62L, CCR7, and CD28. T effector memory cell are terminally differentiated and acquire effector function after re-stimulation by antigen.

As used herein, "T stem central memory cell" or "$T_{SCM}$" refers to an antigen experienced T cell that expresses the phenotypic markers CD4 or CD8, CD45RA, CD62L, CD95, IL-2Rβ, CCR7, CXCR3, CD122, and LFA-1. $T_{SCM}$ cells possess memory T cell capability of rapid acquisition of effector function following antigen re-challenge, but have enhanced stem cell-like qualities such as long-term persistence compared to $T_{CM}$ cells. $T_{SCM}$ cells can generate central memory, effector memory, and effector T cell subsets.

As used herein, "invariant Natural Killer T cells" or "iNKT" is a subclass of CD1d-restricted Natural Killer T (NKT) cells that express a highly conserved αβ-T cell receptor that comprises of Vα24Jα18 TCRα chain in humans (referred to herein as "Vα24Jα18$^+$"). iNKT cells can be identified by binding with CD1d-multimers like that are loaded with α-galactosylceramide (GalCer), PBS-57, PBS-44 or other natural or synthetic glycolipids, and can be found as tetramers, dendrimers, and other structures, Fc fusions, or any combination thereof. Another method of identification is an antibody or combination of antibodies that specifically recognize the Vα24Jα18 region. Examples include a Vα24 antibody, a Jα18 antibody, or the monoclonal antibody clone 6B11 which binds specifically to a unique region of the Vα24Jα18 TCR and can be used to identify iNKT cells (Montoya et al. *Immunology.* 2007. 122(1):1-14). In some embodiments, iNKT cells are CD1d-tetramer glycolipid loaded$^+$ (CD1d-tet$^+$), 6B11$^+$, or both. iNKT cells may be interchangeably referred to herein as CD1d-tet$^+$, 6B11$^+$, or Vα24Jα18$^+$ cells. Without wishing to be limited to a particular mechanism, it is thought that iNKT cells promote/accelerate the activity of Treg and HSPC.

As referred to herein, "lineage positive" or "Lin$^+$" cells express the phenotypic markers such as CD19, CD11c, CD66B, CD14, CD20, or any combination thereof. As referred to herein, "lineage negative" or "Lin$^-$" cells do not express or have low expression of the phenotypic markers CD19, CD11c, CD66B, CD14, CD20, or any combination thereof compared to HSPC, Treg, Tmem, or iNKT cells. Lin$^+$ cells express phenotypic markers that are present on mature erythroid cells, granulocytes, macrophages, NK cells, and B and T lymphocytes.

As used herein, "sample" refers to a cell source (e.g. biological tissue) from which a population of cells may be isolated, enriched, or depleted. In some embodiments, a sample has generally not been previously processed or has been minimally processed. For example, the sample may be mobilized peripheral blood, mobilized apheresis product, bone marrow, umbilical cord blood, non-mobilized blood, non-mobilized apheresis product, or any combination thereof. In some embodiments, the sample is prepared or minimally processed by processing with a density gradient, Ficoll, Percoll, red blood cell hypotonic lysis, Ammonium-Chloride-Potassium (ACK) buffer, washed into a pH balanced isotonic buffer, or any combination thereof. In some embodiments, the sample is provided by a single tissue harvest. In some embodiments, the sample is provided by one or more tissue harvests.

As used herein, "donor" refers to one or more individuals from which a sample is obtained. For example, a donor may refer to an human leukocyte antigen (HLA) matched sibling, an HLA matched unrelated donor, a partially matched unrelated donor, a haploidentical related donor, autologous donor, an HLA unmatched allogenic donor, a pool of donors, or any combination thereof. In some embodiments a donor may be a subject. "Donor tissue" refers to tissue harvested from a donor. Donor tissue can be a sample. The donor tissue is generally the same species as the subject.

As used herein, "subject" or "recipient" refers to one or more individuals that are in need of receiving treatment, therapy, or cellular graft disclosed herein. Subjects that can be treated by the present invention are, in general, human. However, additional subjects include a non-human primate, cow, horse, sheep, goat, pig, dog, cat, mouse, rabbit, rat, or Guinea pig. The subjects can be male or female and can be any suitable age, including infant, juvenile, adolescent, adult, and geriatric subjects. During and following the treatment, a subject becomes a recipient or graft recipient.

As used herein, "tissue harvest" refers a process of collecting a donor tissue or a sample from a donor. Non-limiting examples of a tissue harvest include collecting bone marrow, peripheral blood, umbilical cord blood, etc. from a donor. A tissue harvest may be performed by any method which known in the art.

As used herein, "enriched" with respect to a population of a cells or cell-types in a mixture refers a population of cells that has been processed to increase the relative amount or ratio of the enriched cell-type relative to other cells (e.g., accounting cell-types) in the mixture. Thus, depending upon the source of the original population of cells subjected to the enriching process, a mixture or composition can contain 30%, 35%, 40%, 45%, 50%, 55%, 60%, 65%, 70%, 75%, 80%, 85%, 90%, 91%, 92%, 93%, 94%, 95%, 96%, 97%, 98%, or 99% or more (in number or count) of the "enriched" population of cells relative to other cells in the mixture. In some embodiments, the enrichment process can result in a 1.5-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 50-fold, 100-fold, 200-fold, 300-fold, 400-fold, 500-fold, 600-fold, 700-fold, 800-fold, 900-fold, 1,000-fold, 5,000-fold, 10,000-fold or more of the "enriched' population of cells relative to other cells in the mixture. For example, in some embodiments, a mixture of cells that is enriched for iNKT cells may comprise about 0.03 to 1% iNKT cells, 0.05% to 0.5% iNKT cells, 0.1% to 1% iNKT cells, or any combination thereof. Exemplary methods of enriching a cell population include magnetic activated cell sorting (MACS) and fluorescence activated cell sorting (FACS).

As used herein, "depleted" with respect to a population of a cells or cell-types in a mixture refers a population of cells that has been processed to decrease the relative amount or ratio of the depleted cell-type relative to other cells (e.g., accounting cell-types) in the mixture. In some embodiments, cells subjected to a depleting process can result in a mixture or composition containing 50%, 45%, 40%, 35%, 30%, 25%, 20%, 15%, 10%, 9%, 8%, 7%, 6%, 5%, 4%, 3%, 2%, 1%, or 0.1%, 0.01%, 0.001%, 0.0001%, 0.00001%, 0.000001%, 0.0000001%, 0.00000001% or less (in number or count) of the "depleted" population of cells. In some embodiments, cells subjected to a depleting process can results in a mixture or composition containing 10-fold, 100-fold, 1,000-fold, 10,000-fold, 100,000-fold, 1,000,000-fold, 10,000,000-fold, or less of the depleted population relative to the unprocessed sample. In some embodiments, the depleted cell-type is no longer detectable using conventional methods following the processing step that depletes the cell-type.

In certain embodiments, amounts of a certain cell type in a mixture are enriched and amounts of a different cell type are depleted, such as enriching for CD34$^+$ cells while depleting CD34$^-$ cells.

A cell population "positive" for a marker refers to uniform staining of the cell population above the levels found on an isotype control. In some embodiments, a decrease in or low expression of one or more markers refers to a loss of or measure of at least 1 log 10 in the mean fluorescence intensity (MFI) less than a reference control. In some embodiments, an increase in or high expression of one or more markers refers to an increase or measure of MFI at least 1 log 10 higher than an isotype control or reference control. In some embodiments, an at least 2-fold increase in the MFI relative to the reference population indicates the cells are positive for expression of the marker. For example, a cell population that is positive for a marker can demonstrate a 2-fold to 4 fold, 4 fold to 10 fold, 10 fold to 100 fold, and 100 fold to 1,000 fold, 1,000 fold to 10,000 fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 50-fold, 100-fold, 200-fold, 300-fold, 400-fold, 500-fold, 600-fold, 700-fold, 800-fold, 900-fold, 1,000-fold, 5,000-fold, 10,000-fold or more higher MFI compared to an isotype control. In some embodiments, a cell population positive for of one or more markers refers to a percentage of cells that exhibit the marker, which can be at least 50% of the cells, 55% of the cells, 60% of the cells, 65% of the cells, 70% of the cells, 75% of the cells, 80% of the cells, 85% of the cells, 90% of the cells, 95% of the cells, and 100% of the cells and any % between 50% and 100% when compared to a reference cell population.

A cell population "negative" for a marker refers to the absence of significant staining of the cell population with the specific antibody above an isotype control. In some embodiments, an at least 2-fold decrease in the MFI relative to the reference population indicates the cells are negative for expression of the marker. For example, a cell population that is negative for a marker can demonstrate a 2-fold to 4 fold, 4 fold to 10 fold, 10 fold to 100 fold, and 100 fold to 1,000 fold, 1,000 fold to 10,000 fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 50-fold, 100-fold, 200-fold, 300-fold, 400-fold, 500-fold, 600-fold, 700-fold, 800-fold, 900-fold, 1,000-fold, 5,000-fold, 10,000-fold or more lower MFI compared to a positive control. In some embodiments, a decrease in or low expression of one or more markers refers to a percentage decrease of cells that exhibit the marker in a population of cells of at least 20% of the cells, 25% of the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 20% and 100% when compared to a reference cell population.

As used herein, "percent purity" or "% purity" refers to the number of target cells multiplied by 100 and then divided by the number of cellular events counted, as measured on a flow cytometer, hemocytometer, coulter counter, microscopy, or other cell counting method (# of target cells×100/# of cellular events).

As used herein, "overall percent yield" or "overall % yield" refers to the number of target cells after a processing step times 100 and then divided by number of target cells in the original population (# of target cells after a processing step×100/# of target cells in the original population). The "percent yield of a processing step" or "% yield of a processing step" refers to the number of target cells after a processing step times 100 and then divided by number of target cells in the preprocessed population (# of target cells after a processing step×100/# of target cells in the preprocessed population)

As used herein, "rough sort" refers to a method of enriching or depleting a population of cells wherein depending upon the source of the original population of cells subjected to the rough sort, the resulting population can contain at least 30%, 35%, 40%, 45%, 50%, 55%, 60%, 65%, 70%, 75%, 80%, 85%, 90%, 95%, or greater of a particular cell population compared to the starting mixture of cells. Methods of performing a rough sort a well-known in the art and can include density separation, apheresis/leukapheresis, tetrameric antibody complex mediated enrichment/depletion, and magnetic activated cell sorting (MACS), such as CLINIMACS®, PRODIGY®, or EASY-SEP™/ROBOSEP™.

As used herein, "fine sort" refers to a method of enriching or depleting a population of cells wherein the resulting population can contain at least 90%, 91%, 92%, 93%, 94%, 95%, 96%, 97%, 98%, 99%, 99.9%, or greater of a particular cell population or populations compared to the starting mixture of cells. Methods of performing a fine sort a well-known in the art and can include multi-parameter fluorescence based molecular phenotypes such as fluorescence-activated cell sorting (FACS) and microfluidics based sorting. Additional methods of performing a fine sort are provided, for example, in U.S. Provisional Patent Application No. 62/421,979, which are hereby incorporated by reference in its entirety.

As used herein, the term "binding molecule" may be any of a large number of different molecules, or aggregates, and the terms are used interchangeably. Proteins, polypeptides, peptides, nucleic acids (nucleotides, oligonucleotides and polynucleotides), antibodies, saccharides, polysaccharides, lipids, receptors, test compounds (particularly those produced by combinatorial chemistry), may each or in combination (when bound to each other alone or via the target ligand) be a binding molecule.

As used herein, "specifically binds" or "specific for" refers to an association or union of a binding molecule (e.g., antibody) or a binding domain to a target (molecule or complex) with an affinity or Ka (i.e., an equilibrium association constant of a particular binding interaction with units of 1/M) equal to or greater than $10^5 M^{-1}$ (which equals the ratio of the on-rate $[k_{on}]$ to the off-rate $[k_{off}]$ for this association reaction), while not significantly associating or uniting with any other molecules or components in a sample. Binding molecules or binding domains may be classified as "high affinity" binding molecules or binding domains or as "low affinity" binding molecules or binding domains. "High affinity" binding molecules or binding domains refer to those binding molecules or binding domains having a $K_a$ of at least $10^7 M^{-1}$, at least $10^8 M^{-1}$, at least $10^9 M^{-1}$, at least $10^{10} M^{-1}$, at least $10^{11} M^{-1}$, at least $10^{12} M^{-1}$, or at least $10^{13} M^{-1}$. "Low affinity" binding molecules or binding domains refer to those binding molecules or binding domains having a $K_a$ of up to $10^7 M^{-1}$, up to $10^6 M^{-1}$, up to $10^5 M^{-1}$. Alternatively, affinity may be defined as an equilibrium dissociation constant ($K_d$) of a particular binding interaction with units of M (e.g., $10^{-5}$ M to $10^{-13}$ M).

As used herein, a "sculpted cellular graft" or "sculpted graft" refers to population of cells that has been processed from a starting population of cells to provide numbers of specific cell-types within a specified range and to reduce or remove undesired cell-types to a specified range. Ranges are typically provided as a number of cells of a particular variety per kg of patient body weight, but may also be represented as a total number within the graft. A sculpted cellular graft can comprise a mixture of cells that include target cell to accounting cell ratios that do not occur in nature or percentage representations that do not occur in nature.

As used herein, a "unit dose" of refers to specified minimum numbers, specified numbers, or ranges of populations of therapeutic cells for each kilogram (kg) of body weight of a subject receiving a sculpted cellular graft. It is recognized that the number of unit doses varies depending on the size of the subject. A unit dose may be divided into a fraction of a unit dose depending on the weight of the subject. In some embodiments, the therapeutic cell populations (e.g., HPSC, Tmem, Treg, iNKT, etc.) may be divided into separate containers for administration to a subject.

Therapeutic Cellular Compositions

In certain embodiments, the present disclosure provided distinct therapeutic populations of cells that form a pharmaceutical composition useful in hematopoietic stem/progenitor cell transplant. The therapeutic population of cells can comprise an enriched population of hematopoietic stem/progenitor cells (HSPC), memory T cells (Tmem), regulatory T cells (Treg), and wherein the population of cells is depleted of naïve conventional αβ-T cells. In some embodiments, the Treg comprise naïve Treg, memory Treg, or both. In some embodiments, the Tmem comprise T stem central memory cells ($T_{SCM}$), a population of T central memory cells ($T_{CM}$), a population of T effector memory cells ($T_{EM}$), or any combination thereof. In some embodiments, the therapeutic population includes an enriched population of invariant Natural Killer T cells (iNKT).

In some embodiments, the therapeutic composition may comprise HSPCs and Tmems. In some cases, the therapeutic composition may comprise HSPCs, Tmems and Tregs. In some cases, the therapeutic composition may comprise HSPCs and Tregs. In some cases, the therapeutic composition may comprise HSPCs and iNKT cells. In some cases, the therapeutic composition may comprise HSPCs, Tregs, Tmems and iNKT cells.

In certain embodiments of this disclosure, the HSPC are $CD34^+$. The HSPC can be further or alternatively described as $CD133^+$, $CD90^+$, $CD38^-$, $CD45RA^-$, $Lin^-$, or any combination thereof. In some embodiments, the HSPC are $CD19^-$, $TCR\alpha/\beta^-$, or a combination thereof. In some embodiments, the Treg are $CD25^+$, $CD4^+$, and $CD127^{-/lo}$ cells, or any combination thereof. In some embodiments, the Treg are $CD4^+$, $CD25^+$, $CD127^{-/lo}$, $FoxP3^+$, or any combination thereof. In some embodiments, the naïve Treg are $CD4^+$, $CD25^+$, $CD127^{-/lo}$, $FoxP3^+$, $CD45RA^+$, $CD45RO^-$, or any combination thereof. In some embodiments, the memory Treg are $CD4^+$, $CD25^+$, $CD127^{-/lo}$, $FoxP3^+$, $CD45RA^-$, $CD45RO^+$, or any combination thereof. In some embodiments, the Tmem are $CD25^-$, $CD45RA^-$ cells or any combination thereof. In some embodiments, the Tmem are $CD3^+$, $CD45RA^-$, $CD45RO^+$, or any combination thereof. In some embodiments, the $T_{SCM}$ are $CD45RA^+$ and $CD4^+$ or $CD8^+$. The $T_{SCM}$ can further be described as $CD95^+$, $CD122^+$, $CXCR3^+$, $LFA-1^+$, or any combination thereof. In some embodiments, the $T_{CM}$ are $CD45RO^+$ and $CD4^+$ or $CD8^+$. The $T_{CM}$ can further be described as $CD45RA^-$, $CD62L^+$, $CCR7^+$, or any combination thereof. In some embodiments, the $T_{EM}$ are $CD4^+$, $CD45RO^+$, $CD45RA^-$, $CD62L^-$, $CCR7^-$, or any combination thereof. In some embodiments, the iNKT are $CD1d-tet^+$, $6B11^+$, or both. In some embodiments, the iNKT are $V\alpha24J\alpha18^+$. In some embodiments, the iNKT cells may be $CD25^+$, $6B11^+$, $CD4^+$, $V\alpha24J\alpha18^+$, $CD127^{dim/-}$ cells or any combination thereof. In any of the embodiments described herein, the naïve conventional αβ-T cells are $CD25^-$, $CD45RA^+$ or any combination thereof. In some embodiments, the naïve conventional αβ-T cells can be $TCR\alpha/\beta^+$ $CD45RA^+$ and $CD25^-$, $CD127^+$, or both. The naïve conventional αβ-T cells can further be described as $TCR\alpha^+$ $TCR\beta^+$ $CD45RA^+$ $CD45RO^-$ $CD25^-$ $CD95^-$ $IL-2R\beta^-$ $CD127^+$ $V\alpha24J\alpha18^-$.

In certain embodiments, the concentration of therapeutic cells is described as a ratio of HSPC to another cell type. In some embodiments, the ratio of HSPC to Tmem comprises a range from 500:1 to 1:1,000, 400:1 to 1:1,000, 300:1 to 1:1,000, 200:1 to 1:1,000, 100:1 to 1:1,000, 50:1 to 1:1,000, 10:1 to 1:1,000, 5:1 to 1:1,000, 4:1 to 1:1,000, 3:1 to 1:1,000, 2:1 to 1:1,000, 1:1 to 1:1,000, 500:1 to 1:900, 500:1 to 1:800, 500:1 to 1:700, 500:1 to 1:600, 500:1 to 1:500, 500:1 to 1:400, 500:1 to 1:300, 500:1 to 1:200, 500:1 to 1:100, 500:1 to 1:50, 500:1 to 1:20, 500:1 to 1:10, 500:1 to 1:9, 500:1 to 1:8, 500:1 to 1:7, 500:1 to 1:6, 500:1 to 1:5, 500:1 to 1:4, 500:1 to 1:3, 500:1 to 1:2, 500:1 to 1:1, 400:1 to 1:900, 300:1 to 1:800, 200:1 to 1:700, 100:1 to 1:600, 50:1 to 1:500, 10:1 to 1:400, 5:1 to 1:300, 4:1 to 1:200, 3:1 to 1:100, 2:1 to 1:50, or 1:1 to 1:20.

In some embodiments, the ratio of HSPC to Tmem comprises a range from 10:1 to 1:200, 100:1 to 1:2,000, or 1,000:1 to 1:20,000.

The ratio of HSPC to Treg can comprise a range from 20:1 to 1:3, 100:1 to 1:30, or 200:1 to 1:300. The ratio of HSPC to naïve Treg can comprise a range from 1:500 to 100:1, 1:400 to 100:1, 1:300 to 100:1, 1:200 to 100:1, 1:100 to 100:1, 1:50 to 100:1, 1:20 to 100:1, 1:10 to 100:1, 1:5 to 100:1, 1:1 to 100:1, 1:200 to 50:1, 1:200 to 20:1, 1:200 to 10:1, 1:200 to 5:1, 1:100 to 1:1, 40:1 to 1:3, 200:1 to 1:15, or 400:1 to 1:150. The ratio of HSPC to Memory Treg can comprise a range from 1:500 to 10,000:1, 1:400 to 10,000:1, 1:300 to 10,000:1, 1:200 to 10,000:1, 1:100 to 10,000:1, 1:50 to 10,000:1, 1:20 to 10,000:1, 1:10 to 10,000:1, 1:5 to 10,000:1, 1:1 to 10,000:1, 1:500 to 5,000:1, 1:500 to 1,000:1, 1:500 to 900:1, 1:500 to 800:1, 1:500 to 700:1, 1:500 to 600:1, 1:500 to 500:1, 1:500 to 400:1, 1:500 to 300:1, 1:500 to 200:1, 1:500 to 100:1, 1:500 to 50:1, 1:500 to 20:1, 1:500 to 10:1, 1:500 to 5:1, or 1:500 to 1:1.

The ratio of HSPC to iNKT can comprise a range from 1:2 to 1,000,000:1, 1:2 to 500,000:1, 1:1 to 500,000:1, 100:1 to 1,000,000:1, 100:1 to 500,000:1, 100:1 to 100,000:1, 500:1 to 1,000,000:1, 500:1 to 500,000:1, 500:1 to 100,000:1, 1,000:1 to 100,000:1, 1,000:1 to 1,000,000:1, 1,000:1 to 500,000:1, 1,000:1 to 100,000:1, 10,000:1 to 1:2, 100,000:1-1:20, or 1,000,000:1-1:200.

In certain embodiments, the concentration of therapeutic cells is described as a ratio of naïve conventional αβ-T cells to a therapeutic cell type. The ratio of naïve conventional αβ-T cells to HSPC can be less than 1:3, less than 1:50, less than 1:100, less than 1:200, less than 1:300, less than 1:400, less than 1:500, less than 1:600, less than 1:700, less than 1:800, less than 1:900, less than 1:1,000, less than 1:1,500, less than 1:2,000, less than 1:3,000, less than 1:4,000, less than 1:5,000, less than 1:6,000, less than 1:7,000, less than 1:8,000, less than 1:9,000, less than 1:10,000, less than 1:50,000, less than 1:100,000, less than 1:200,000, less than 1:300,000, less than 1:400,000, less than 1:500,000, less than 1:600,000, less than 1:700,000, less than 1:800,000, less than 1:900,000, less than 1:1,000,000.

The ratio of naïve conventional αβ-T cells to Tmem can be less than 1:30, less than 1:200, less than 1:300, less than 1:400, less than 1:500, less than 1:600, less than 1:700, less than 1:800, less than 1:900, less than 1:1000, less than 1:5000, less than 1:10000, less than 1:15000, less than 1:20000, less than 1:25000, less than 1:30000, less than 1:35000, less than 1:40000, less than 1:45000, or less than 1:50000.

The ratio of naïve conventional αβ-T cells to Treg can be less than 1:1, less than 1:2, less than 1:3, less than 1:4, less than 1:5, less than 1:6, less than 1:7, less than 1:8, less than 1:9, 1:10, less than 1:15, less than 1:20, less than 1:30, less than 1:200, less than 1:300, less than 1:400, less than 1:500, less than 1:600, less than 1:700, less than 1:800, less than 1:900, less than 1:1000, less than 1:5000, less than 1:10000, less than 1:15000, less than 1:20000, less than 1:25000, less than 1:30000, less than 1:35000, less than 1:40000, less than 1:45000, or less than 1:50000. The ratio of naïve conventional αβ-T cells to naïve Treg can be less than 1:1, less than 1:2, less than 1:3, less than 1:4, less than 1:5, less than 1:6, less than 1:7, less than 1:8, less than 1:9, 1:10, less than 1:15, less than 1:20, less than 1:30, less than 1:200, less than 1:300, less than 1:400, less than 1:500, less than 1:600, less than 1:700, less than 1:800, less than 1:900, less than 1:1000, less than 1:5000, less than 1:10000, less than 1:15000, less than 1:20000, less than 1:25000, less than 1:30000, less than 1:35000, less than 1:40000, less than 1:45000, or less than 1:50000. The ratio of naïve conventional αβ-T cells to Memory Treg can be less than 1:1, less than 1:2, less than 1:3, less than 1:4, less than 1:5, less than 1:6, less than 1:7, less than 1:8, less than 1:9, less than 1:10, less than 1:15, less than 1:20, less than 1:30, less than 1:200, less than 1:300, less than 1:400, less than 1:500, less than 1:600, less than 1:700, less than 1:800, less than 1:900, less than 1:1000, less than 1:5000, less than 1:10000, less than 1:15000, less than 1:20000, less than 1:25000, less than 1:30000, less than 1:35000, less than 1:40000, less than 1:45000, or less than 1:50000.

The ratio of naïve conventional αβ-T cells to iNKT can be less than 100:1, less than 1:1, less than 1:2, less than 1:3, less than 1:4, less than 1:5, less than 1:6, less than 1:7, less than 1:8, less than 1:9, less than 1:10, less than 1:15, less than 1:20, less than 1:30, less than 1:200, less than 1:300, less than 1:400, less than 1:500, less than 1:600, less than 1:700, less than 1:800, less than 1:900, less than 1:1000, less than 1:5000, less than 1:10000, less than 1:15000, less than 1:20000, less than 1:25000, less than 1:30000, less than 1:35000, less than 1:40000, less than 1:45000, less than 1:50000.

In some embodiments of the instant disclosure, the ratio of Tmem to Treg is not dependent on the concentration of starting cells (e.g. substantially modified from the starting concentrations). This provides an advantage because the concentration of Tmem can be controlled (e.g. dose escalated) independent of the concentration of Treg. The ratio of Tmem to Treg can be from 30:1 to 1:1, 25:1 to 1:1, 20:1 to 1:1, 15:1 to 1:1, 10:1 to 1:1, 9:1 to 1:1, 8:1 to 1:1, 7:1 to 1:1, 6:1 to 1:1, 5:1 to 1:1, 4:1 to 1:1, 3:1 to 1:1, 2:1 to 1:1. In certain embodiments, the ratio of Tmem to Treg can be from 1:1 to 200:1, 1:10 to 2000:1, or 1:100 to 20,000:1. The ratio of Tmem to naïve Treg can be from 5:1 to 1:10, 3:1 to 1:10, 3:1 to 1:10, 2:1 to 1:10, or 1:1 to 1:10. The ratio of Tmem to memory Treg can be from 27:1 to 0.9:1, 30:1 to 1:10, 25:1 to 1:10, 20:1 to 1:10, 15:1 to 1:10, 10:1 to 1:10, 30:1 to 1:9, 30:1 to 1:8, 30:1 to 1:7, 30:1 to 1:6, 30:1 to 1:5, 30:1 to 1:4, 30:1 to 1:3, 30:1 to 1:2, or 30:1 to 1:1.

In some embodiments of the instant disclosure, the ratio of Treg to iNKT can be from 20,000:1 to 1:5, 200,000:1 to 1:50, or 2,000,000:1 to 1:500.

In some embodiments of the instant disclosure, the ratio of iNKT to Tmem can be from 2:1 to 1:100,000, 5:1 to 1:1,000,000, or 10:1 to 1:10,000,000.

In some embodiments, the number of naïve conventional αβ-T cells in a composition can be less than about 2%, 5%, 7%, 10%, 12%, 15%, 17%, 20%, 25%, 27%, 30%, 32% or 35% of the number of HSPCs. In some embodiments, the number of naïve conventional αβ-T cells in a composition can be about 2%, 5%, 7%, 10%, 12%, 15%, 17%, 20%, 25%, 27%, 30%, 32% or 35% of the number of HSPCs. In some embodiments, the number of naïve conventional αβ-T cells in a composition can be about 2% to about 7%, about 2% to about 10%, about 2% to about 15%, about 2% to about 20%, about 2% to about 25%, about 2% to about 30%, about 2% to about 35%, about 7% to about 10%, about 7% to about 15%, about 7% to about 20%, about 7% to about 25%, about 7% to about 30%, about 7% to about 35%, about 10% to about 15%, about 10% to about 20%, about 10% to about 25%, about 10% to about 30%, about 10% to about 35%, about 15% to about 20%, about 15% to about 25%, about 15% to about 30%, about 15% to about 35%, about 20% to about 25%, about 20% to about 30%, about 20% to about 35%, about 25% to about 30%, about 25% to about 35%, or about 30% to about 35% of the number of HSPCs.

In some embodiments, the number of naïve conventional αβ-T cells in a composition can be less than about 0.1%, 1%, 2%, 5%, 7%, 10%, 12%, 15%, 17%, 20%, 22% or 25% of the number of Tmem cells. In some embodiments, the number of naïve conventional αβ-T cells in a composition can be at most about 20%. In some embodiments, the number of naïve conventional αβ-T cells in a composition can be about 0.1% to about 2%, about 0.1% to about 5%, about 0.1% to about 10%, about 0.1% to about 15%, about 0.1% to about 20%, about 2% to about 5%, about 2% to about 10%, about 2% to about 15%, about 2% to about 20%, about 5% to about 10%, about 5% to about 15%, about 5% to about 20%, about 10% to about 15%, about 10% to about 20%, or about 15% to about 20% of the number of Tmem cells.

In some embodiments, the number of naïve conventional αβ-T cells in a composition can be less than about 0.05%, 0.5%, 1%, 2%, 5%, 7%, 10%, 12%, 15%, 17%, 20%, 22%, 25% or 30% of the number of Treg cells. In some embodiments, the number of naïve conventional αβ-T cells in a composition can be about 0.05% to about 1%, about 0.05% to about 5%, about 0.05% to about 10%, about 0.05% to about 15%, about 0.05% to about 20%, about 0.05% to about 30%, about 1% to about 5%, about 1% to about 10%, about 1% to about 15%, about 1% to about 20%, about 1% to about 30%, about 5% to about 10%, about 5% to about 15%, about 5% to about 20%, about 5% to about 30%, about 10% to about 15%, about 10% to about 20%, about 10% to about 30%, about 15% to about 20%, about 15% to about 30%, or about 20% to about 30% of the number of Treg cells.

In some embodiments, the number of naïve conventional αβ-T cells in a composition can be less than about 1%, 10%, 20%, 50%, 70%, 80% or 90% of the number of iNKT cells. In some embodiments, the number of naïve conventional αβ-T cells in a composition can be about 1% to about 10%, about 1% to about 20%, about 1% to about 50%, about 1% to about 70%, about 1% to about 80%, about 1% to about 90%, about 10% to about 20%, about 10% to about 50%, about 10% to about 70%, about 10% to about 80%, about 10% to about 90%, about 20% to about 50%, about 20% to about 70%, about 20% to about 80%, about 20% to about 90%, about 50% to about 70%, about 50% to about 80%, about 50% to about 90%, about 70% to about 80%, about 70% to about 90%, or about 80% to about 90% of the number of iNKT cells.

In certain embodiments, the population of therapeutic cells comprises 10% to 65% HSPC. In certain embodiments, the population of therapeutic cells comprises 2% to 20% Treg. In certain embodiments, the population of therapeutic cells comprises 25% to 90% Tmem. In certain embodiments, the population of therapeutic cells comprises less than 2% naïve conventional αβ-T cells. In certain embodiments, the population of therapeutic cells comprises: 10% to 65% HSPC; 2% to 20% Treg; 25% to 90% Tmem; and less than 2% naïve conventional αβ-T cells. In some embodiments, the population of Treg comprises 2% to 5%, 2% to 10%, 2% to 20%, 2% to 30%, 2% to 40%, 2% to 50%, 5% to 10%, 5% to 20%, 5% to 30%, 5% to 40%, 5% to 50%, 10% to 20%, 10% to 30%, 10% to 40%, 10% to 50%, 15% to 20%, 15% to 30%, 15% to 40%, or 15% to 50% naïve Treg. In some embodiments, the population of Treg comprises 75% to 95% memory Treg. In some embodiments, the population of naïve T cells comprises 0.1% to 10% $T_{SCM}$. In some embodiments, the population of Tmem comprises 0% to 99% $T_{CM}$. In some embodiments, the population of Tmem comprises 0% to 99% $T_{EM}$. In certain embodiments, the population further comprises 0.01% to 5%, 0.05% to 5%, 0.1% to 5%, 0.5% to 5%, 1% to 5%, 0.01% to 1.5%, 0.05% to 1.5%, 0.1% to 1.5%, 0.5% to 1.5%, or 1% to 1.5% iNKT.

In any of the embodiments disclosed herein, the cell population can be provided by processing a sample from one or more tissue harvests. In some embodiments, a the sample or tissue harvest is from a single donor. The one or more tissue harvests can be from one or more donors. For example, the tissue harvest can be from an HLA matched sibling donor, an HLA matched unrelated donor, a partially matched unrelated donor, a haploidentical related donor, autologous donor, a full HLA mismatch allogeneic donor, a pool of donors, or any combination thereof.

In any of the embodiments disclosed herein, the cell population can be a formulation for administration to a subject. In some cases, cell populations may be formulated using excipients. In some embodiments, the cells are formulated for infusion or injection. The excipients can comprise Normosol-R and human serum. The human serum can be 0.2% of the total formulation. The human serum can be 0.5% of the total formulation. The human serum can be 1% of the total formulation. The human serum can be 2% of the total formulation. In addition, the formulation can comprise a pH buffer, such as 0.1 mM-100 mM phosphate pH 6.0-9.0, 0.1-100 mM HEPES pH 6.0-9.0, 0.1 mM-100 mM bicarbonate pH 6.0-9.0, 0.1 mM-100 mM citrate pH 6.0-9.0, 0.1-100 mM acetate pH 4.0-8.0 or any combination thereof. The formulation can comprise electrolytes, such as 5 mM-400 mM NaCl, 0.5 mM-50 mM KCl, 0.05 mM-50 mM CaCl2, 0.05 mM-50 mM MgCl2, 0.05 mM-50 mM LiCl2, 0.05 mM-50 mM MnCl2, or any combination thereof. The formulation can comprise an energy source, such as 0.1 mM-100 mM glucose, 0.1 mM-100 mM pyruvate, 0.1 mM-100 mM fructose, 0.1-100 mM sucrose, 0.1-50 mM glycerol, 0.1 mM-100 mM gluconolactone, 0.1-100 mM gluconate or any combination thereof. The formulation can comprise an anti-oxidant, such as 0.05-10 mM glutathione (reduced), 0.05-10 mM glutathione (oxidized), 0.001 mM-10 mM β-mercaptoethanol, 0.001 mM-10 mM dithiothreitol, 0.01-100 mM ascorbate, 0.001-10 mM tris(2-carboxyethyl)phosphine, or any combination thereof. The formulation can comprise a stabilizer, such as 0.01%-10% human serum albumin, 0.01%-10% bovine serum albumin, 0.1%-99% human serum, 0.1%-99% fetal bovine serum, 0.01%-10% IgG, 0.1%-10% immunoglobin, 0.06%-60% trehalose, or molecular polymers like 0.1%-20% polyethylene glycocol (MW 200-20,000,000), or any combination thereof.

In some embodiments disclosed herein, the cell population formulated for administration to a subject based on the weight of the subject (e.g., number of cells/kg of subject weight). The cell population may be formulated as a pharmaceutical composition. In some embodiments, the pharmaceutical composition comprises a unit dose of a cellular graft (e.g. the cell population), wherein each unit dose of the cellular graft comprises populations of therapeutic cells for each kilogram (kg) of body weight of a subject receiving the cellular graft. In some embodiments, the population or unit dose of cells comprises about $1\times10^6$ HSPCs to about $20\times10^6$ HSPCs per kg of the subject. In some embodiments, the population or unit dose of cells comprises at least about $1\times10^6$ HSPCs per kg of the subject. In some embodiments, the population or unit dose of cells comprises at most about $20\times10^6$ HSPCs per kg of the subject. In some embodiments, the population or unit dose comprises a range of HSPC cells from about $0.5\times10^6$ to $50\times10^6$, $1.0\times10^6$ to $20\times10^6$, or $2.0\times10^6$ to $10\times10^6$ cells/kg of subject weight.

In some embodiments, the population or unit dose of cells comprises about $1\times10^6$ HSPCs to about $2\times10^6$ HSPCs, about $1\times10^6$ HSPCs to about $5\times10^6$ HSPCs, about $1\times10^6$ HSPCs to about $7\times10^6$ HSPCs, about $1\times10^6$ HSPCs to about $10\times10^6$ HSPCs, about $1\times10^6$ HSPCs to about $15\times10^6$ HSPCs, about $1\times10^6$ HSPCs to about $20\times10^6$ HSPCs, about $2\times10^6$ HSPCs to about $5\times10^6$ HSPCs, about $2\times10^6$ HSPCs to about $7\times10^6$ HSPCs, about $2\times10^6$ HSPCs to about $10\times10^6$ HSPCs, about $2\times10^6$ HSPCs to about $15\times10^6$ HSPCs, about $2\times10^6$ HSPCs to about $20\times10^6$ HSPCs, about $5\times10^6$ HSPCs to about $7\times10^6$ HSPCs, about $5\times10^6$ HSPCs to about $10\times10^6$ HSPCs, about $5\times10^6$ HSPCs to about $15\times10^6$ HSPCs, about $5\times10^6$ HSPCs to about $20\times10^6$ HSPCs, about $7\times10^6$ HSPCs to about $10\times10^6$ HSPCs, about $7\times10^6$ HSPCs to about $15\times10^6$ HSPCs, about $7\times10^6$ HSPCs to about $20\times10^6$ HSPCs, about $10\times10^6$ HSPCs to about $15\times10^6$ HSPCs, about $10\times10^6$ HSPCs to about $20\times10^6$ HSPCs, or about $15\times10^6$ HSPCs to about $20\times10^6$ HSPCs per kg of the subject. In some embodiments, the population of cells comprises about $1\times10^6$ HSPCs, about $2\times10^6$ HSPCs, about $5\times10^6$ HSPCs, about $7\times10^6$ HSPCs, about $10\times10^6$ HSPCs, about $15\times10^6$ HSPCs, or about $20\times10^6$ HSPCs per kg of the subject.

In some embodiments, the population or unit dose of cells comprises about $1\times10^6$ Tmem cells to about $100\times10^6$ Tmem cells per kg of the subject. In some embodiments, the population or unit dose of cells comprises at least about $1\times10^6$ Tmem cells per kg of the subject. In some embodiments, the population or unit dose of cells comprises at most about $100\times10^6$ Tmem cells per kg of the subject. In some embodiments, the population or unit dose of cells comprises about $1\times10^6$ Tmem cells to about $10\times10^6$ Tmem cells, about $1\times10^6$ Tmem cells to about $20\times10^6$ Tmem cells, about $1\times10^6$ Tmem cells to about $50\times10^6$ Tmem cells, about $1\times10^6$ Tmem cells to about $75\times10^6$ Tmem cells, about $1\times10^6$ Tmem cells to about $100\times10^6$ Tmem cells, about $10\times10^6$ Tmem cells to about $20\times10^6$ Tmem cells, about $10\times10^6$ Tmem cells to about $50\times10^6$ Tmem cells, about $10\times10^6$ Tmem cells to about $75\times10^6$ Tmem cells, about $10\times10^6$ Tmem cells to about $100\times10^6$ Tmem cells, about $20\times10^6$ Tmem cells to about $50\times10^6$ Tmem cells, about $20\times10^6$ Tmem cells to about $75\times10^6$ Tmem cells, about $20\times10^6$ Tmem cells to about $100\times10^6$ Tmem cells, about $50\times10^6$ Tmem cells to about $75\times10^6$ Tmem cells, about $50\times10^6$ Tmem cells to about $100\times10^6$ Tmem cells, or about $75\times10^6$ Tmem cells to about $100\times10^6$ Tmem cells per kg of the subject. In some embodiments, the population or unit dose of cells comprises about $1\times10^6$ Tmem cells, about $10\times10^6$ Tmem cells, about $20\times10^6$ Tmem cells, about $50\times10^6$ Tmem cells, about $75\times10^6$ Tmem cells, or about $100\times10^6$ Tmem cells per kg of the subject.

In some embodiments, the population or unit dose of cells comprises about $0.5\times10^6$ Treg cells to about $2.5\times10^6$ Treg cells per kg of the subject. In some embodiments, the population or unit dose of cells comprises at least about $0.5\times10^6$ Treg cells per kg of the subject. In some embodiments, the population or unit dose of cells comprises at most about $2.5\times10^6$ Treg cells per kg of the subject. In some embodiments, the population or unit dose of cells comprises about $0.5\times10^6$ Treg cells to about $1\times10^6$ Treg cells, about $0.5\times10^6$ Treg cells to about $1.5\times10^6$ Treg cells, about $0.5\times$ $10^6$ Treg cells to about $2\times10^6$ Treg cells, about $0.5\times10^6$ Treg cells to about $2.5\times10^6$ Treg cells, about $1\times10^6$ Treg cells to about $1.5\times10^6$ Treg cells, about $1\times10^6$ Treg cells to about $2\times10^6$ Treg cells, about $1\times10^6$ Treg cells to about $2.5\times10^6$ Treg cells, about $1.5\times10^6$ Treg cells to about $2\times10^6$ Treg cells, about $1.5\times10^6$ Treg cells to about $2.5\times10^6$ Treg cells, or about $2\times10^6$ Treg cells to about $2.5\times10^6$ Treg cells per kg of the subject. In some embodiments, the population or unit dose of cells comprises about $0.5\times10^6$ Treg cells, about $1\times10^6$ Treg cells, about $1.5\times10^6$ Treg cells, about $2\times10^6$ Treg cells, or about $2.5\times10^6$ Treg cells per kg of the subject. In some embodiments, the population or unit dose of cells comprises a range of naïve Treg from about $0.1\times10^6$ to about $500\times10^6$, about $0.2\times10^6$ to about $500\times10^6$, about $0.3\times10^6$ to about $500\times10^6$, about $0.4\times10^6$ to about $500\times10^6$, about $0.5\times10^6$ to about $500\times10^6$, about $0.6\times10^6$ to about $500\times10^6$, about $0.7\times10^6$ to about $500\times10^6$, about $0.8\times10^6$ to about $500\times10^6$, about $0.9\times10^6$ to about $500\times10^6$, or about $1\times10^6$ to about $500\times10^6$ cells/kg of subject weight. In some embodiments, the population or unit dose of cells comprises a range of Memory Treg from $0.005\times10^6$ to $500\times10^6$ cells/kg of subject weight.

In some embodiments, the population or unit dose of cells comprises a range of iNKT cells from $0.5\times10^3$ to $2000\times10^3$ cells/kg of subject weight, $0.5\times10^3$ to $1\times10^7$ cells/kg of subject weight, or $1.0\times10^4$ to $2.5\times10^6$ cells/kg of subject weight. In some embodiments, the population or unit dose of cells comprises about $0.01\times10^6$ iNKT cells to about $3\times10^6$ iNKT cells per kg of the subject. In some embodiments, the population or unit dose of cells comprises at least about $0.01\times10^6$ iNKT cells per kg of the subject. In some embodiments, the population or unit dose of cells comprises at most about $3\times10^6$ iNKT cells per kg of the subject. In some embodiments, the population or unit dose of cells comprises about $0.01\times10^6$ iNKT cells to about $0.1\times10^6$ iNKT cells, about $0.01\times10^6$ iNKT cells to about $1\times10^6$ iNKT cells, about $0.01\times10^6$ iNKT cells to about $1.5\times10^6$ iNKT cells, about $0.01\times10^6$ iNKT cells to about $2\times10^6$ iNKT cells, about $0.01\times10^6$ iNKT cells to about $3\times10^6$ iNKT cells, about $0.1\times10^6$ iNKT cells to about $1\times10^6$ iNKT cells, about $0.1\times10^6$ iNKT cells to about $1.5\times10^6$ iNKT cells, about $0.1\times10^6$ iNKT cells to about $2\times10^6$ iNKT cells, about $0.1\times10^6$ iNKT cells to about $3\times10^6$ iNKT cells, about $1\times10^6$ iNKT cells to about $1.5\times10^6$ iNKT cells, about $1\times10^6$ iNKT cells to about $2\times10^6$ iNKT cells, about $1\times10^6$ iNKT cells to about $3\times10^6$ iNKT cells, about $1.5\times10^6$ iNKT cells to about $2\times10^6$ iNKT cells, about $1.5\times10^6$ iNKT cells to about $3\times10^6$ iNKT cells, or about $2\times10^6$ iNKT cells to about $3\times10^6$ iNKT cells per kg of the subject. In some embodiments, the population or unit dose of cells comprises about $0.01\times10^6$ iNKT cells, about $0.1\times10^6$ iNKT cells, about $1\times10^6$ iNKT cells, about $1.5\times10^6$ iNKT cells, about $2\times10^6$ iNKT cells, or about $3\times10^6$ iNKT cells per kg of the subject.

In some embodiments, the population or unit dose of cells comprises a range of naïve conventional αβ-T cells less than $1\times10^6$ cells/kg of subject weight. In some embodiments, the population or unit dose of cells comprises a range of naïve conventional αβ-T cells less than $3\times10^5$ cells/kg of subject weight. In some embodiments, the population or unit dose of cells comprises a range of naïve conventional αβ-T cells less than $7.5\times10^4$ cells/kg of subject weight, less than $5\times10^4$ cells/kg, less than $1\times10^4$ cells/kg, less than $0.5\times10^4$ cells/kg, or less than $1\times10^3$ cells/kg of subject weight.

In some embodiments, the populations of therapeutic cells of each unit dose comprise: $1.0\times10^6$ to $50\times10^6$ hematopoietic stem/progenitor cells (HSPC), $0.1\times10^6$ to $1000\times10^6$ memory T cells (Tmem), $0.1\times10^6$ to $1000\times10^6$ regulatory T cells (Treg), and of less than $3\times10^5$ naïve conventional αβ-T. In some embodiments, the populations of therapeutic cells of each unit dose comprise: $3.0\times10^6$ to $50\times10^6$ hematopoietic stem/progenitor cells (HSPC), $0.3\times10^6$ to $1000\times10^6$ memory T cells (Tmem), $0.5\times10^6$ to $1000\times10^6$ regulatory T cells (Treg), and of less than $3\times10^5$ naïve conventional αβ-T. In some embodiments, the populations of therapeutic cells of each unit dose comprise: $1.0\times10^6$ to $50\times10^6$ hematopoietic stem/progenitor cells (HSPC), $0.3\times10^6$ to $1000\times10^6$ memory T cells (Tmem), $0.5\times10^6$ to $1000\times10^6$ regulatory T cells (Treg), and less than $3\times10^5$ naïve conventional αβ-T.

In any one of the embodiments disclosed herein, the HSPC can be provided by a donor that is haploidentical to the subject. In some embodiments, the Treg, Tmem, iNKT, or any combination thereof are provided by a donor that is an HLA matched sibling donor or an HLA matched unrelated donor or partially matched HLA unrelated donor. In some embodiments, the HSPC are provided by a donor that is haploidentical to the subject and the Treg, Tmem, iNKT, or any combination thereof are provided by a donor that is an HLA matched sibling donor or an HLA matched unrelated donor.

Methods of Treatment

The present disclosure provides methods of performing cellular graft therapy in a subject having a disease, condition, or disorder comprising: administering any of the therapeutic cellular graft compositions described herein to the subject. For example, a therapeutic composition comprising cells can be infused to a subject in need thereof.

Subjects that can be treated include subjects afflicted with leukemia, lymphoma, chronic infection, or autoimmune disease, malignant or nonmalignant blood disease, AML, ALL, CML, CLL, Multiple Myeloma, Hodgkin's lymphoma, non-Hodgkin's lymphoma, MDS, Lymphoproliferative diseases, type 1 diabetes, inborn errors of metabolism, genetic disease, severe combined immunodeficiency, sickle cell anemia, beta-thallasemia, multiple sclerosis, solid organ transplantation, Crohn's disease, ulcerative colitis, lupus, Hemophagocytic lymphohistiocytosis, glycogen storage disorders, breast cancer, other solid tumors, leukodystrophies, mucopolysaccharidosis or any other disease that would benefit from a HSPC transplant. In some embodiments, the subject is afflicted with ALL or AML in relapse or with primary refractory ALL or AML with less than 10% blasts. In some embodiments, the subject is afflicted with high risk AML in ≥CR1 or with minimal residual disease positivity. In some embodiments, the subject is afflicted with high risk ALL in >=CR1 or with minimal residual disease positivity. In some embodiments, the subject is afflicted with high risk CML. In some embodiments, the subject is afflicted with high risk myeloproliferative disorders. In some embodiments, the subject is afflicted with relapsed non-Hodgkin lymphoma responsive to therapy. In some embodiments, the subject is afflicted with MDS with blast count less than 10% blasts at the time of transplantation. In certain embodiments, the subject has one or more of the following characteristics: age 18-65, Karnofsky score ≥60 or ECOG≤2, HCT-Comorbidity Index ≤4, Creatinine <1.5 mg/dL, Cardiac ejection fraction >45%, DLCO corrected >60% of predicted, total bilirubin <3 times upper limit of normal (ULN) (unless attributed to Gilbert syndrome), AST and ALT<3 times ULN, not pregnant or nursing, HIV negative, and no co-existing disease that would limit life expectancy to <6 months. In certain embodiments, the subject has one or more of the following characteristics: age patients 0-3, 3-6, 6-12, 12-14, 12-18, 18-65, 65-70, 70-75, 75-80, 80-90 or older, or any range in between, Karnofsky score ≥60 or ≥80, or ECOG≤2, HCT-Comorbidity Index ≤4, Creatinine <1.5 mg/dL, Cardiac ejection fraction >45%, DLCO corrected >60% of predicted, total bilirubin <3 times upper limit or <1.5 times upper limit of normal (ULN) (unless attributed to Gilbert syndrome), AST and ALT<3 times or <1.5 times the ULN, not pregnant or nursing, HIV negative, and no coexisting disease that would limit life expectancy to <6 months.

Therapeutic cellular compositions described herein can be administered in place of traditional HCT. Exemplary therapeutic cellular compositions are compatible with reduced intensity conditioning (RIC) and myeloablative (MA) regimens. Because of the reduced risk of GVHD, MA conditioning may be used in place of RIC for some patients, especially those with underlying malignancies. Because the therapeutic cellular compositions disclosed here have decreased GVHD, the alloreactivity may be beneficial in the case of multiple myeloma, where GVHD risks outweigh alloreactivity and auto transplant is clinically used currently. Non-malignant conditions are likely to benefit from increased immune reconstitution and therefore lower rates of infection and higher rates of engraftment and durable chimerism.

Therapeutic cellular compositions described herein are administered to subjects in accordance with known techniques, or variations thereof that will be apparent to those skilled in the art.

An "effective amount" or "therapeutically effective amount" refers to that amount of a composition described herein which, when administered to a subject (e.g., human), is sufficient to aid in treating a disease. The amount of a composition that constitutes a "therapeutically effective amount" will vary depending on the cell preparations, the condition and its severity, the manner of administration, and the age of the subject to be treated, but can be determined routinely by one of ordinary skill in the art having regard to his own knowledge and to this disclosure. When referring to an individual active ingredient or composition, administered alone, a therapeutically effective dose refers to that ingredient or composition alone. When referring to a combination, a therapeutically effective dose refers to combined amounts of the active ingredients, compositions or both that result in the therapeutic effect, whether administered serially, concurrently or simultaneously.

In some embodiments, the HSPC cells are administered at a concentration of $CD34^+$ cells $1.0 \times 10^6$ to $50 \times 10^6$ cells/kg of subject weight, $1.0 \times 10^6$ to $20 \times 10^6$ cells/kg of subject weight, or $2.0 \times 10^6$ to $10 \times 10^6$ cells/kg of subject weight. In some embodiments, the HSPC cells are administered at a concentration of about $1 \times 10^6$ HSPCs to about $20 \times 10^6$ HSPCs per kg of the subject. In some embodiments, the HSPC cells are administered at a concentration of at least about $1 \times 10^6$ HSPCs per kg of the subject. In some embodiments, the HSPC cells are administered at a concentration of at most about $20 \times 10^6$ HSPCs per kg of the subject. In some embodiments, the HSPC cells are administered at a concentration of about $1 \times 10^6$ HSPCs to about $2 \times 10^6$ HSPCs, about $1 \times 10^6$ HSPCs to about $5 \times 10^6$ HSPCs, about $1 \times 10^6$ HSPCs to about $7 \times 10^6$ HSPCs, about $1 \times 10^6$ HSPCs to about $10 \times 10^6$ HSPCs, about $1 \times 10^6$ HSPCs to about $15 \times 10^6$ HSPCs, about $1 \times 10^6$ HSPCs to about $20 \times 10^6$ HSPCs, about $2 \times 10^6$ HSPCs to about $5 \times 10^6$ HSPCs, about $2 \times 10^6$ HSPCs to about $7 \times 10^6$ HSPCs, about $2 \times 10^6$ HSPCs to about $10 \times 10^6$ HSPCs, about $2 \times 10^6$ HSPCs to about $15 \times 10^6$ HSPCs, about $2 \times 10^6$ HSPCs to about $20 \times 10^6$ HSPCs, about $5 \times 10^6$ HSPCs to about $7 \times 10^6$ HSPCs, about $5 \times 10^6$ HSPCs to about $10 \times 10^6$ HSPCs, about $5 \times 10^6$ HSPCs to about $15 \times 10^6$ HSPCs, about $5 \times 10^6$ HSPCs to about $20 \times 10^6$ HSPCs, about $7 \times 10^6$ HSPCs to about $10 \times 10^6$ HSPCs, about $7 \times 10^6$ HSPCs to about $15 \times 10^6$ HSPCs, about $7 \times 10^6$ HSPCs to about $20 \times 10^6$ HSPCs, about $10 \times 10^6$ HSPCs to about $15 \times 10^6$ HSPCs, about $10 \times 10^6$ HSPCs to about $20 \times 10^6$ HSPCs, or about $15 \times 10^6$ HSPCs to about $20 \times 10^6$ HSPCs per kg of the subject. In some embodiments, the HSPC cells are administered at a concentration of about $1 \times 10^6$ HSPCs, about $2 \times 10^6$ HSPCs, about $5 \times 10^6$ HSPCs, about $7 \times 10^6$ HSPCs, about $10 \times 10^6$ HSPCs, about $15 \times 10^6$ HSPCs, or about $20 \times 10^6$ HSPCs per kg of the subject.

In some embodiments, the Tmem are administered at a concentration of $0.1 \times 10^6$ to $1000 \times 10^6$ cells/kg of subject weight, $1.0 \times 10^6$ to $250 \times 10^6$ cells/kg of subject weight, or $2.9 \times 10^6$ to $10.1 \times 10^6$ cells/kg of subject weight, $10.1 \times 10^6$ to $30.1 \times 10^6$ cells/kg of subject weight, $30.1 \times 10^6$ to $101 \times 10^6$ cells/kg of subject weight, $1.0 \times 10^6$ to $100 \times 10^6$ cells/kg of subject weight. In some embodiments, the Tmem cells are administered at a concentration of about $1 \times 10^6$ Tmem cells to about $100 \times 10^6$ Tmem cells per kg of the subject. In some embodiments, the Tmem cells are administered at a concentration of at least about $1 \times 10^6$ Tmem cells per kg of the subject. In some embodiments, the Tmem cells are administered at a concentration of at most about $100 \times 10^6$ Tmem cells per kg of the subject. In some embodiments, the Tmem cells are administered at a concentration of about $1 \times 10^6$ Tmem cells to about $10 \times 10^6$ Tmem cells, about $1 \times 10^6$ Tmem cells to about $20 \times 10^6$ Tmem cells, about $1 \times 10^6$ Tmem cells to about $50 \times 10^6$ Tmem cells, about $1 \times 10^6$ Tmem cells to about $75 \times 10^6$ Tmem cells, about $1 \times 10^6$ Tmem cells to about $100 \times 10^6$ Tmem cells, about $10 \times 10^6$ Tmem cells to about $20 \times 10^6$ Tmem cells, about $10 \times 10^6$ Tmem cells to about $50 \times 10^6$ Tmem cells, about $10 \times 10^6$ Tmem cells to about $75 \times 10^6$ Tmem cells, about $10 \times 10^6$ Tmem cells to about $100 \times 10^6$ Tmem cells, about $20 \times 10^6$ Tmem cells to about $50 \times 10^6$ Tmem cells, about $20 \times 10^6$ Tmem cells to about $75 \times 10^6$ Tmem cells, about $20 \times 10^6$ Tmem cells to about $100 \times 10^6$ Tmem cells, about $50 \times 10^6$ Tmem cells to about $75 \times 10^6$ Tmem cells, about $50 \times 10^6$ Tmem cells to about $100 \times 10^6$ Tmem cells, or about $75 \times 10^6$ Tmem cells to about $100 \times 10^6$ Tmem cells per kg of the subject. In some embodiments, the Tmem cells are administered at a concentration of about $1 \times 10^6$ Tmem cells, about $10 \times 10^6$ Tmem cells, about $20 \times 10^6$ Tmem cells, about $50 \times 10^6$ Tmem cells, about $75 \times 10^6$ Tmem cells, or about $100 \times 10^6$ Tmem cells per kg of the subject.

In some embodiments, the Treg are administered at a concentration of $0.1 \times 10^6$ to $1000 \times 10^6$ cells/kg of subject weight, $0.1 \times 10^6$ to $5 \times 10^6$ cells/kg of subject weight, or $0.5 \times 10^6$ to $2.5 \times 10^6$ cells/kg of subject weight. In some embodiments, the Treg are administered at a concentration of about $0.5 \times 10^6$ Treg cells to about $2.5 \times 10^6$ Treg cells per kg of the subject. In some embodiments, the Treg are administered at a concentration of at least about $0.5 \times 10^6$ Treg cells per kg of the subject. In some embodiments, the Treg are administered at a concentration of at most about $2.5 \times 10^6$ Treg cells per kg of the subject. In some embodiments, the Treg are administered at a concentration of about $0.5 \times 10^6$ Treg cells to about $1 \times 10^6$ Treg cells, about $0.5 \times 10^6$ Treg cells to about $1.5 \times 10^6$ Treg cells, about $0.5 \times 10^6$ Treg cells to about $2 \times 10^6$ Treg cells, about $0.5 \times 10^6$ Treg cells to about $2.5 \times 10^6$ Treg cells, about $1 \times 10^6$ Treg cells to about $1.5 \times 10^6$ Treg cells, about $1 \times 10^6$ Treg cells to about $2 \times 10^6$ Treg cells, about $1 \times 10^6$ Treg cells to about $2.5 \times 10^6$ Treg cells, about $1.5 \times 10^6$ Treg cells to about $2 \times 10^6$ Treg cells, about $1.5 \times 10^6$ Treg cells to about $2.5 \times 10^6$ Treg cells, or about $2 \times 10^6$ Treg cells to about $2.5 \times 10^6$ Treg cells per kg of the subject. In some embodiments, the Treg are administered at a concentration of about $0.5\times10^6$ Treg cells, about $1\times10^6$ Treg cells, about $1.5\times10^6$ Treg cells, about $2\times10^6$ Treg cells, or about $2.5\times10^6$ Treg cells per kg of the subject.

In some embodiments, the naïve Treg are administered at a concentration of about $0.1\times10^6$ to about $500\times10^6$, about $0.2\times10^6$ to about $500\times10^6$, about $0.3\times10^6$ to about $500\times10^6$, about $0.4\times10^6$ to about $500\times10^6$, about $0.5\times10^6$ to about $500\times10^6$, about $0.6\times10^6$ to about $500\times10^6$, about $0.7\times10^6$ to about $500\times10^6$, about $0.8\times10^6$ to about $500\times10^6$, about $0.9\times10^6$ to about $500\times10^6$, or about $1\times10^6$ to about $500\times10^6$ cells/kg of subject weight In some embodiments, the memory Treg are administered at a concentration of $0.005\times10^6$ to $500\times10^6$ cells/kg of subject weight.

In some embodiments, the iNKT cells are administered at a concentration of $0.5\times10^2$ to $2000\times10^3$ cells/kg of subject weight, $0.5\times10^2$ to $1\times10^4$ cells/kg of subject weight, $0.5\times10^3$ to $1\times10^5$ cells/kg of subject weight, $0.5\times10^4$ to $1\times10^6$ cells/kg of subject weight, $0.5\times10^5$ to $1\times10^7$ cells/kg of subject weight $0.5\times10^2$ to $1\times10^7$ cells/kg of subject weight, or $1.0\times10^4$ to $2.5\times10^6$ cells/kg of subject weight. In some embodiments, the iNKT cells are administered at a concentration of about $0.01\times10^6$ iNKT cells to about $3\times10^6$ iNKT cells per kg of the subject. In some embodiments, the iNKT cells are administered at a concentration of at least about $0.01\times10^6$ iNKT cells per kg of the subject. In some embodiments, the iNKT cells are administered at a concentration of at most about $3\times10^6$ iNKT cells per kg of the subject. In some embodiments, the iNKT cells are administered at a concentration of about $0.01\times10^6$ iNKT cells to about $0.1\times10^6$ iNKT cells, about $0.01\times10^6$ iNKT cells to about $1\times10^6$ iNKT cells, about $0.01\times10^6$ iNKT cells to about $1.5\times10^6$ iNKT cells, about $0.01\times10^6$ iNKT cells to about $2\times10^6$ iNKT cells, about $0.01\times10^6$ iNKT cells to about $3\times10^6$ iNKT cells, about $0.1\times10^6$ iNKT cells to about $1\times10^6$ iNKT cells, about $0.1\times10^6$ iNKT cells to about $1.5\times10^6$ iNKT cells, about $0.1\times10^6$ iNKT cells to about $2\times10^6$ iNKT cells, about $0.1\times10^6$ iNKT cells to about $3\times10^6$ iNKT cells, about $1\times10^6$ iNKT cells to about $1.5\times10^6$ iNKT cells, about $1\times10^6$ iNKT cells to about $2\times10^6$ iNKT cells, about $1\times10^6$ iNKT cells to about $3\times10^6$ iNKT cells, about $1.5\times10^6$ iNKT cells to about $2\times10^6$ iNKT cells, about $1.5\times10^6$ iNKT cells to about $3\times10^6$ iNKT cells, or about $2\times10^6$ iNKT cells to about $3\times10^6$ iNKT cells per kg of the subject. In some embodiments, the iNKT cells are administered at a concentration of about $0.01\times10^6$ iNKT cells, about $0.1\times10^6$ iNKT cells, about $1\times10^6$ iNKT cells, about $1.5\times10^6$ iNKT cells, about $2\times10^6$ iNKT cells, or about $3\times10^6$ iNKT cells per kg of the subject.

In some embodiments, the administered cells comprise naïve conventional αβ-T cells at less than $3\times10^5$ cells/kg of subject weight. In some embodiments, the administered cells comprise naïve conventional αβ-T cells less than $2\times10^5$ cells/kg of subject weight, less than $1\times10^5$ cells/kg of subject, weight less than $7.5\times10^4$ cells/kg, less than $5\times10^4$ cells/kg, less than $1\times10^4$ cells/kg, less than $0.5\times10^4$ cells/kg or less than $1\times10^3$ cells/kg of subject weight.

As further discussed in the Examples, the purity of the therapeutic cellular composition can be important to the clinical outcome of the treatment. For example, processing of cellular fractions that may include naïve Tcon contaminating cells with therapeutic cells using method that results in low purity can impair the therapeutic efficacy by resulting higher levels of GVHD, acute GVHD grades 3-4, steroid resistant acute GVHD grades 3-4, chronic GVHD, graft failure, graft rejection, serious infection, organ failure, VOD/SOS, and relapse compared to therapeutic cellular compositions prepared using high fidelity sorting techniques (e.g. FACS).

Without wishing to be bound by theory, it is believed that the therapeutic cellular compositions disclosed herein provide a superior therapeutic benefit in myeloablative transplant procedures because the Treg, Tmem, and iNKT cells that are provided with the HSPCs result in early rescue of the subject's immune system compared to traditional myeloablative HSPC transplant procedures. When a subject receives a traditional myeloablative HSPC transplant, the immune system can take up to a year to begin to significantly recover and provide protective immunity. In comparison, it is thought the introduction of Treg, Tmem, or iNKT cells with HSPCs in the presently disclosed therapeutic composition provide a supplement to the subject's ablated immune cells. These supplemented cells begin to provide significant immune function shortly after administration. Therefore, the presently disclosed therapeutic cellular composition provides a superior therapeutic benefit compared to traditional HSPC transplants. It is also believed that regulatory T cells may assist in engraftment and preventing GVHD by suppressing alloreactive T cells in solid tissue. It is also thought that iNKT cells supply Tregs with positive feedback signals to promote a suppressive environment especially in solid tissues. It is also thought that HSPC will reconstitute the blood and immune system of a myeloablated patient, including reconstitution of NK cells, which are further thought to provide a graft versus leukemia effect. It is also thought that the memory T cells provide anti-infection effects and anti-leukemia effects for a limited time (less than 5 years). Because of their limited lifetime, these cells cannot sustain a prolonged graft versus host disease reaction.

In some embodiments, the therapeutic cell populations are administered to the subject as separate pharmaceutical compositions. For example, the enriched HSPC, Tmem, Treg or iNKT cell populations may be administered sequentially. In some embodiments, the therapeutic cell populations are administered in multiple doses. In some cases, a dose of the cell populations may comprise HSPCs. In some cases, a dose of the cell populations may comprise Treg cells. In some cases, a dose of the cell populations may comprise Tmem cells. In some cases, a dose of the cell populations may comprise iNKT cells. In some embodiments, the therapeutic cell populations are administered simultaneously to the subject as a single pharmaceutical composition. The doses may be administered as a course of therapy. A course of therapy my comprise administering a dose to a subject at 1 day, 2 day, 3 day, 4 day, 5 day, 6 day, 7 day intervals. A course of therapy my comprise administering a dose to a subject at 1 week, 2 week, 3 week, or 4 week intervals. A course of therapy my comprise administering a dose to a subject at 1 month, 2 month, 3 month, or 4 month intervals.

In some embodiments, the therapeutic compositions described herein may be administered as separate populations of cells. For instance, a first dose of a therapeutic composition can comprise administering any of a population of HSPCs, a population of Treg cells, or a population of Tmem cells, alone or in any combination. A subsequent dose can then comprise any of the above cell types not present in the first dose. A dose also can comprise iNKT cells. By way of example, a first dose can comprise HSPCs, while a second dose comprises Treg and Tmem cells. Other combinations of doses may also be administered to a subject.

In some embodiments, a complete dose of the therapeutic composition may comprise a plurality of doses. A complete therapeutic composition described herein may be administered in at least 1 dose. A complete therapeutic composition described herein may be administered in at most 30 doses. In some cases, a complete therapeutic composition described herein may be administered in about 2 doses, 5 doses, 10 doses, 15 doses, 20 doses, 25 doses or 30 doses. In some cases, a dose of the complete therapeutic composition may comprise HSPCs, Treg cells, Tmem cells. In some cases, individual doses of the complete therapeutic composition may comprise different cell populations.

In some embodiments, a unit dose may comprise at least $3 \times 10^5$ HSPCs per kg of a subject. In some embodiments, a unit dose may comprise at least $3 \times 10^5$ Treg cells per kg of a subject. In some embodiments, a unit dose may comprise at least $3 \times 10^5$ Tmem cells per kg of a subject. In some embodiments, a unit dose may comprise at least $3 \times 10^5$ iNKT cells per kg of a subject. In some embodiments, a unit dose may comprise less than $3 \times 10^5$ Tcon cells per kg of a subject.

In some embodiments, the complete therapeutic composition may be administered in about 1 day. In some cases, the complete therapeutic composition may be administered in at most 30 days. For instance, a first dose of the therapeutic compositions described herein may be administered in 1 day and a second dose is administered after 10 days. In some cases, the complete therapeutic composition may be administered in about 1 day, 2 days, 5 days, 10 days, 15 days, 20 days or 30 days.

In some embodiments, the cells are isolated from a donor that is an HLA matched sibling donor, an HLA matched unrelated donor, a partially matched unrelated donor, a haploidentical related donor, autologous donor, an HLA unmatched donor, a pool of donors or any combination thereof. In some embodiments, the population of therapeutic cells is allogeneic. In some embodiments, the population of therapeutic cells is autologous. In some embodiments, the population of therapeutic cells is haploidentical. In some embodiments, the population of therapeutic cells is isolated from mobilized peripheral blood, mobilized apheresis product, bone marrow, umbilical cord blood, non-mobilized blood, non-mobilized apheresis product, or any combination thereof.

In some embodiments, the population of therapeutic cells is derived from a single tissue harvest. In some embodiments, the population of therapeutic cells is derived from one or more tissue harvest. In some embodiments, the population of therapeutic cells comprises HSPC provided by at least a first donor and Treg and Tmem provided by at least a second donor. In some embodiments, the population of therapeutic cells comprises iNKT cells provided by at least the second donor. In certain embodiments, the first donor is haploidentical to the subject. In certain embodiments, the second donor is an HLA matched sibling donor or an HLA matched or partially matched unrelated donor.

In some embodiments, the subject has been conditioned with radiation, chemotherapy, recombinant proteins, antibodies, or toxin-conjugated antibodies, or any combination thereof prior to treatment. In some embodiments, the subject is conditioned for cellular graft therapy by first treating the subject with myeloablative therapy. Exemplary myeloablative therapies include chemotherapy or radiotherapy. Myleoablative therapies are thought to provide therapeutic benefit by debulking the tumor. Cancer cells are generally more susceptible to chemotherapy/radiotherapy than many normal cells. However, if tumor-initiating cell survives a course of chemotherapy/radiotherapy, then the subject risks relapse. Therefore, high levels of chemotherapy can help improve the elimination of tumor-initiating populations; however, at these concentrations toxicity occurs against normal cells. Though some of the susceptible normal cells are non-essential, hematopoietic stem cells are killed to a lethal extent by high levels of chemotherapy. Myeloablative regimens eradicate a sufficient amount of HSCs that the patient would otherwise die without a transplant. When HSPCs are infused into the myeloablated subject, the donor cells can rescue the subject and reconstitute the blood and the immune system of the subject for life. In some embodiments, the myeloablative therapy comprises administration of busulfan, cyclophosphamide, TBI, fludarabine, etoposide, or any combination thereof. In some embodiments, the myeloablative therapy comprises administration an anti-cKIT antibody. In some embodiments, the myeloablative therapy comprises administration an antibody drug conjugate. The antibody drug conjugate can be, for example, anti-CD45-saporin or anti-cKit-saporin therapeutic antibodies. In some embodiments, the myeloablative therapy is a reduced intensity conditioning therapy.

In certain embodiments, therapeutic cell populations are administered to the subject as combination therapy comprising immunosuppressive agents. Exemplary immunosuppressive agents include sirolimus, tacrolimus, cyclosporine, mycophenolate, anti-thymocyte globulin, corticosteroids, calcineurin inhibitor, anti-metabolite, such as methotrexate, post-transplant cyclophosphamide or any combination thereof. In some embodiments, the subject is pretreated with only sirolimus or tacrolimus as prophylaxis against GVHD. In some embodiments, the therapeutic cell populations are administered to the subject before an immunosuppressive agent. In some embodiments, the therapeutic cell populations are administered to the subject after an immunosuppressive agent. In some embodiments, the therapeutic cell populations are administered to the subject at the concurrently with an immunosuppressive agent. In some embodiments, the therapeutic cell populations are administered to the subject without an immunosuppressive agent. In some embodiments, the patient receiving a therapeutic cell population is receives immunosuppressive agent for less than 6 months, 5 months, 4 months, 3 months, 2 months, 1 month, 3 weeks, 2 weeks, or 1 week.

In some embodiments, a subject is receiving Bu/Flu and/or Bu/Cy starts Tacrolimus at day +3 at an initial dose of 0.03 mg/kg/day intravenous infusion with a target of 4-8 ng/ml. In some embodiments, a subject is receiving Cy/TBI (Also for TBI/VP-16 or TBI/VP-16/Cy) starts Sirolimus at day +3 at an initial dose of 6 mg loading dose followed by 2 mg daily with a target of 3-8 ng/ml. Should a subject become intolerant of their specific GVHD prophylaxis or other reasons to change are determined by the treating physician then prophylaxis can be altered at the discretion of the treating physician, with the recommendation that Tacrolimus, Sirolimus or Mycophenolate Mofetil be utilized. Should GVHD occur, the appropriate treatment schedule and dose will be initiated. Recipients who develop acute GVHD will be treated at the discretion of the treating physician.

Selection and Sorting of Cell Populations

Prior to formulation or administration of the therapeutic cells, a source(s) of cells is obtained from donor (e.g., peripheral blood mononuclear cells, bone marrow, umbilical cord blood), from which therapeutic cells are enriched or depleted. Methods for enriching or depleting of specific subset cell populations in a mixture of cells are well known in the art. For example, cell populations can be enriched or depleted by density separation, rosetting tetrameric antibody complex mediated enrichment/depletion, magnetic activated cell sorting (MACS), multi-parameter fluorescence based molecular phenotypes such as fluorescence-activated cell sorting (FACS), or any combination thereof. Additional methods of enriching or depleting cell populations are provided, for example, U.S. Provisional Application 62/421,979; U.S. Patent Application Publication No. 2014/0011690; and U.S. Patent Application Publication No. 2016/0245805, which are hereby incorporated by reference in their entirety. Collectively, these methods of enriching or depleting cell populations may be referred to generally herein as "sorting" the cell populations or contacting the cells "under conditions" to form or produce an enriched (+) or depleted (−) cell population.

Accordingly, embodiments of the instant disclosure includes methods for producing a pharmaceutical composition comprising, processing at least one sample to provide: (a) a population of enriched hematopoietic stem/progenitor cells (HSPC); (b) a population of enriched regulatory T cells (Treg); (c) a population of enriched memory T cells (Tmem); and (d) formulating the enriched HSPC, memory T cells, and Treg populations as a pharmaceutical composition suitable for administration to a subject, wherein the populations of (a)-(c) are depleted of naïve conventional αβ-T cells. In some embodiments, the method can further comprise processing the sample to provide a population of enriched iNKT cells.

In some embodiments, the method further comprises processing the sample to provide a population of cells depleted of Lin$^+$ cells. The method can comprise providing a population of enriched naïve Treg, a population of enriched memory Treg, or both. In some embodiments, providing the population of enriched Tmem comprises providing a population of enriched T stem central memory cells ($T_{SCM}$), a population of enriched T central memory cells ($T_{CM}$), a population of enriched T effector memory cells ($T_{EM}$), or any combination thereof. In some embodiments, the method can further comprise processing the sample to provide a population of enriched iNKT cells.

In some embodiments, the population of enriched HSPC comprises at least 50%, 55%, 60%, 65%, 70%, 75%, 80%, 85%, 90%, 91%, 92%, 93%, 94%, 95%, 96%, 97%, 98%, or 99% or more CD34$^+$ HSPC. In some embodiments, the population of cells depleted of Lin$^r$ cells comprises 1%-30% Lin$^r$ cells, preferably less than 1% Lin$^+$ cells. In some embodiments, the population of enriched Treg comprises 20%-99.9% Treg. In some embodiments, the population of enriched Tmem comprises 10%-99.9% Tmem. In some embodiments, the population of enriched iNKT comprises 10%-99.9% iNKT.

In some embodiments, formulating the pharmaceutical composition comprises combining the enriched HSPC population, memory T cells populations, Treg populations, iNKT population, or any combination thereof into a mixed population of enriched cells.

In some embodiments, the mixed population of enriched cells comprises a ratio of HSPC to Tmem comprises a range from 500:1 to 1:1,000, 400:1 to 1:1,000, 300:1 to 1:1,000, 200:1 to 1:1,000, 100:1 to 1:1,000, 50:1 to 1:1,000, 10:1 to 1:1,000, 5:1 to 1:1,000, 4:1 to 1:1,000, 3:1 to 1:1,000, 2:1 to 1:1,000, 1:1 to 1:1,000, 500:1 to 1:900, 500:1 to 1:800, 500:1 to 1:700, 500:1 to 1:600, 500:1 to 1:500, 500:1 to 1:400, 500:1 to 1:300, 500:1 to 1:200, 500:1 to 1:100, 500:1 to 1:50, 500:1 to 1:20, 500:1 to 1:10, 500:1 to 1:9, 500:1 to 1:8, 500:1 to 1:7, 500:1 to 1:6, 500:1 to 1:5, 500:1 to 1:4, 500:1 to 1:3, 500:1 to 1:2, 500:1 to 1:1, 400:1 to 1:900, 300:1 to 1:800, 200:1 to 1:700, 100:1 to 1:600, 50:1 to 1:500, 10:1 to 1:400, 5:1 to 1:300, 4:1 to 1:200, 3:1 to 1:100, 2:1 to 1:50, or 1:1 to 1:20. In some embodiments, the mixed population of enriched cells comprises a ratio of HSPC to Tmem comprises a range from 10:1 to 1:200, 100:1 to 1:2,000, or 1,000:1 to 1:20,000.

In some embodiments, the mixed population of enriched cells comprises a ratio of HSPC to Treg can comprise a range from 20:1 to 1:3, 100:1 to 1:30, or 200:1 to 1:300. The ratio of HSPC to naïve Treg can comprise a range from 1:500 to 100:1, 1:400 to 100:1, 1:300 to 100:1, 1:200 to 100:1, 1:100 to 100:1, 1:50 to 100:1, 1:20 to 100:1, 1:10 to 100:1, 1:5 to 100:1, 1:1 to 100:1, 1:200 to 50:1, 1:200 to 20:1, 1:200 to 10:1, 1:200 to 5:1, 1:100 to 1:1, 40:1 to 1:3, 200:1 to 1:15, or 400:1 to 1:150.

In some embodiments, the mixed population of enriched cells comprises a ratio of HSPC to Memory Treg can comprise a range from 1:500 to 10,000:1, 1:400 to 10,000:1, 1:300 to 10,000:1, 1:200 to 10,000:1, 1:100 to 10,000:1, 1:50 to 10,000:1, 1:20 to 10,000:1, 1:10 to 10,000:1, 1:5 to 10,000:1, 1:1 to 10,000:1, 1:500 to 5,000:1, 1:500 to 1,000:1, 1:500 to 900:1, 1:500 to 800:1, 1:500 to 700:1, 1:500 to 600:1, 1:500 to 500:1, 1:500 to 400:1, 1:500 to 300:1, 1:500 to 200:1, 1:500 to 100:1, 1:500 to 50:1, 1:500 to 20:1, 1:500 to 10:1, 1:500 to 5:1, or 1:500 to 1:1.

In some embodiments, the mixed population of enriched cells comprises a ratio of HSPC to iNKT can comprise a range from 1:2 to 1,000,000:1, 1:2 to 500,000:1, 1:1 to 500,000:1, 100:1 to 1,000,000:1, 100:1 to 500,000:1, 100:1 to 100,000:1, 500:1 to 1,000,000:1, 500:1 to 500,000:1, 500:1 to 100,000:1, 1,000:1 to 100,000:1, 1,000:1 to 1,000,000:1, 1,000:1 to 500,000:1, 1,000:1 to 100,000:1, 10,000:1 to 1:2, 100,000:1-1:20, or 1,000,000:1-1:200.

In some embodiments, the mixed population of enriched cells comprises a ratio of naïve conventional αβ-T cells to HSPC less than 1:3, less than 1:50, less than 1:100, less than 1:200, less than 1:300, less than 1:400. less than 1:500, less than 1:600, less than 1:700, less than 1:800, less than 1:900, less than 1:1,000, less than 1:1,500, less than 1:2,000, less than 1:3,000, less than 1:4,000, less than 1:5,000, less than 1:6,000, less than 1:7,000, less than 1:8,000, less than 1:9,000, less than 1:10,000, less than 1:50,000, less than 1:100,000, less than 1:200,000, less than 1:300,000, less than 1:400,000, less than 1:500,000, less than 1:600,000, less than 1:700,000, less than 1:800,000, less than 1:900,000, or less than 1:1,000,000.

In some embodiments, the mixed population of enriched cells comprises a ratio of naïve conventional αβ-T cells to Tmem can be less than 1:30, less than 1:200, less than 1:300, less than 1:400, less than 1:500, less than 1:600, less than 1:700, less than 1:800, less than 1:900, less than 1:1000, less than 1:5000, less than 1:10000, less than 1:15000, less than 1:20000, less than 1:25000, less than 1:30000, less than 1:35000, less than 1:40000, less than 1:45000, or less than 1:50000.

The ratio of naïve conventional αβ-T cells to Treg can be less than 1:1, 1:10, less than 1:30, less than 1:200, less than 1:300, less than 1:400, less than 1:500, less than 1:600, less than 1:700, less than 1:800, less than 1:900, less than 1:1000, less than 1:5000, less than 1:10000, less than 1:15000, less than 1:20000, less than 1:25000, less than 1:30000, less than 1:35000, less than 1:40000, less than 1:45000, or less than 1:50000. The ratio of naïve conventional αβ-T cells to naïve Treg can be less than 1:1, 1:10, less than 1:30, less than 1:200, less than 1:300, less than 1:400, less than 1:500, less than 1:600, less than 1:700, less than 1:800, less than 1:900, less than 1:1000, less than 1:5000, less than 1:10000, less than 1:15000, less than 1:20000, less than 1:25000, less than 1:30000, less than 1:35000, less than 1:40000, less than 1:45000, or less than 1:50000. The ratio of naïve conventional αβ-T cells to Memory Treg can be less than 1:1, less than 1:2, less than 1:3, less than 1:4, less than 1:5, less than 1:6, less than 1:7, less than 1:8, less than 1:9, less than 1:10, less than 1:15, less than 1:20, less than 1:30, less than 1:200, less than 1:300, less than 1:400, less than 1:500, less than 1:600, less than 1:700, less than 1:800, less than 1:900, less than 1:1000, less than 1:5000, less than 1:10000, less than 1:15000, less than 1:20000, less than 1:25000, less than 1:30000, less than 1:35000, less than 1:40000, less than 1:45000, or less than 1:50000. The ratio of naïve conventional αβ-T cells to iNKT can be less than 100:1, less than 1:1, less than 1:2, less than 1:3, less than 1:4, less than 1:5, less than 1:6, less than 1:7, less than 1:8, less than 1:9, less than 1:10, less than 1:15, less than 1:20, less than 1:30, less than 1:200, less than 1:300, less than 1:400, less than 1:500, less than 1:600, less than 1:700, less than 1:800, less than 1:900, less than 1:1000, less than 1:5000, less than 1:10000, less than 1:15000, less than 1:20000, less than 1:25000, less than 1:30000, less than 1:35000, less than 1:40000, less than 1:45000, less than 1:50000.

In some embodiments of the instant disclosure, the ratio of Tmem to Treg is not dependent on the concentration of starting cells (e.g. substantially modified from the starting concentrations). This provides an advantage because the concentration of Tmem can be controlled (e.g. dose escalated) independent of the concentration of Treg. The ratio of Tmem to Treg can be from 30:1 to 1:1, 25:1 to 1:1, 20:1 to 1:1, 15:1 to 1:1, 10:1 to 1:1, 9:1 to 1:1, 8:1 to 1:1, 7:1 to 1:1, 6:1 to 1:1, 5:1 to 1:1, 4:1 to 1:1, 3:1 to 1:1, 2:1 to 1:1. In certain embodiments, the ratio of Tmem to Treg can be from 1:1 to 200:1, 1:10 to 2000:1, or 1:100 to 20,000:1. The ratio of Tmem to naïve Treg can be from 5:1 to 1:10, 3:1 to 1:10, 3:1 to 1:10, 2:1 to 1:10, or 1:1 to 1:10. The ratio of Tmem to memory Treg can be from 27:1 to 0.9:1, 30:1 to 1:10, 25:1 to 1:10, 20:1 to 1:10, 15:1 to 1:10, 10:1 to 1:10, 30:1 to 1:9, 30:1 to 1:8, 30:1 to 1:7, 30:1 to 1:6, 30:1 to 1:5, 30:1 to 1:4, 30:1 to 1:3, 30:1 to 1:2, or 30:1 to 1:1.

In some embodiments of the instant disclosure, the ratio of Treg to iNKT can be from 20,000:1 to 1:5, 200,000:1 to 1:50, or 2,000,000:1 to 1:500.

In some embodiments of the instant disclosure, the ratio of iNKT to Tmem can be from 2:1 to 1:100,000, 5:1 to 1:1,000,000, or 10:1 to 1:10,000,000.

In some embodiments, the HSPC are $CD34^+$. The HSPC can further be described as $CD133^+$, $CD90^+$, $CD38^-$, $CD45RA^-$, $Lin^-$, or any combination thereof. In some embodiments, the HSPC are $CD19^-$, $TCRα/β^-$, or a combination thereof. In some embodiments, the $Lin^+$ cells express CD19, CD11c, CD66B, CD14, CD20, or any combination thereof. In some embodiments, the Treg are $CD4^+$, $CD25^+$, $CD127^{-/lo}$, $FoxP3^+$, or any combination thereof. In some embodiments, the naïve Treg are $CD4^+$, $CD25^+$, $CD127^{-/lo}$, $FoxP3^+$, $CD45RA^+$, $CD45RO^-$, or any combination thereof. In some embodiments, the memory Treg are $CD4^+$, $CD25^+$, $CD127^{-/lo}$, $FoxP3^+$, $CD45RA^-$, $CD45RO^+$, or any combination thereof. In some embodiments, the Tmem are $CD3^+$, $CD45RA^-$, $CD45RO^+$, or any combination thereof. In some embodiments, the $T_{SCM}$ are $CD45RA^+$ and $CD4^+$ or $CD8^+$. The $T_{SCM}$ can further be described as $CD95^+$, $CD122^+$, $CXCR3^+$, $LFA-1^+$, or any combination thereof. In some embodiments, the $T_{CM}$ are $CD45RO^+$ and $CD4^+$ or $CD8^+$. The $T_{CM}$ can further be described as $CD45RA^-$, $CD62L^+$, $CCR7^+$, or any combination thereof. In some embodiments, the $T_{EM}$ are $CD4^+$, $CD45RO^+$, $CD45RA^-$, $CD62L^-$, $CCR7^-$, or any combination thereof. In some embodiments, the iNKT are $CD1d-tet^+$, $6B11^+$, $Vα24Jα18^+$ or any combination thereof. In any of the embodiments described herein, the naïve conventional αβ-T cells are $TCRα/β^+$ $CD45RA^+$ and $CD25^-$, $CD127^+$, or both. The naïve conventional αβ-T cells can further be described as $TCRα^+$ $TCRβ^+$ $CD45RA^+$ $CD45RO^-$ $CD25^-$ $CD95^-$ $IL-2Rβ^-$ $CD127^+$.

In some embodiments, a biological sample may be sorted to isolate populations of interest such as HSPCs, Treg cells, Tmem cells or a combination thereof. In some cases, a biological sample may be contacted with a molecule that specifically binds CD34 for isolation of HSPCs. The sample may be enriched for $CD34^+$ to yield a $CD34^+$ cell population and a $CD34^-$ cell population. In some cases, the $CD34^-$ cell population may be contacted with a molecule that specifically binds CD25. The sample may then be enriched for $CD25^+$ cells by sorting the $CD34^-$ cell population for a $CD25^+$ cell population, thereby yielding a $CD34^-CD25^-$ cell population and a $CD34^-CD25^+$ cell population. The $CD34^-CD25^+$ cell population may be further sorted to yield a Treg cell population. The $CD34^-CD25^+$ cells may be contacted with a molecule that specifically binds CD4 and a molecule that specifically binds CD127. The cells may then be sorted to yield a $CD34^-CD25^+CD4^+CD127^{dim/-}$ Treg cell population. In some cases, the $CD34^-CD25^-$ cell population may be further sorted to enrich Tmem cells. The cells may be contacted with a molecule that specifically binds CD45RA. The cell sample may be sorted to yield a $CD34^-CD25^-CD45RA^-$ Tmem cell population. The $CD45RA^+$ naïve conventional αβ-T cells may be discarded for the depletion of naïve conventional αβ-T cells.

In some embodiments, a biological sample may be sorted to isolate populations of interest such as HSPCs, Treg cells, Tmem cells, iNKT cells or a combination thereof. In some cases, a biological sample may be contacted with a molecule that specifically binds CD34 for isolation of HSPCs. The sample may be enriched for $CD34^+$ to yield a $CD34^+$ cell population and a $CD34^-$ cell population. In some cases, the $CD34^-$ cell population may be contacted with a molecule that specifically binds CD25 and a molecule that specifically binds 6B11. The sample may then be enriched for $CD25^+$ and $6B11^+$ cells by sorting the $CD34^-$ cell population for a $CD25^+$ cell population, thereby yielding a $CD34^-CD25^-6B11^-$ cell population and a $CD34^-CD25^+6B11^+$ cell population. The $CD34^-CD25^+6B11^+$ cell population may be further sorted to yield a Treg and iNKT cell population. The $CD34^-CD25^+6B11^+$ cells may be contacted with a molecule that specifically binds CD4 and with a molecule that specifically binds CD127. The cells may then be sorted to yield a $CD34^-CD25^+6B11^+CD4^+CD127^{dim/-}$ Treg cell population. In some cases, the $CD34^-CD25^-6B11^-$ cell population may be further sorted to enrich Tmem cells. The cells may be contacted with a molecule that specifically binds CD45RA. The cell sample may be sorted to yield a $CD34^-CD25^-6B11^-CD45RA^-$ Tmem cell population. The $CD45RA^+$ naïve conventional αβ-T cells may be discarded for the depletion of naïve conventional αβ-T cells. In some embodiments, the method of producing the therapeutic compositions described herein may comprise separately sorting different populations of cells. For instance, HSPCs, Treg cells, Tmem cells and/or iNKT cells may be sorted separately. The separately sorted populations may be mixed to form a therapeutic composition. In some cases, the separate populations of cells may be isolated from different donors. For instance, HSPCs may be isolated from donor 1 and Treg and Tmem cells may be sorted from donor 2. Alternatively, all cell populations may be isolated from the same donor. In some embodiments, the sample comprises mobilized peripheral blood, mobilized apheresis product, bone marrow, umbilical cord blood, non-mobilized blood, non-mobilized apheresis product, or any combination thereof. In some embodiments, the sample comprises cultured cells derived from PBMCs. In some embodiments, the sample comprises cultured cells derived from induced pluripotent stem cells (iPSC). In some embodiments, the sample is prepared for processing a density gradient, Ficoll, Percoll, red blood cell hypotonic lysis, Ammonium-Chloride-Potassium (ACK) buffer, or any combination thereof. In some embodiments, the sample is provided by a single tissue harvest. In some embodiments, the sample is provided by one or more tissue harvests.

Example Sort Scheme 1

In certain embodiments, the methods for producing a pharmaceutical composition comprise: A. contacting the sample with a molecule that specifically binds CD34 under conditions to form a population of CD34$^+$ cells and a population of CD34$^-$ cells, recovering the population of CD34$^+$ cells from the sample, and recovering the population of CD34$^-$ cells from the sample; and B. processing the population of CD34$^-$ cells to provide least one population of enriched therapeutic cells comprising Treg, Tmem, iNKT, or any combination thereof (see FIGS. 1A and B). In some embodiments, step B comprises performing a fine sort to provide the population of enriched therapeutic cells (see FIG. 1A). For example, step B can comprise contacting the population of CD34$^-$ cells with a molecule that specifically binds CD45RA, a molecule that specifically binds CD45RO, a molecule that specifically binds CD4, a molecule that specifically binds CD8, a molecule that specifically binds CD25, a molecule that specifically binds CD127, a CD1d-tet, a 6B11 monoclonal antibody or functional fragment thereof, or any combination thereof.

In certain embodiments, step B comprises: i. contacting the population of CD34$^-$ cells with at least one molecule that specifically binds CD45RA under conditions to form a population of CD45RA$^+$ cells and a population of CD45RA$^-$ cells, and recovering the population of CD45RA$^-$ cells; and ii. performing a fine sort to provide the population of enriched therapeutic cells from the population of CD45RA$^+$ cells. The fine sort can comprise contacting the population of CD45RA$^+$ cells with a molecule that specifically binds CD4, a molecule that specifically binds CD8, a molecule that specifically binds CD25, a molecule that specifically binds CD127, a CD1d-tet, a 6B11 monoclonal antibody or functional fragment thereof, or any combination thereof. The fine sort can further comprise contacting the population of CD45RA$^-$ cells with a molecule that specifically binds CD45RA, a molecule that specifically binds CD45RO, or a combination thereof.

In certain embodiments, step B comprises: i. contacting the population of CD34$^-$ cells with at least one binding molecule that specifically binds a Lin$^+$ marker under conditions to form a population of Lin$^+$ cells and a population of Lin$^-$ cells, and recovering the population of Lin$^-$ cells; and ii. performing a fine sort to provide the population of enriched therapeutic cells from the population of Lin$^-$ cells. In some embodiments, the fine sort comprises contacting the population of Lin$^-$ cells with a molecule that specifically binds CD45RA, a molecule that specifically binds CD45RO, a molecule that specifically binds CD4, a molecule that specifically binds CD8, a molecule that specifically binds CD25, a molecule that specifically binds CD127, a CD1d-tet molecule, a 6B11 monoclonal antibody or functional fragment thereof, or any combination thereof.

In certain embodiments, step B comprises: i. contacting the population of CD34$^-$ cells with at least one binding molecule that specifically binds at least one Lin$^+$ marker under conditions to form a population of Lin$^+$ cells and a population of Lin$^-$ cells, and recovering the population of Lin$^-$ cells; and ii. contacting the population of Lin$^-$ cells with a binding molecule that specifically binds CD25 under conditions to form a population of CD25$^+$ cells and a population of CD25$^-$ cells, recovering the population CD25$^+$ cells, thereby producing a population of cells comprising Treg, and recovering the population of CD25$^-$ cells; and iii. contacting the population of CD25$^-$ cells with a binding molecule that specifically binds CD45RA under conditions to form a population of CD45RA$^+$ cells and a population of CD45RA$^-$ cells, and recovering the population of CD45RA$^-$ cells (see FIG. 1A). In some embodiments, step ii. further comprises contacting the Lin$^-$ cells with CD1d-tet, a 6B11 monoclonal antibody or functional fragment thereof, or a combination thereof under conditions to form a population of CD1d-tet$^+$ cells, a population of 6B11$^+$ cells, or a combination thereof and a population of CD1d-tet$^-$ cells, 6B11$^-$ cells, or a combination thereof, and recovering the population of CD1d-tet$^+$ cells. In some embodiments, the population of CD25$^+$ cells and the population of CD1d-tet$^+$ cells, 6B11$^+$ cell or both are recovered simultaneously. In some embodiments, the method further comprises performing a fine sort of the population of CD25$^+$ cells of step ii. to provide a population of naïve Treg cells, a population of memory Treg cells, a population of iNKT cells, or any combination thereof. In some embodiments, the population of CD45RA$^+$ cells is recovered and further performing a fine sort to provide a population of Treg, iNKT, or both.

Example Sort Scheme 2

Figure 2A:
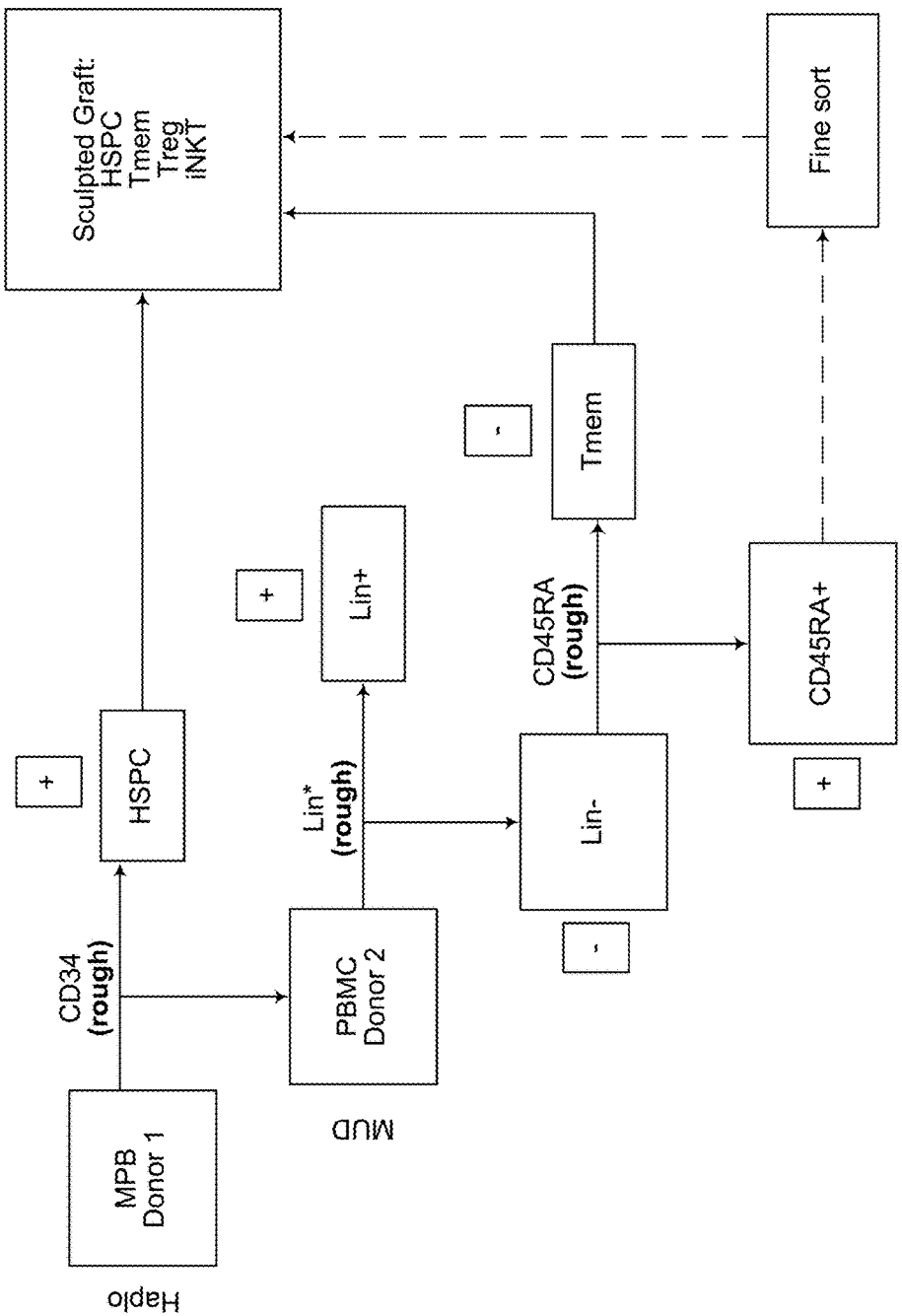
FIG. 2A-B.
Figure 2B:
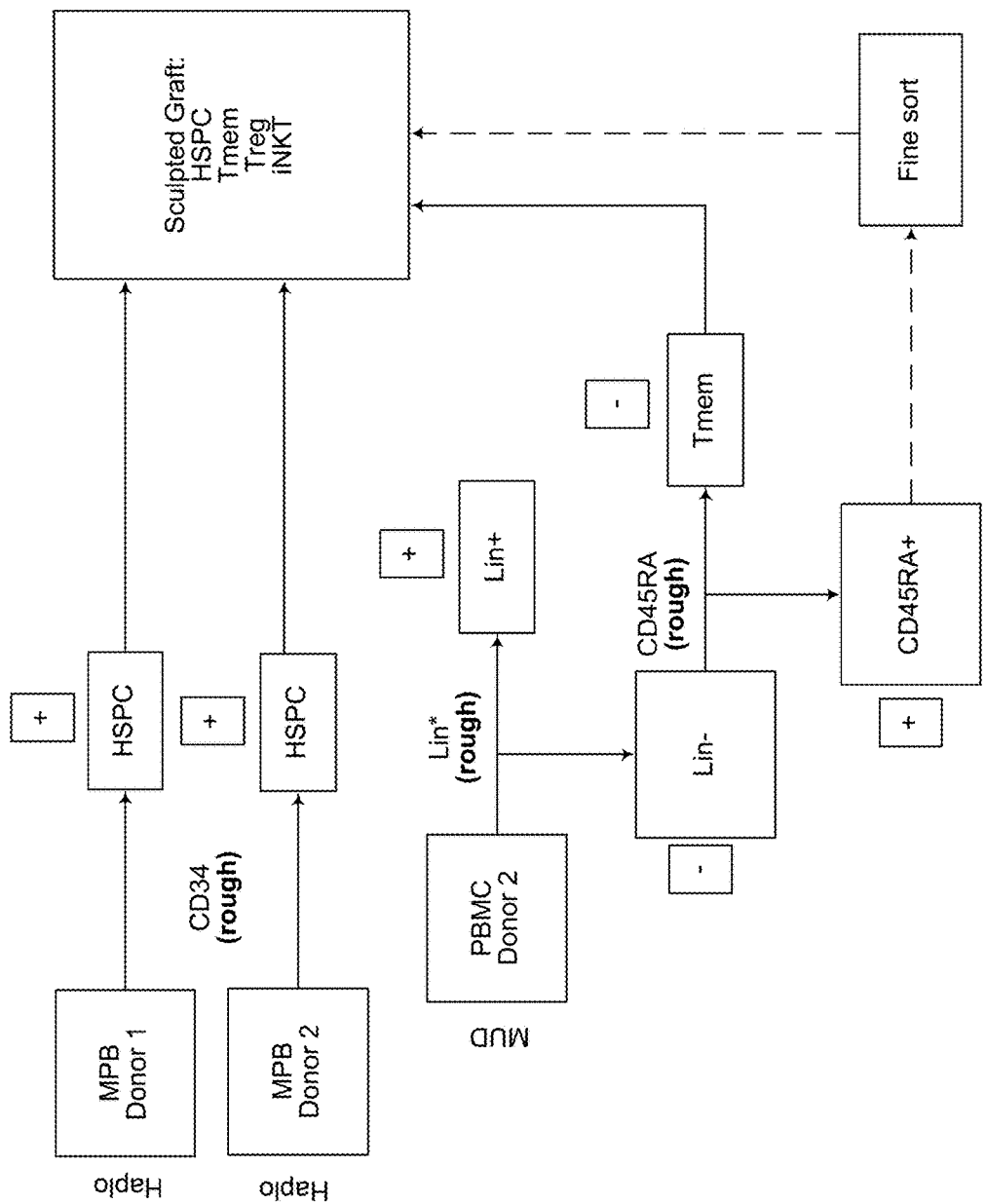

In certain embodiments, the methods for producing a pharmaceutical composition comprise: A. performing a first rough sort on at least a first sample, thereby providing an enriched population of CD34$^+$ cells; B. performing a second rough sort on a second sample, thereby providing a population of Lin$^-$ cells; C. performing a third rough sort on the population of Lin$^-$ cells, thereby providing a population of CD45RA$^-$ memory T cells and providing a population of CD45RA$^+$ cells; and D. performing a fine sort on the population of CD45RA$^+$ cells, thereby providing a population of Treg (see FIGS. 2 and 3).

Figure 3:
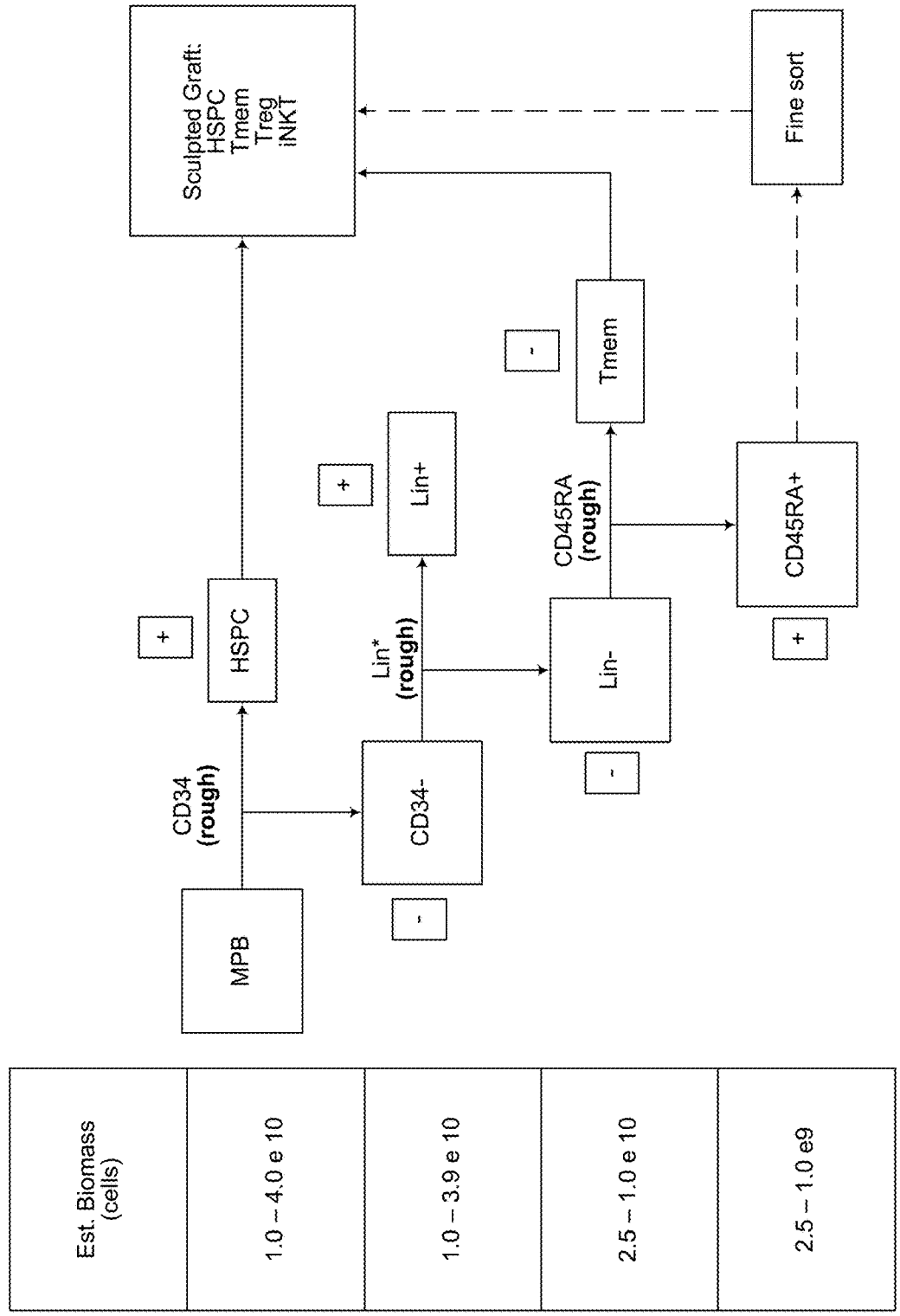
FIG. 3 shows a schematic representation of a process for producing a sculpted graft cellular composition.

In some embodiments, the second sample comprises a population of CD34$^-$ cells recovered from step A (see FIG. 3). In some embodiments, the first sample comprises at least one haploidentical sample (see FIG. 2A). In some embodiments, the first sample comprises at least two haploidentical samples (see FIG. 2B). In some embodiments, the first sample comprises mobilized peripheral blood, mobilized apheresis product, bone marrow, umbilical cord blood, non-mobilized blood, non-mobilized apheresis product, or any combination thereof. In some embodiments, the second sample comprises peripheral blood mononuclear cells (PBMC), mobilized peripheral blood, mobilized apheresis product, bone marrow, umbilical cord blood, non-mobilized blood, non-mobilized apheresis product, or any combination thereof. In some embodiments, the first sample or the second sample is allogeneic, autologous, or a combination thereof. In some embodiments, the second sample is from an HLA matched unrelated donor, a HLA matched sibling donor, or a combination thereof (see FIGS. 2A & B).

In some embodiments, the first, second, or third rough sort comprises density separation, tetrameric antibody complex mediated enrichment/depletion, magnetic activated cell sorting, apheresis, leukapheresis, or any combination thereof.

In some embodiments, the fine sort can comprise purification using multi-parameter fluorescence-based molecular phenotypes. The fine sort can provide a population of naïve Treg cells, a population of memory Treg cells, a population of iNKT cells, or any combination thereof. The fine sorting can comprise contacting the CD45RA$^+$ cells with a binding molecule that specifically binds CD25 under conditions to provide a population of CD25$^+$ cells and a population of CD25$^-$ cells, and recovering a population of CD25$^+$ cells, thereby providing a population of Treg. In some embodiments, the population of CD25$^+$ cells is further sorted under conditions to provide a population of naïve Treg cells. In some embodiments, the fine sort comprises contacting the CD45RA$^+$ cells with a CD1d-tet, 6B11 monoclonal antibody or functional fragment thereof, or a combination thereof under conditions to provide a population of CD1d-tet$^+$ cells, 6B11$^+$ cells, or both, and recovering the population of CD1d-tet$^+$ cells, 6B11$^+$ cells, or both.

Example Sort Scheme 3

In certain embodiments, the methods for producing a pharmaceutical composition comprise: A. contacting the sample with a binding molecule that specifically binds a Lin$^+$ marker under conditions to provide a population of Lin$^+$ cells and a population of Lin$^-$ cells, and recovering the population of Lin$^-$ cells; B. contacting the Lin$^-$ cells with a binding molecule that specifically binds CD34 and a binding molecule that specifically binds CD25 under conditions to provide a population of CD34$^+$ cells, a population of CD25$^+$ cells, and a population of CD34$^-$ CD25$^-$ cells, and recovering the CD34$^+$ cells and CD25$^+$ cells and recovering the population of CD34$^-$ CD25$^-$ cells; and C. contacting the population of CD34$^-$ CD25$^-$ cells with a binding molecule that specifically binds CD45RA under conditions to provide a population of CD45RA$^+$ cells and a population of CD45RA$^-$ cells, and recovering a population of CD45RA$^-$ (see FIG. 4).

Figure 4:
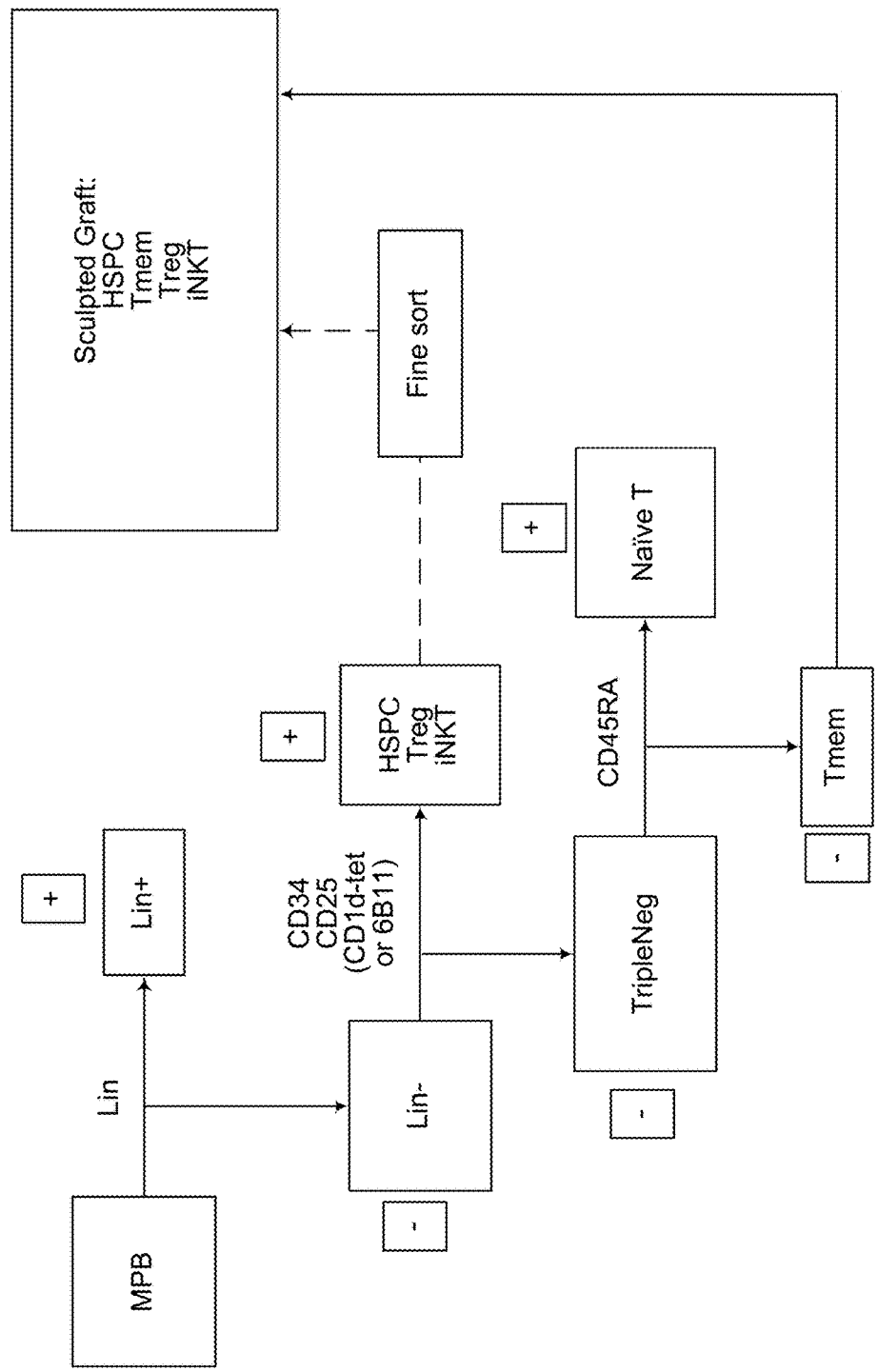
FIG. 4 shows a schematic representation of a process for producing a sculpted graft cellular composition.

In some embodiments, step B further comprises contacting the Lin$^-$ cells with a CD1d-tet, a 6B11 monoclonal antibody or functional fragment thereof, or a combination thereof under conditions to provide a population of CD1d-tet$^+$ cells, 6B11$^+$ cells, or a combination thereof, and recovering the CD1d-tet$^+$ cells, 6B11$^+$ cells, or a combination thereof (see FIG. 4). In some embodiments, the method further comprises performing a fine sort of the CD34$^+$ cells, CD25$^+$ cells, CD1d-tet$^+$ cells, 6B11$^+$ cells, or any combination thereof, thereby providing a population CD34$^+$ cells, CD25$^+$ cells, CD1d-tet$^+$ cells, 6B11$^+$ cells, or any combination thereof (see FIG. 4). In some embodiments, the fine sort comprises contacting the CD34$^+$ cells, CD25$^+$ cells, CD1d-tet$^+$ cells, 6B11$^+$ cells, or any combination thereof with a binding molecule that specifically binds CD34, a binding molecule that specifically binds CD4, a binding molecule that specifically binds CD25, a binding molecule that specifically binds CD127, a CD1d-tet, a 6B11 monoclonal antibody or functional fragment thereof, or any combination thereof under conditions to provide a population of cells highly enriched for CD34$^+$ cells, CD4$^+$ CD25$^+$ CD127$^{-/Lo}$ cells, CD1d-tet$^+$ cells, or a combination thereof (see FIG. 4).

Example Sort Scheme 4

Figure 5:
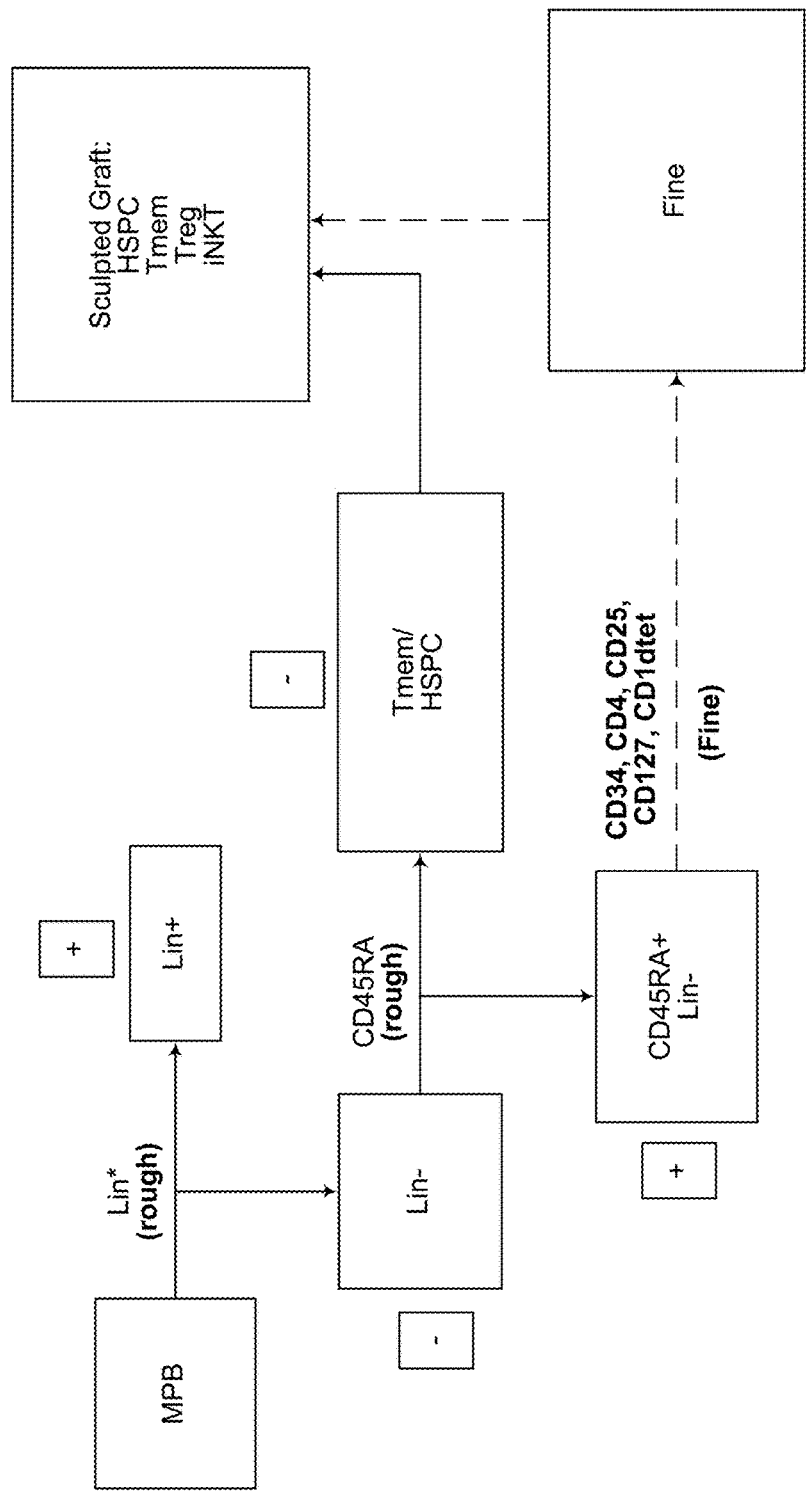
FIG. 5 shows a schematic representation of a process for producing a sculpted graft cellular composition.

In certain embodiments, the methods for producing a pharmaceutical composition comprise: A. performing a rough sort of the sample to provide a population of Lin$^+$ cells and a population of Lin$^-$ cells, and recovering the population of Lin$^-$ cells; B. performing a rough sort of the population of Lin$^-$ cells provide a population of enriched in HSPC and Tmem and a population of CD45RA$^+$ cells, and recovering the population of HSPC and Tmem and recovering the population of CD45RA$^+$ cells; and C. performing a fine sort of the population of CD45RA$^+$ cells to provide a population of Treg (see FIG. 5). In some embodiments, the fine sort further comprises contacting the population of CD45RA$^+$ cells with a binding molecule that specifically binds CD34, a binding molecule that specifically binds CD4, and a binding molecule that specifically binds CD127 under conditions to provide a population of CD34+ cells and a population of CD4$^+$ CD25$^+$ CD127$^{-/Lo}$ cells, and recovering a population of CD34+ cells and a population of CD4$^+$ CD25$^+$ CD127$^{-/Lo}$ cells. In some embodiments, the fine sort further comprises contacting the population CD45RA$^+$ cells with a CD1d-tet, 6B11 monoclonal antibody or functional fragment thereof, or a combination thereof, and recovering a population of CD1d-tet$^+$ cells, 6B11$^+$ cells, or a combination thereof. In some embodiments, the rough sort comprises density separation, tetrameric antibody complex mediated enrichment/depletion, magnetic activated cell sorting, apheresis, leukapheresis, or any combination thereof.

Example Sort Scheme 5

In certain embodiments, the methods for producing a pharmaceutical composition comprise: A. contacting the sample with a binding molecule that specifically binds CD34 under conditions to provide a population of CD34$^+$ cells and a population of CD34$^-$ cells, recovering the population of CD34$^+$ cells, and recovering the population of CD34$^-$ cells; B. contacting the population of CD34$^-$ cells with a binding molecule that specifically binds CD25 under conditions to provide a population of CD25$^+$ cells and a population of CD25$^-$ cells, recovering the population of CD25$^+$ cells, and recovering the population of CD25$^-$ cells; and C. contacting the population of CD25$^-$ cells with a binding molecule that specifically binds CD45RA under conditions to provide a population of CD45RA$^+$ cells and a population of CD45RA$^-$ cells, and recovering a population of CD45RA$^-$ cells (see FIGS. 6, 10, 11, 12).

Figure 6:
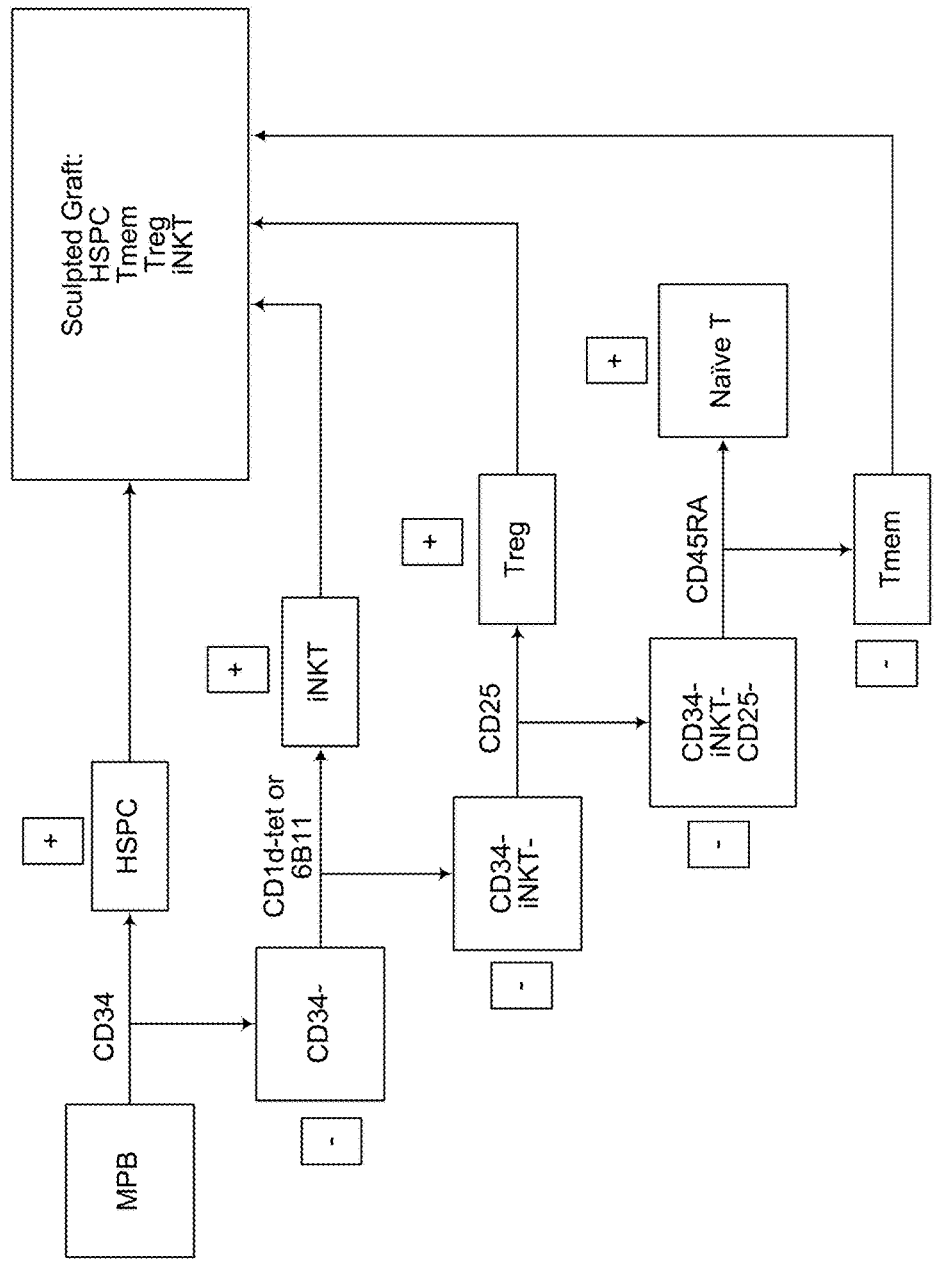
FIG. 6 shows a schematic representation of a process for producing a sculpted graft cellular composition.

In some embodiments, step B further comprises: i. contacting the population of CD34$^-$ cells with a CD1d-tet, a 6B11 monoclonal antibody or functional fragment thereof, or a combination thereof under conditions to provide a population of CD1d-tet$^+$ cells, a population of 6B11$^+$ cells, or a combination thereof and a population of CD1d-tet$^-$ cells, a population of 6B11$^-$ cells, or a combination thereof, and recovering a population of CD1d-tet$^+$ cells, a population of 6B11$^+$ cells, or a combination thereof, thereby providing a population of iNKT-depleted cells and recovering a population of CD1d-tet$^-$ cells, a population of 6B11$^-$ cells, or both, thereby providing a population of iNKT-depleted cells; and ii. contacting the population of iNKT-depleted cells with a binding molecule that specifically binds CD25 under conditions to provide a population of CD25$^+$ cells and a population of CD25$^-$ cells, and recovering the population of CD25$^+$ cells and recovering a population of CD25$^-$ cells (see FIG. 6).

Figure 10:
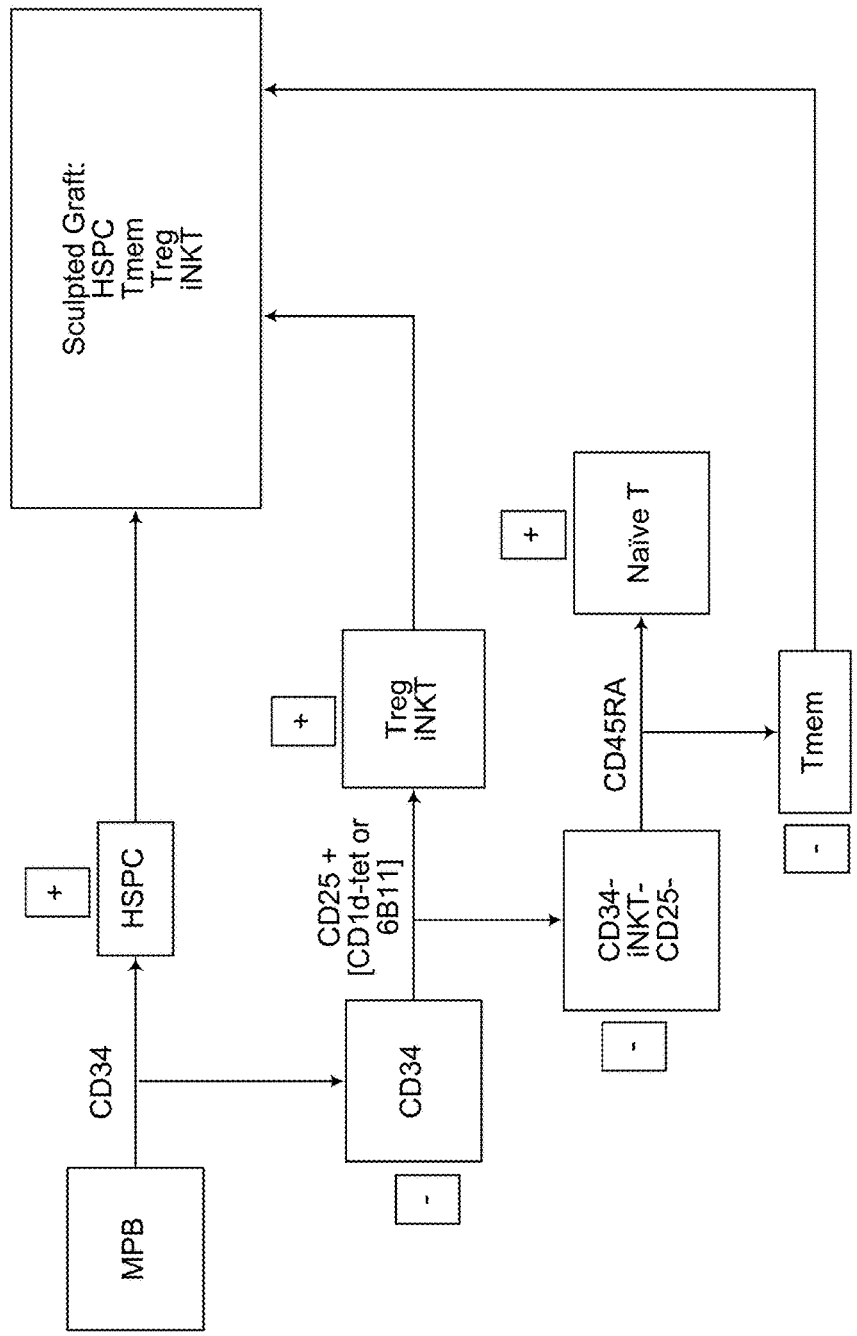
FIG. 10 shows a schematic representation of a process for producing a sculpted graft cellular composition.

In some embodiments, step B comprises contacting the population of CD34$^-$ cells with a binding molecule that specifically binds CD25, and a CD1d-tet, a 6B11 monoclonal antibody or functional fragment thereof, or a combination thereof under conditions to provide a population of CD25+ cells and a population of CD1d-tet+ cells, 6B11+ cells, or a combination thereof and a population of CD34− CD25− iNKT-depleted cells, and recovering the population of CD25+ cells and the population of CD1d-tet+ cells, 6B11+ cells, or a combination thereof, and recovering the population of CD34− CD25− iNKT-depleted cells (see FIG. 10).

Figure 11:
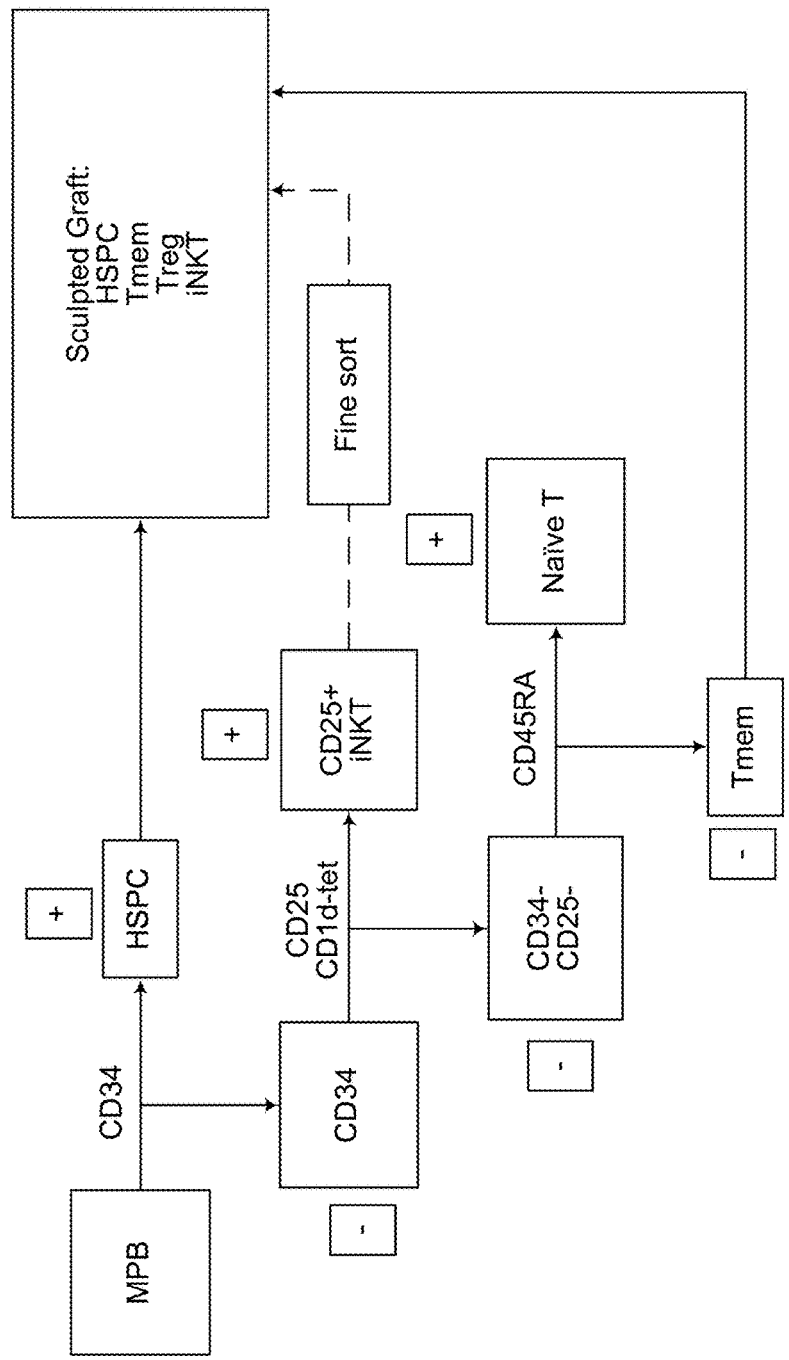
FIG. 11 shows a schematic representation of a process for producing a sculpted graft cellular composition.

In some embodiments, step B comprises: i. contacting the population of CD34− cells with a binding molecule that specifically binds CD25, and a CD1d-tet, a 6B11 monoclonal antibody or functional fragment thereof, or a combination thereof under conditions to provide a population of CD25+ cells and a population of CD1d-tet+ cells, 6B11+ cells, or a combination thereof and a population of CD34− CD25− iNKT-depleted cells, and recovering the population of CD25+ cells and the population of CD1d-tet+ cells, 6B11+ cells, or a combination thereof, and recovering the population of CD34− CD25− iNKT-depleted cells; and ii. performing a fine sort of the population of CD25+ cells and the population of CD1d-tet+ cells, 6B11+ cells, or a combination thereof by contacting the cells with a binding molecule that specifically binds CD4, a binding molecule that specifically binds CD25, a binding molecule that specifically binds CD127, a CD1d-tet, a 6B11 monoclonal antibody or functional fragment thereof, or any combination thereof, to provide a population of cells enriched for CD4+CD25+ CD127−/Lo cells, CD1d-tet+ cells, 6B11+ cells, or any combination thereof (see FIG. 11).

Figure 15:
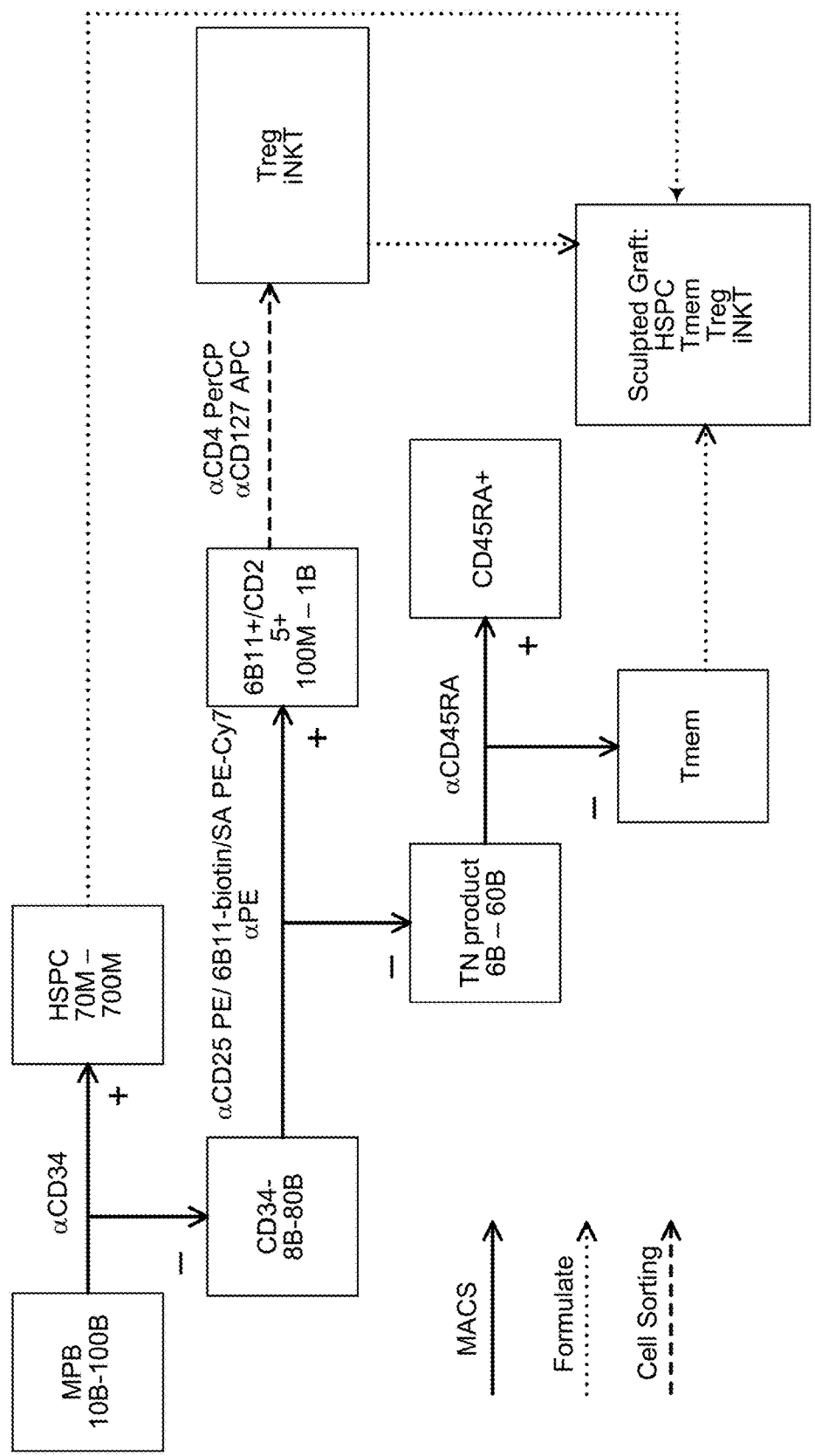
FIG. 15 shows a schematic representation of a process for producing a sculpted graft cellular composition.

In some embodiments, step B comprises: i. contacting the population of CD34− cells with an anti-CD25 antibody that comprises a tag (e.g. a fluorescent phycoerythrin), and a biotinylated 6B11 monoclonal antibody (6B11-biotin). The 6B11-biotin is then contacted with streptavidin that is conjugated with the same tag as the anti-CD25 antibody. In some embodiments, the streptavidin is conjugated to phycoerythrin/Cy7 (SAv-PE/Cy7). The cells are then contacted with anti-tag magnetic particles. In some embodiments, the magnetic particles are anti-PE magnetic particles (e.g., magnetic beads). CD25+ cells and 6B11 bound cells are then separated using MACS to produce a population of CD25+ cells and 6B11+ cells, and a population of CD34− CD25− iNKT-depleted cells (see FIG. 15). In some embodiments, Step B further comprises: ii. performing a fine sort of the population of CD25+ cells and 6B11+ cells by contacting the cells with a binding molecule that specifically binds CD4 and a binding molecule that specifically binds CD127 under conditions to provide a population of cells enriched for CD4+CD25+CD127−/Lo cells and a population of cells enriched for 6B11+CD127+ cells, or any combination thereof. In some embodiments, the CD4 binding molecule is anti-CD4 PerCP labeled antibody. In some embodiments, the CD127 binding molecule is anti-CD127 APC labeled antibody. The fine sort can comprise FACS wherein the CD25-PE, 6B11-biotin-SAv-PE/Cy7, CD4-PerCP, and CD127-APC are detected.

Figure 12:
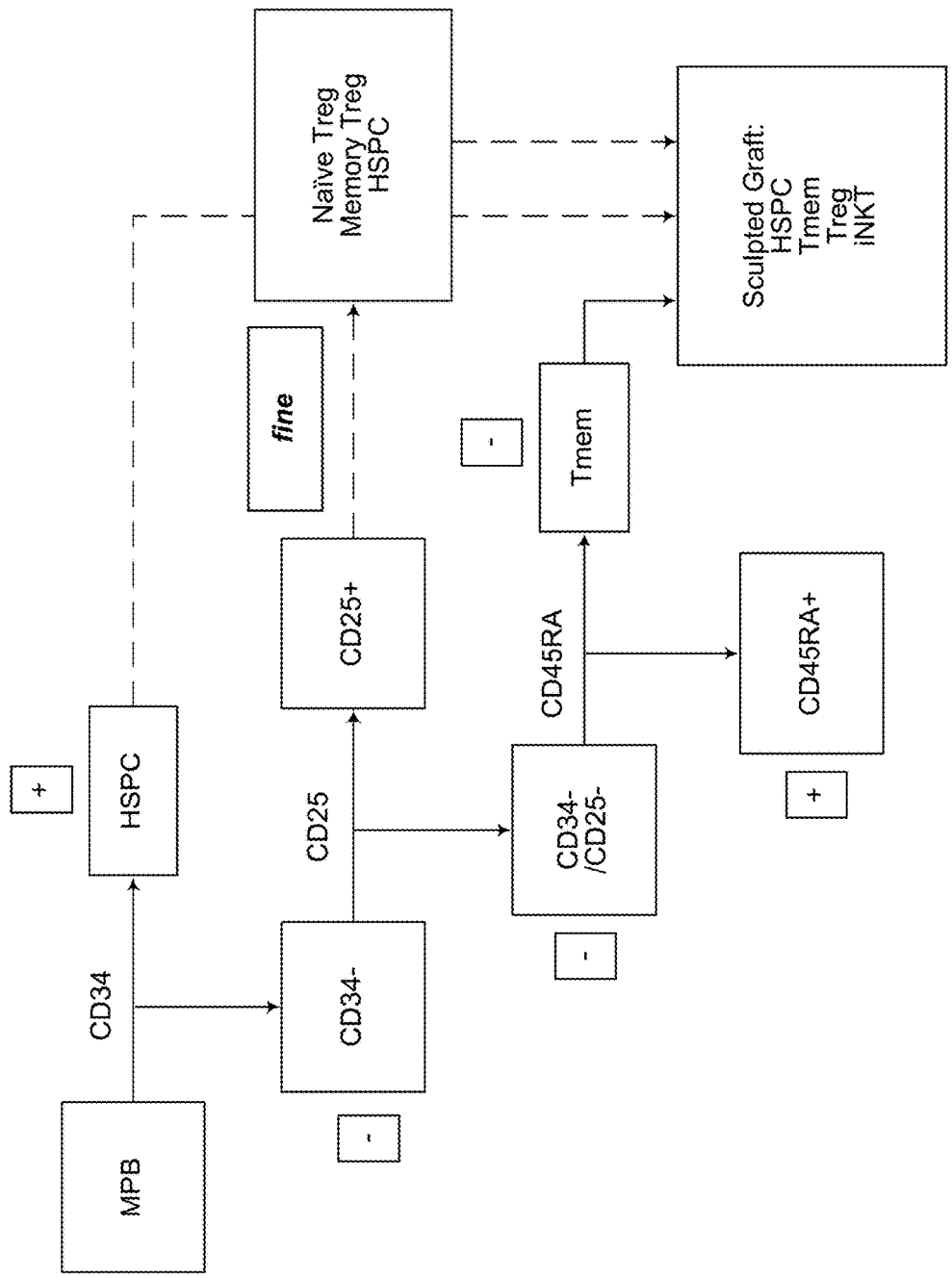
FIG. 12 shows a schematic representation of a process for producing a sculpted graft cellular composition.

In some embodiments, the population of CD34+ cells recovered in step A, the population of CD25+ cells recovered in step B, or both are further processed by a fine sort comprising contacting the CD34+ cells, the CD25+ cells, or a combination thereof with a binding molecule that specifically binds CD34, a binding molecule that specifically binds CD127, a binding molecule that specifically binds CD45RA, or any combination thereof (see FIG. 12)

Example Sort Scheme 6

Figure 7:
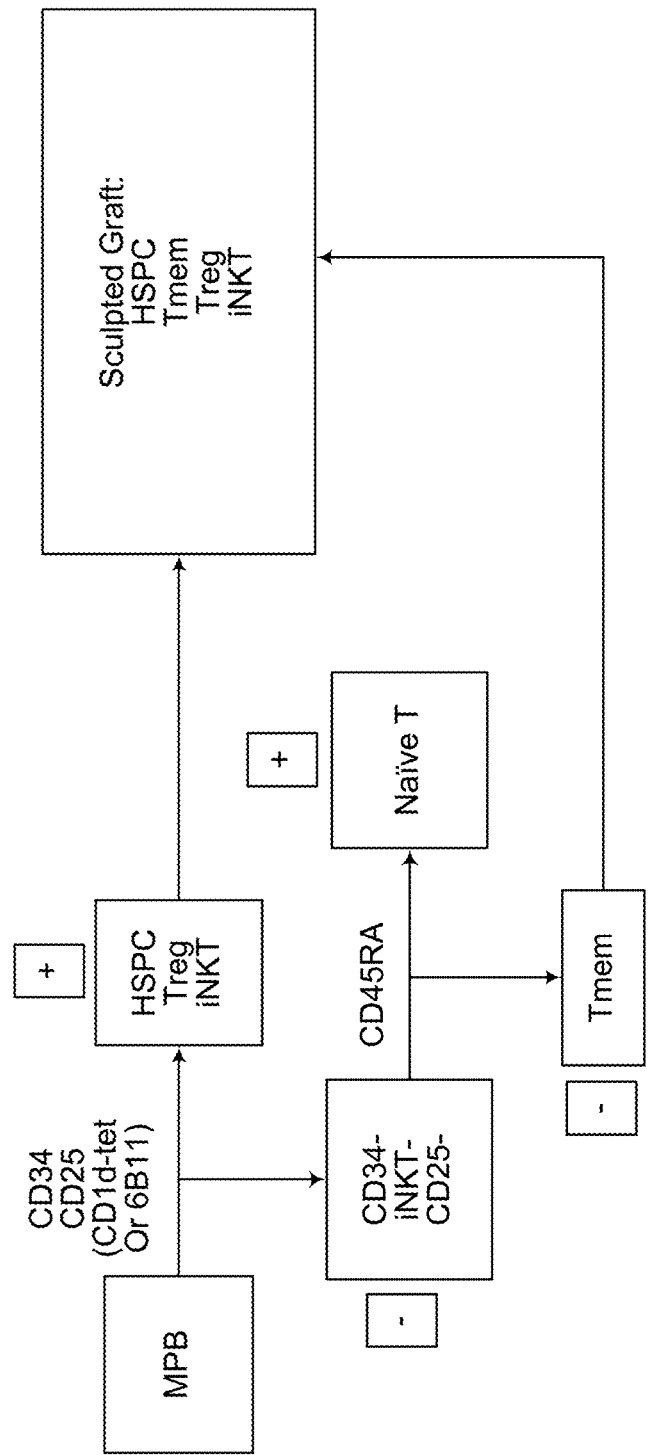
FIG. 7 shows a schematic representation of a process for producing a sculpted graft cellular composition.
Figure 8:
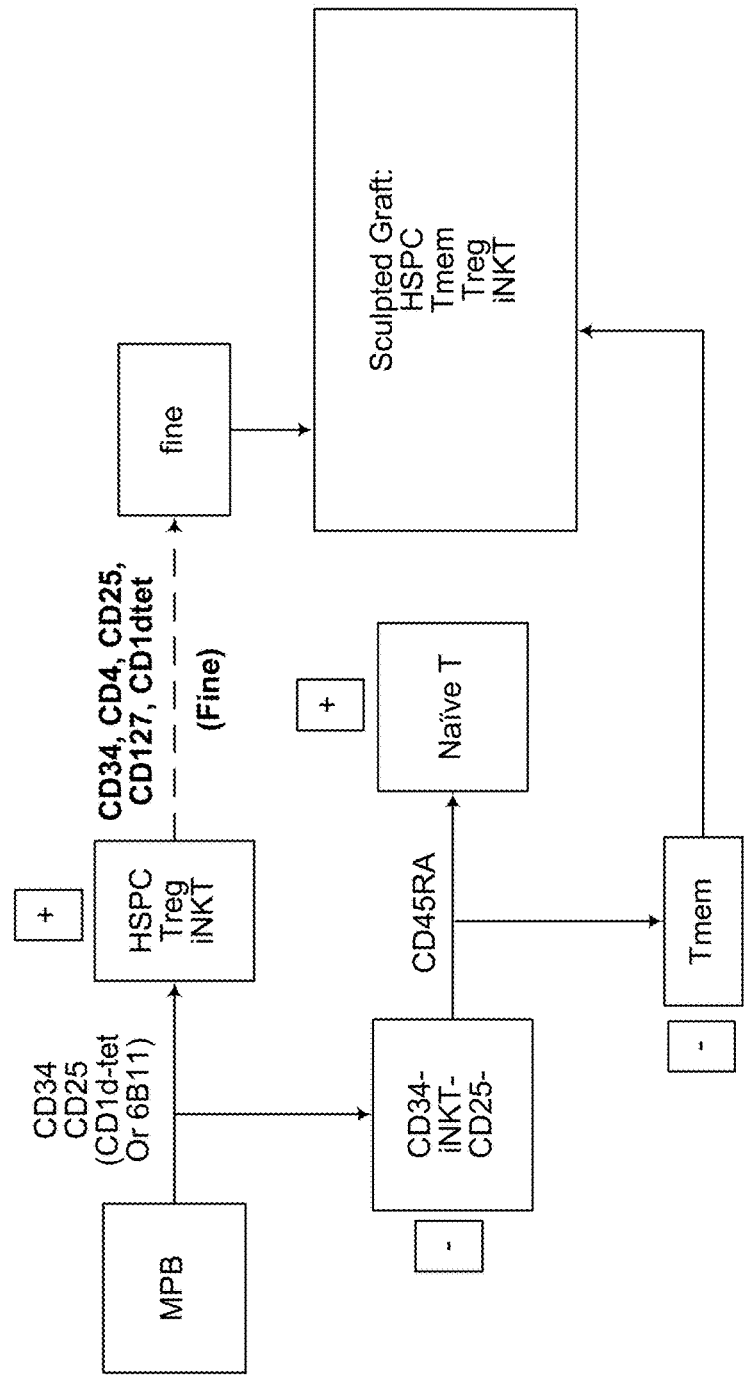
FIG. 8 shows a schematic representation of a process for producing a sculpted graft cellular composition.
Figure 9:
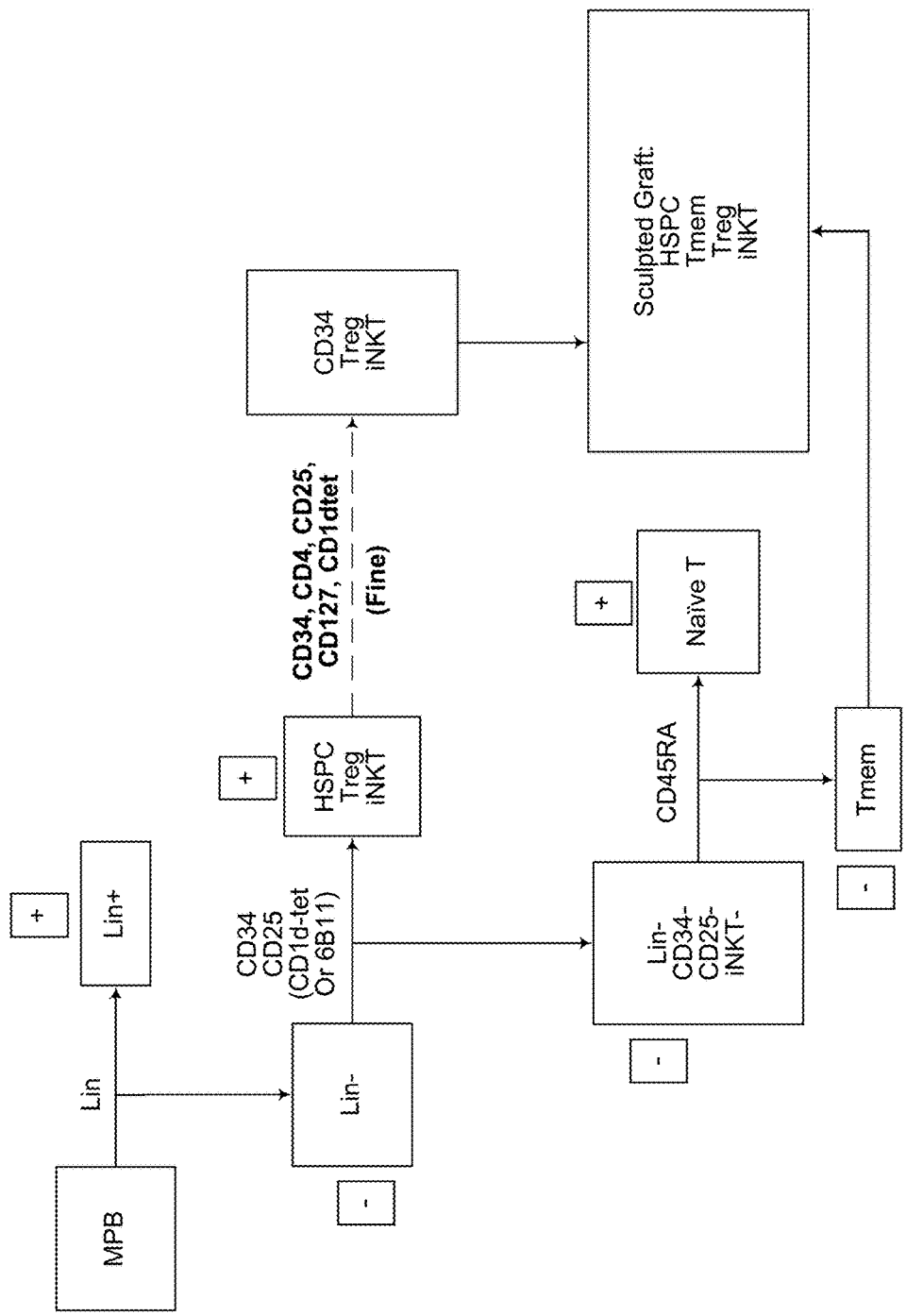
FIG. 9 shows a schematic representation of a process for producing a sculpted graft cellular composition.

In certain embodiments, the methods for producing a pharmaceutical composition comprise: A. contacting the sample with a binding molecule that specifically binds CD34 and a binding molecule that specifically binds CD25 under conditions to provide a population of CD34+ cells, a population of CD25+ cells and a population of CD34− CD25− cells, recovering the population CD34+ cells and the population of CD25+ cells, and recovering the population of CD34− CD25− cells; and B. contacting the population of CD34− CD25− cells with a binding molecule that specifically binds CD45RA under conditions to provide a population of CD45RA+ cells and a population of CD45RA− cells, and recovering the population of CD45RA− cells (see FIG. 7). In some embodiments, step A further comprises contacting the sample with a CD1d-tet, a 6B11 monoclonal antibody or functional fragment thereof, or a combination thereof under conditions to provide a population of CD1d-tet+ cells, a population of 6B11+ cells, or a combination thereof, and recovering the population of CD1d-tet+ cells, the population of 6B11+ cells, or a combination thereof (see FIG. 7). In some embodiments, the method further comprises performing a fine sort of the population of cells provided in step A by contacting the cells with a binding molecule that specifically binds CD34, a binding molecule that specifically binds CD4, a binding molecule that specifically binds CD25, a binding molecule that specifically binds CD127, a CD1d-tet, or any combination thereof, to provide a population of cells enriched for CD34+ cells, CD4+CD25+CD127−/Lo cells, CD1d-tet+ cells, or any combination thereof (see FIG. 8).

Example Sort Scheme 7

Figure 13:
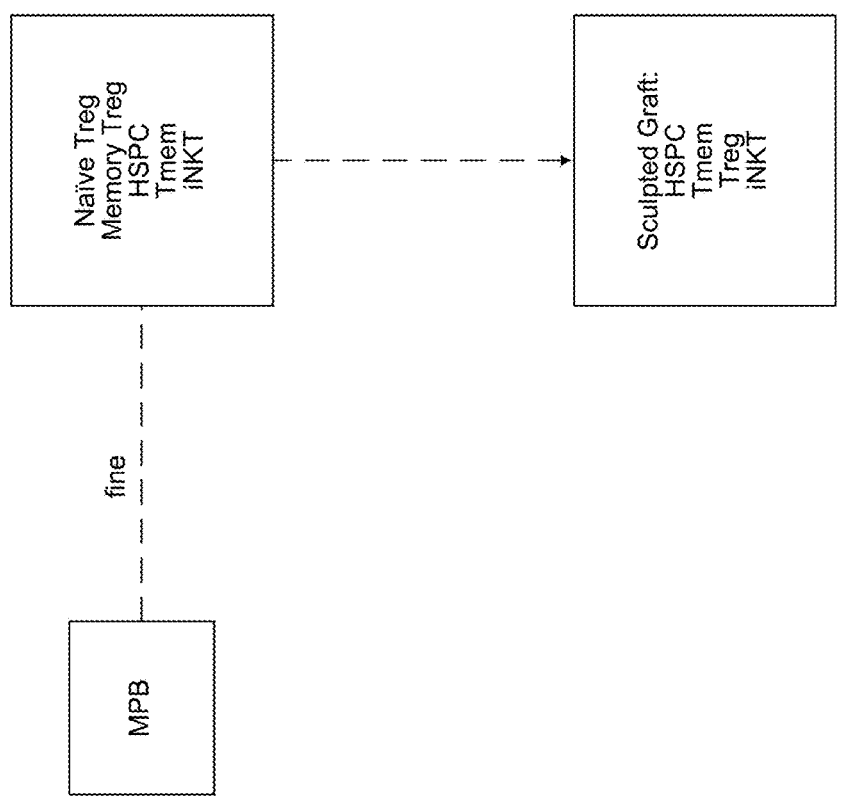
FIG. 13 shows a schematic representation of a process for producing a sculpted graft cellular composition.

In certain embodiments, the methods for producing a pharmaceutical composition comprise simultaneously processing the sample to provide an enriched population of cells comprising HSPC, Tmem, naïve Treg, memory Treg, and comprising less than 5% of undesired cells types (see FIG. 13). In some embodiments, the sample is contacted with a binding molecule that specifically binds CD34, a binding molecule that specifically binds CD4, a binding molecule that specifically binds CD8, a binding molecule that specifically binds CD25, a binding molecule that specifically binds CD127, a binding molecule that specifically binds CD45RA, a binding molecule that specifically binds CD45RO, or any combination thereof. In some embodiments, the method further comprises contacting the sample with a CD1d-tet, a 6B11 monoclonal antibody or functional fragment thereof, or a combination thereof, and recovering a population of CD1d-tet+ cells, a population of 6B11+ cells, or a combination thereof. In some embodiments, the sample is contacted with a binding molecule that specifically binds CD34 and recovering a population of CD34+ cells, thereby producing a population of HSPC. In some embodiments, the sample is contacted with a binding molecule that specifically binds CD3 and do not bind a binding molecule that specifically binds CD45RA, a binding molecule that specifically binds CD45RO, or a combination thereof, and recovering a population of CD3+ CD45RA− CD45RO+ cells. In some embodiments, the sample is contacted with a binding molecule that specifically binds CD4, a binding molecule that specifically binds CD25, a binding molecule that specifically binds CD127, a binding molecule that specifically binds CD45RA, a binding molecule that specifically binds CD45RO, or any combination thereof, and recovering a population of CD4+ CD25+ CD127−/lo CD45RA+ CD45RO− cells, a population of CD4+ CD25+ CD127−/lo CD45RA− CD45RO+ cells.

In any of the aforementioned embodiments, the therapeutic cell population comprises less than 2%, less than 1%, less than 0.5%, less than 0.1%, less than 0.01%, less than 0.001% naïve conventional αβ-T cells.

In any of the aforementioned embodiments, the Lin+ marker can be CD19, CD11c, CD66B, CD14, CD20, or any combination thereof.

In any of the aforementioned embodiments, the molecule that specifically binds a CD34, Lin+ marker, CD25, CD45RA, CDR45RO, CD4, CD8, CD127, CD90, CD133, CD38, CD95, CD122, CXCR3, LFA-1, CD62L, CCR7, or any other cellular marker is an antibody or an antibody fragment.

The term "antibody," as used herein, is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. It will be appreciated that the choice of epitope or region of the molecule to which the antibody is raised will determine its specificity, e.g., for various forms of the molecule, if present, or for total (e.g., all, or substantially all, of the molecule).

Methods for producing antibodies are well-established. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments that mimic antibodies can be prepared from genetic information by various procedures (Antibody Engineering: A Practical Approach (Borrebaeck, C., ed.), 1995, Oxford University Press, Oxford; J. Immunol. 149, 3914-3920 (1992)). Monoclonal and polyclonal antibodies to molecules, e.g., proteins, and markers also commercially available (R and D Systems, Minneapolis, Minn.; HyTest Ltd., Turk, Finland; Abcam Inc., Cambridge, Mass., USA, Life Diagnostics, Inc., West Chester, Pa., USA; Fitzgerald Industries International, Inc., Concord, Mass., USA; BiosPacific, Emeryville, Calif.).

In some embodiments, the antibody is a polyclonal antibody. In other embodiments, the antibody is a monoclonal antibody. In embodiments, the antibodies of the disclosure are compatible with downstream applications of the cell populations extracted according to the present methods. For example, the antibodies of the disclosure can be non-immunogenic, humanized antibodies. In some embodiments, the antibodies of the disclosure comprise an epitope tag useful to immobilize the antibody before or after extraction of the sample, thereby depleting the antibody from the extracted cell population.

In some embodiments, the antibody is a biotinylated 6B11 antibody. 6B11 is an antibody that binds to the invariant TCR Va24Ja18. In some embodiments, the 6B11 antibody is biotinylated at pH 5.5-6.0, 6.0-6.5, 6.5-7, 7.5-8, 8-8.5, 8.5-9, 9-9.5, or 9.5-10. In some embodiments, the 6B11 antibody is biotinylated in with buffering agents phosphate, borate, or hepes. In some embodiments, the buffer is an amine free buffer. The biotinylation reaction may be performed at about 0 mM NaCl, 50 mM NaCl, 100 mM NaCL, 150 mM NaCl, 300 mM NaCl, or 500 mM NaCl or intermediate values. Modification sites of the protein (e.g., antibody) include free amines, free thiols, and carbohydrates, artificially introduced azides, and artificially introduced alkynes. Concentrations of biotin may be varied from 10 μM-50 μM, 50 μM-100 μM, 100 μM-250 μM, 250 μM-500 μM, 500 μM-1 mM, 1 mM-2 mM, 2 mM-5 mM, 5 mM-10 mM. Reaction times may vary from 10-30 minutes, 30 minutes-1 hour, 1 hour 1.5 hours, 1.5 hours-2.5 hours, 2.5 hours-6 hours, 6 hours-10 hours, 10 hours-18 hours. The biotinylated 6B11 antibody disclosed herein may be used in any of the methods disclosed herein to sort, purify, or isolate populations of Va24Ja18+ cells (iNKT cells).

Capture binding partners and detection binding partner pairs, e.g., capture and detection antibody pairs, can be used in embodiments of the disclosure. Thus, in some embodiments, a sorting and purification protocol is used in which, typically, two binding partners, e.g., two antibodies, are used. One binding partner is a capture partner, usually immobilized on a particle, and the other binding partner is a detection binding partner, typically with a detectable label attached. Such antibody pairs are available from several commercial sources, such as BiosPacific, Emeryville, Calif. Antibody pairs can also be designed and prepared by methods well-known in the art. In a particular embodiment, the antibody is biotinylated or biotin labeled.

In some embodiments, there is a second imaging component that binds all members of the starting cell population non-specifically. Therefore, this signal can be read to normalize the quantity of fluorescence between cavities. One example is an antibody that will bind a protein or proteins that are ubiquitously expressed on the cell surface of a starting population of cells.

In some embodiments, the antibody or antibody fragment is coupled to or labeled with a fluorescent dye, a hapten, or a magnetic particle.

Several strategies that can be used for labeling binding partners to enable their detection or discrimination in a mixture of particles are well known in the art. The labels can be attached by any known means, including methods that utilize non-specific or specific interactions. In addition, labeling can be accomplished directly or through binding partners.

Emission, e.g., fluorescence, from the moiety should be sufficient to allow detection using the detectors as described herein. Generally, the compositions and methods of the disclosure utilize highly fluorescent moieties, e.g., a moiety capable of emitting electromagnetic radiation when stimulated by an electromagnetic radiation source at the excitation wavelength of the moiety. Several moieties are suitable for the compositions and methods of the disclosure.

Labels activatable by energy other than electromagnetic radiation are also useful in the disclosure. Such labels can be activated by, for example, electricity, heat or chemical reaction (e.g., chemiluminescent labels). Also, a number of enzymatically activated labels are well known to those in the art.

Typically, the fluorescence of the moiety involves a combination of quantum efficiency and lack of photobleaching sufficient that the moiety is detectable above background levels in the disclosed detectors, with the consistency necessary for the desired limit of detection, accuracy, and precision of the assay.

Furthermore, the moiety has properties that are consistent with its use in the assay of choice. In some embodiments, the assay is an immunoassay, where the fluorescent moiety is attached to an antibody; the moiety must have properties such that it does not aggregate with other antibodies or proteins, or experiences no more aggregation than is consistent with the required accuracy and precision of the assay. In some embodiments, fluorescent moieties dye molecules that have a combination of 1) high absorption coefficient; 2) high quantum yield; 3) high photostability (low photobleaching); and 4) compatibility with labeling the molecule of interest (e.g., protein) so that it can be analyzed using the analyzers and systems of the disclosure (e.g., does not cause precipitation of the protein of interest, or precipitation of a protein to which the moiety has been attached).

A fluorescent moiety can comprise a single entity (a Quantum Dot or fluorescent molecule) or a plurality of entities (e.g., a plurality of fluorescent molecules). It will be appreciated that when "moiety," as that term is used herein, refers to a group of fluorescent entities, e.g., a plurality of fluorescent dye molecules, each individual entity can be attached to the binding partner separately or the entities can be attached together, as long as the entities as a group provide sufficient fluorescence to be detected.

In some embodiments, the fluorescent dye molecules comprise at least one substituted indolium ring system in which the substituent on the 3-carbon of the indolium ring contains a chemically reactive group or a conjugated substance. Examples include Alexa Fluor molecules.

In some embodiments, the labels comprise a first type and a second type of label, such as two different ALEXA FLUOR® dyes (Invitrogen), where the first type and second type of dye molecules have different emission spectra.

A non-inclusive list of useful fluorescent entities for use in the fluorescent moieties includes: ALEXA FLUOR® 488, ALEXA FLUOR® 532, ALEXA FLUOR® 555, ALEXA FLUOR® 647, ALEXA FLUOR® 700, ALEXA FLUOR® 750, Fluorescein, B-phycoerythrin, allophycocyanin, PBXL-3, Atto 590 and Qdot 605.

Labels can be attached to the particles or binding partners by any method known in the art, including absorption, covalent binding, biotin/streptavidin or other binding pairs. In addition, the label can be attached through a linker. In some embodiments, the label is cleaved by the analyte, thereby releasing the label from the particle. Alternatively, the analyte can prevent cleavage of the linker.

The separated cell populations can be used immediately or can be cultivated in vitro after isolation using methods well known in the art. The cell populations can be cultured in media, such as RPMI-1640, DMEM, X-Vivo 10, X-vivo 15, or variants and combinations thereof. The media can comprise from 1-20% human serum. The media can comprise cytokines or molecules that activate the receptors for, such as, rapamycin, SCF, SDF-1, TPO, IL-2, IL-3, IL-4, IL-6, IL-7, IL-10, IL-15, IL-17, IL-18, IL-23, IL-33, TGF-b, IFNg, IFNa with combinations thereof. The cell populations can be stimulated with agonists such as particles (microparticles, nanoparticle, proteins, or cells) that contain multivalent display of binding molecules such as anti-CD3, anti-CD28, CD64, CD86, anti-IL-21R, CD137, or combinations thereof.

In addition, the cells can be frozen or they can be frozen before or after being separated. In case the cells are to be stored for a longer period of time it is preferred to do so at around −80° C. or in liquid nitrogen in order to in ensure that the cells can be used again after thawing. For this purpose, the cells are normally stored in DMSO and/or FCS/HS together with a medium, glucose etc. Immediately after the cells have been thawed, the cells can either be used directly for therapeutic purposes or in vitro experiments or they can be expanded and/or differentiated using growth factors, antigens, cells etc.

Example 1

Production of Sculpted Cellular Graft

The enrichment and depletion of cells occurs in multiple steps toward formulation of the final product for infusion. Each selection procedure is described in the following with a brief description of the procedure. This process is outlined in FIG. 14.

Step A:

$CD34^+$ cell enrichment was performed using immunomagnetic cell selection on the CLINIMACS Cell Selection System (Miltenyi Biotec, Bergish-Gladbach, Germany). Briefly, donor apheresis products were pooled, when two apheresis products were collected and washed to remove excess plasma and platelets. The volume was adjusted to that indicated for the cell number and $CD34^+$ cell content under the manufacturer's guidelines with CLINIMACS Buffer supplemented with 0.5% HSA (working buffer) and IVIg added to reduce non-specific binding of the Miltenyi microbead reagents to cells. The cellular product was labeled with CLINIMACS CD34 reagent using the manufacturer's guidelines for product content. Unbound reagent was reduced by dilution with working buffer and removal by centrifugation. The labeled cell product was connected to the CLINIMACS device, which controls the loading of the cells into the single use tubing set for immunomagnetic selection of the labeled cells. Retained cells were released by removal of the magnetic field and directed to the Positive Fraction bag attached to the CLINIMACS tubing set. The $CD34^+$ enriched cells were re-suspended in Normosol-R supplemented with 2% HSA as the designated infusion medium. The Negative fraction (CD34 selection flow-through) was retained for further cell processing.

Step B:

Regulatory T cells and iNKT cells were enriched from the Step A Negative fraction (CD34 selection flow-through) by immunomagnetic selection using the CLINIMACS system. The fraction volume was adjusted and the cells labeled with PE/Cy7-conjugated CD1d (glycolipid loaded) tetramer reagent and Miltenyi Biotec's anti-CD25 PE reagent. After washing to remove unbound reagent from the cell suspension, the cells were labeled with anti-PE microbead reagent, washed to remove unbound beads, and loaded onto the CLINIMACS using the LS tubing set. The labeled cells were retained on the magnetized column. Upon removal of the magnetic field, the $CD25^+$ and CD1d (glycolipid loaded) $tetramer^+$ cells were released from the column to the Positive fraction bag attached to the tubing set. The flow-through (Negative fraction) containing cells depleted of $CD25^+$ and CD1d (glycolipid loaded) $tetramer^+$ cells were retained for a subsequent cell selection procedure (Step C, below). The enrichment of $CD25^+$ cells and CD1d (glycolipid loaded) $tetramer^+$ cells was an intermediate step for further enrichment in Step D, below.

Step C:

Cells in the CD25/CD1d enrichment Negative fraction were separated into naïve and memory subsets by immunomagnetic selection using CD45RA expression as an indicator of donor memory cells. Cells were prepared and labeled with CLINIMACS CD45RA reagent. After washing to remove unbound reagent from the cell suspension, the cells were loaded in stages onto the CLINIMACS equipped with a depletion tubing set. The labeled cells were retained on the magnetized column and removed from the column to the Target Cell bag attached to the tubing set. The flow-through fraction contains cells depleted of $CD45RA^+$ cells were added to the final product to ensure inclusion of donor memory cells.

Step D:

Treg and iNKT cells were further purified by cell sorting using a BD FACS ARIA. The $CD25^+$ cells recovered by enrichment of $CD25^+$ and CD1d (glycolipid loaded)

tetramer⁺ cells in Step B were volume adjusted for labeling with PerCP-conjugated mouse anti-human CD4 and APC-conjugated mouse anti-human CD127 monoclonal antibody reagents and additional CD25 PE (Miltenyi Biotec) and CD1d (glycolipid loaded) tetramer PE-Cy7. After washing to remove unbound reagent, the cells were sorted with gates set for single, lymphocyte cells containing the molecular phenotype of CD4-PerCP⁺×CD25 PE+, CD127-APC dim/neg cells (Treg) and the CD127+×CD (glycolipid loaded) tetramer-PE/Cy7⁺ (iNKT).

Cell subsets recovered from cell selection procedures and intended for infusion were resuspended in Normosol-R, pH 7.2 (Hospira, Lake Forest, Ill.) supplemented with 0.5% HSA (Albumin-Human, 25%, Grifols, Clayton, N.C.). The cell fractions were combined in a single blood transfer bag at a maximum density of 1×10⁸ cell/ml and placed at 2 to 8° C. in a continuously monitored, secure refrigerator.

Example 2

Production of Sculpted Cellular Graft with Anti-iNKT Antibody

The enrichment and depletion of cells occurs in multiple steps toward formulation of the final product for infusion. Each selection procedure is described in the following with a brief description of the procedure. This process is outlined in FIG. 15.

Step A:

CD34⁺ cell enrichment was performed using immunomagnetic cell selection on the CLINIMACS Cell Selection System (Miltenyi Biotec, Bergish-Gladbach, Germany). Briefly, donor apheresis products were washed to remove excess plasma and platelets. If two donor apheresis products were collected they were pooled. The volume was adjusted to that indicated for the cell number CD34⁺ cell content under the manufacturer's guidelines with CLINIMACS Buffer supplemented with 0.5% HSA (working buffer) and IVIg added to reduce non-specific binding of the Miltenyi microbead reagents to cells. The cellular product was labeled with CLINIMACS CD34 reagent using the manufacturer's guidelines for product content. Unbound reagent was reduced by dilution with working buffer and removal by centrifugation. The labeled cell product was connected to the CLINIMACS device, which controls the loading of the cells into the single use tubing set for immunomagnetic selection of the labeled cells. Retained cells were released by removal of the magnetic field and directed to the Positive Fraction bag attached to the CLINIMACS tubing set. The CD34⁺ enriched cells were re-suspended in Normosol-R supplemented with 2% HSA as the designated infusion medium. The Negative fraction (CD34 selection flow-through) was retained for further cell processing.

Step B:

Regulatory T cells and iNKT cells were enriched from the Step A Negative fraction (CD34 selection flow-through) by immunomagnetic selection using the CLINIMACS system. The fraction volume was adjusted and the cells labeled with anti-CD25-PE (Miltenyi Biotec) and biotin conjugated 6B11 monoclonal antibodies (anti-iNKT). After washing to remove unbound reagent from the cell suspension, the cells were labeled with PE/Cy7-conjugated streptavidin and washed again. The cells were then labeled with anti-PE microbead reagent (Miltenyi Biotec), washed to remove unbound beads, and loaded onto the CLINIMACS using the LS TS tubing set using the CD133 enrichment program. The labeled cells were retained on the magnetized column. Upon removal of the magnetic field, the CD25⁺ and 6B11⁺ cells were released from the column to the target fraction bag attached to the tubing set. The flow-through (non-target fraction) containing cells depleted of CD25⁺ and 6B11⁺ cells were retained for a subsequent cell selection procedure (Step D, below). The enrichment of CD25⁺ cells and 6B11⁺ cells is an intermediate step for further enrichment in Step C, below.

Step C:

Treg and iNKT cells were further purified by fluorescence activated cell sorting. The CD25⁺ cells recovered by enrichment of CD25⁺ and 6B11⁺ cells in Step B were volume adjusted for labeling with PerCP-conjugated mouse anti-human CD4 (Miltenyi Biotec) and APC-conjugated mouse anti-human CD127 monoclonal antibody reagents (Miltenyi Biotec), and additional CD25 PE (Miltenyi Biotec) and Streptavidin PE-Cy7. After washing to remove unbound reagent, the cells were sorted with gates set single, lymphocyte cells containing the molecular phenotype of CD4-PerCP⁺×CD25 PE+, CD127-APC dim/neg cells (Treg) and the CD127+×6B11-PE/Cy7⁺ (iNKT).

Step D:

Cells in the CD25/6B11 Negative fraction were separated into naïve and memory subsets by immunomagnetic selection using CD45RA expression as an indicator of donor memory cells. Cells were prepared and labeled with CLINIMACS CD45RA reagent. After washing to remove unbound reagent from the cell suspension, the cells were loaded in stages onto the CLINIMACS equipped with a depletion tubing set. The labeled cells were retained on the magnetized column and removed from the column to the Target Cell bag attached to the tubing set. The flow-through fraction contains cells depleted of CD45RA⁺ cells were added to the final product to ensure inclusion of donor memory cells.

Cell subsets recovered from cell selection procedures and intended for infusion were resuspended in Normosol-R, pH 7.2 (Hospira, Lake Forest, Ill.) supplemented with 0.5% HSA (Albumin-Human, 25%, Grifols, Clayton, N.C.). The cell fractions were combined in a single blood transfer bag at a maximum density of 1×10⁸ cell/ml and placed at 2 to 8° C. in a continuously monitored, secure refrigerator.

TABLE 1

Reagents and target cells numbers for an exemplary sculpted graft composition.

| Sculpted Graft Component | Molecular Phenotype for Sculpted Graft Isolation | Exemplary Isolation Reagents | Dosage: Number of Cells/kg |
|---|---|---|---|
| HSPC | CD34⁺ | Anti-CD34+ microbeads (Miltenyi) | $1 \times 10^6$-$1 \times 10^7$ |

TABLE 1-continued

Reagents and target cells numbers for an exemplary sculpted graft composition.

| Sculpted Graft Component | Molecular Phenotype for Sculpted Graft Isolation | Exemplary Isolation Reagents | Dosage: Number of Cells/kg |
|---|---|---|---|
| Treg | $CD34^-$ $CD4^+$ $CD25^+$ $CD127^{dim/-}$ | Anti-CD4 PerCP Anti-CD25 PE (Miltenyi) Anti-CD127 APC (Miltenyi) Anti-PE microbeads | $0.5 \times 10^6\text{-}5 \times 10^6$ |
| iNKT | $CD34^-$ TCR Vα24Jα18$^+$ $CD127^+$ | 6B11-biotin Streptavidin PE-Cy7 Anti-CD127 APC (Miltenyi) Anti-PE microbeads | $1 \times 10^4\text{-}2.5 \times 10^6$ |
| Tmem | $CD34^-$ $CD25^-$ $CD45RA^-$ | Anti-CD45RA | $1 \times 10^6\text{-}1 \times 10^8$ |
| Tnaive (contaminant) | $CD34^-$ $CD25^-$ $CD45RA^+$ | Anti-CD45RA | <75,000 |

Example 3

Sculpted Cellular Graft Versus T Cell Replete & T Cell Depleted Allografts in a Murine Model of Myeloablative Hematopoietic Cell Transplant (AlloMA-HCT)

Figure 16:
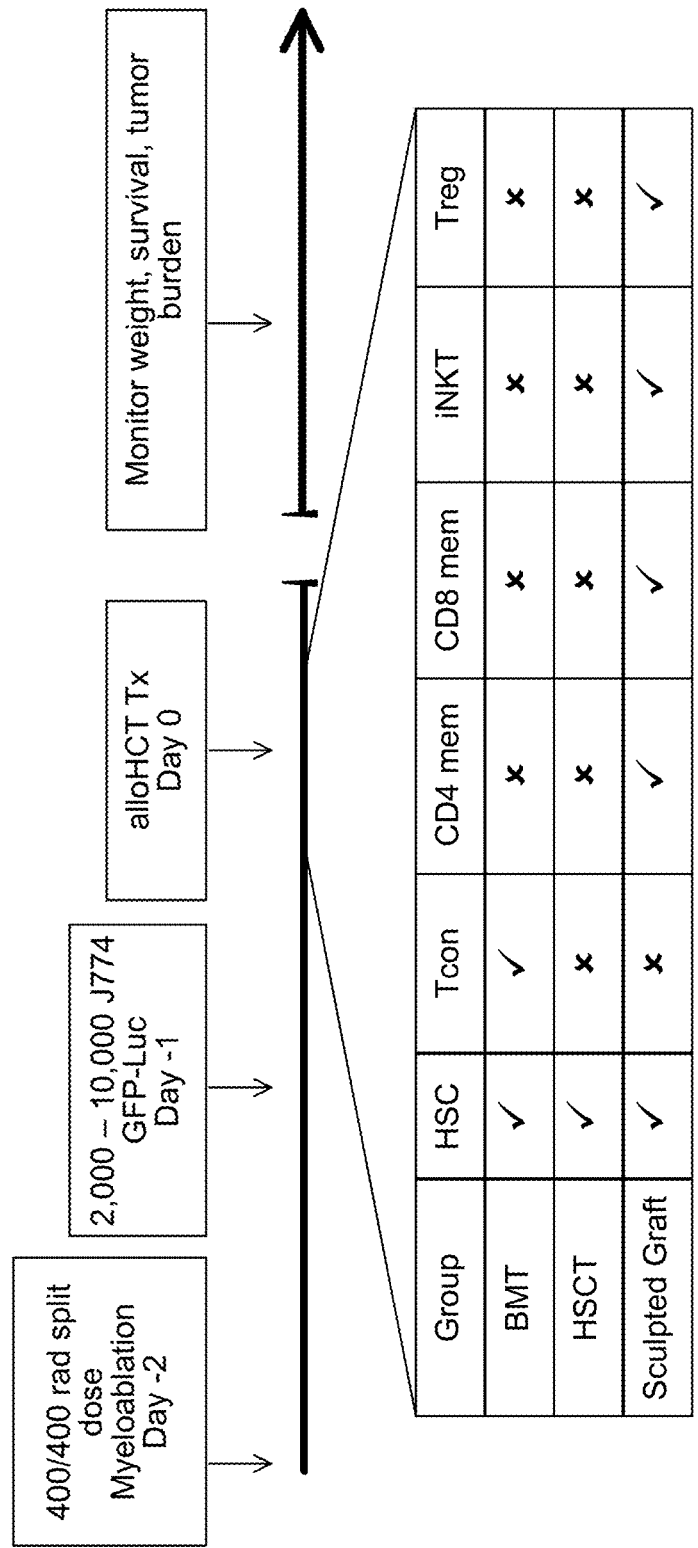
FIG. 16 depicts an experimental design to assess the performance of a sculpted cellular graft compared to bone marrow transplant (BMT) and hematopoietic stem cell transplant (HSCT) compositions.
Figure 17A:
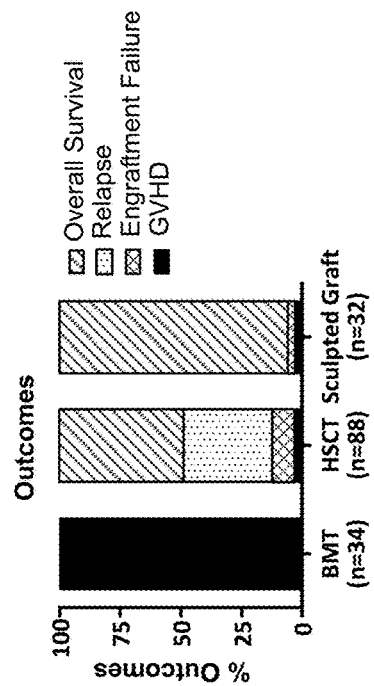
FIG. 17A-D shows the performance of a sculpted cellular graft compared to bone marrow transplant (BMT) and hematopoietic stem cell transplant (HSCT) compositions.
Figure 17B:
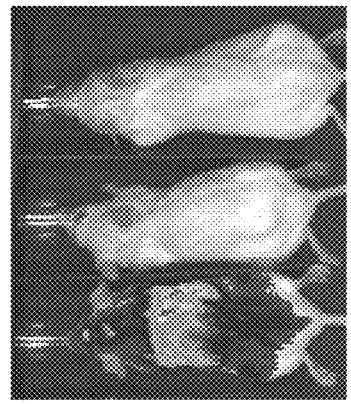
Figure 17C:
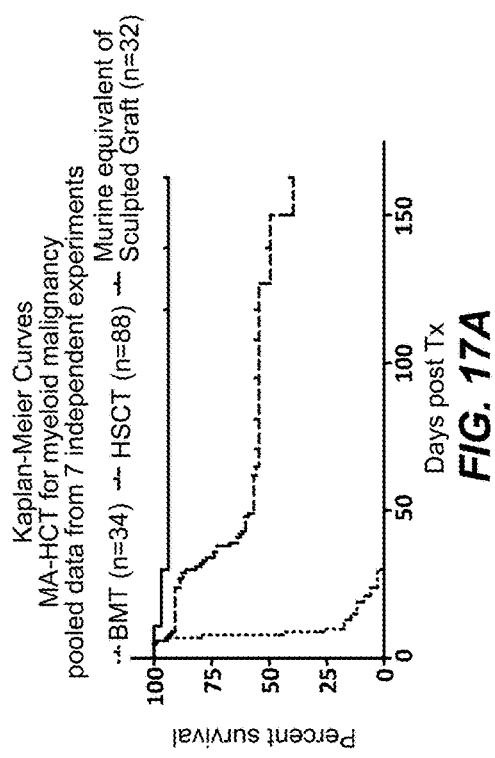
Figure 17D:
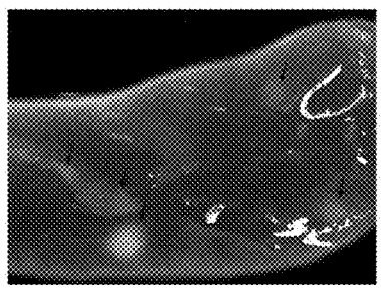

A murine model of myeloablation and cellular graft transplant was used to assess the performance of an exemplary sculpted cellular graft described herein compared to known cellular grafts. FIG. 16 depicts a diagram of the experimental procedure. To model myeloablated patients, 8-12 week old BALB/c recipient mice were weighed and then irradiated with a split dose of 400/400 rad from a Rad-Source RS2000 irradiator at 160 KeV filtered through 0.5 mm Cu on day −2. Mice were switched to antibiotic food for 6 weeks. To model residual disease, 2,500-10,000 J774 GFP-Luc cells were injected intravenously into each mouse via the tail vein on day −1. The J774 cell line is a myeloid cell line originally derived from BALB/c mice and are syngeneic to the BALB/c recipient mice. The J774 cells were modified to express a GFP and Luciferase transgene. The three different cellular compositions summarized in Table 2 were used to model allogeneic hematopoietic cell transplantation (HCT). The cellular compositions were prepared as described below from the hematopoietic tissue of C57Bl/6 mice and infused intravenously through the retro-orbital plexus of the BALB/c mice on day 0. Experimental cohorts were generally 5-9 mice. Data from seven independent experiments were pooled and represented in the FIG. 17.

TABLE 2

Cellular compositions administered to BALB/c mice.

| Cellular Composition | Cell Types |
|---|---|
| Bone Marrow Transplant (BMT) | HSPC: $1 \times 10^6\text{-}2 \times 10^6$ cKIT$^+$ magnetically enriched bone marrow cells Tcon: $1 \times 10^5\text{-}1 \times 10^7$ splenocytes |
| Hematopoietic Stem Cell Transplant (HSPT) | HSPC: $1 \times 10^6\text{-}2 \times 10^6$ cKIT$^+$ magnetically enriched bone marrow cells |
| Sculpted Cellular Graft | HSPC: $1 \times 10^6\text{-}2 \times 10^6$ cKIT$^+$ magnetically enriched bone marrow cells Treg: $5 \times 10^3\text{-}5 \times 10^4$ FACS sorted CD4$^+$CD25$^{bright}$ splenocytes iNKT: $1 \times 10^4\text{-}1 \times 10^6$ FACS sorted CD1d-tetramer$_{PBS\text{-}57\ loaded}$ + splenocytes |

TABLE 2-continued

Cellular compositions administered to BALB/c mice.

| Cellular Composition | Cell Types |
|---|---|
| | CD8 Tmem: $2.5 \times 10^4\text{-}1.25 \times 10^5$ FACS sorted CD8$^+$CD44$^+$CD62L$^{mid/low}$ splenocytes CD4 Tmem: $7.5 \times 10^4\text{-}3.75 \times 10^5$ FACS sorted CD4$^+$CD44$^+$CD62L$^{mid/low}$ splenocytes |

Mice were checked daily for distress. Body condition (BC) score and body weights were measured twice weekly. Mice with BC≤1.5 were euthanized. Mice that died with body weights <70% of their original weight were scored as GVHD. Mice that died within 30 days post-transplant >70% body weight were scored engraftment failure. All dead mice were dissected and inspected for tumor growth in liver and spleen with a fluorescent microscope. The presence of GFP+ tumor nodules was scored as relapse (see FIG. 17C). Some cohorts of mice were subjected to bioluminescent imaging on a Xenogen IVIS100 on day +10 (see FIG. 17D).

Mice receiving the sculpted cellular graft composition outperformed all other cohorts (see FIGS. 17A and B). 94% of these mice survived to day +175 with no evidence of relapse. 3% of these mice died from GVHD and 3% died from engraftment failure. The improved performance compared to BMT and HSPC compositions indicates that the GvL effect has been maintained, but the GVHD and engraftment failure rates are significantly reduced.

In comparison, all mice receiving a BMT composition of cells succumbed to GVHD before day +30. No evidence of relapse was found in these mice in bioluminescent imaging at day +10. Furthermore, no tumor nodule growth on the hematopoietic organs was observed in post mortem analysis. This result indicates the T cells in the graft were sufficient to counteract the cancer cells, and indicates strong GvL from the graft albeit in the background of uniformly lethal GVHD. It is noted that in human patients, allograft sources are closely matched to the recipient by HLA-haplotype, whereas BALB/c and C57Bl/6 mice are fully mismatched. Therefore, the GVHD reaction observed in the clinic is strongly mitigated relative to the GVHD reaction observed here.

Mice receiving a HSCT composition of cells had mixed outcomes. 51% of mice survived long term to day +175. 9% of HSCT recipients died from engraftment failure as evidenced by death before day +30 at a body weight >70%. 3% of mice died from GVHD, as evidenced as body weight <70% at the last measurement before the time of death. 36% of mice had evidence of relapse at the time of death. The high rate of relapse in this cohorts results from prolonged immunosuppression after HSCT, as T cell counts remain low in the early weeks after transplant. In comparison, human HSCT recipients also suffer low T cell counts for the first year after transplant and higher rates of relapse. Therefore, the HSCT transplant model mirrors the lack of GvL in human patients due to T cell depletion. An increased relapse rate is observed in human patients treated with $CD34^+$ allografts relative to T cell-replete allografts.

Example 4

Comparison of Sculpted Cellular Grafts Produced by MACS/FACS Vs MACS-Only a Murine Model of AlloMA-HCT This experiment compares the sculpted cellular graft composition data shown above with another cohort of mice. GVL and GVHD were assessed in animals treated with a sculpted cellular graft produced by MACS-only or a sculpted cellular graft produced by combination of MACS and FACS (see Table 3). These mice were prepared and followed as above. Cohorts were 5-7 mice and the data is pooled from 3 independent experiments.

TABLE 3

Sculpted cellular graft produced by MACS-only or a combination of MACS and FACS

| Cellular Composition | Cell Types |
|---|---|
| MACS-only Sculpted Cellular Graft | HSPC: $1 \times 10^6$-$2 \times 10^6$ $cKIT^+$ magnetically enriched bone marrow cells<br>Treg: $5 \times 10^3$-$5 \times 10^4$ magnetically enriched $CD25^+$ splenocytes<br>iNKT: $1 \times 10^4$-$1 \times 10^6$ magnetically enriched CD1d-tetramer$_{PBS-57\ loaded}$ + splenocytes<br>Tmem: $2.5 \times 10^4$-$1.25 \times 10^5$ magnetically enriched $CD44^+$ splenocytes |
| MACS/FACS Sculpted Cellular Graft | HSPC: $1 \times 10^6$-$2 \times 10^6$ $cKIT^+$ magnetically enriched bone marrow cells<br>Treg: $5 \times 10^3$-$5 \times 10^4$ FACS sorted $CD4^+CD25^{bright}$ splenocytes<br>iNKT: $1 \times 10^4$-$1 \times 10^6$ FACS sorted CD1d-tetramer$_{PBS-57\ loaded}$ + splenocytes<br>CD8 Tmem: $2.5 \times 10^4$-$1.25 \times 10^5$ FACS sorted $CD8^+CD44^+CD62L^{mid/low}$ splenocytes<br>CD4 Tmem: $7.5 \times 10^4$-$3.75 \times 10^5$ FACS sorted $CD4^+CD44^+CD62L^{mid/low}$ splenocytes |

Figure 18:
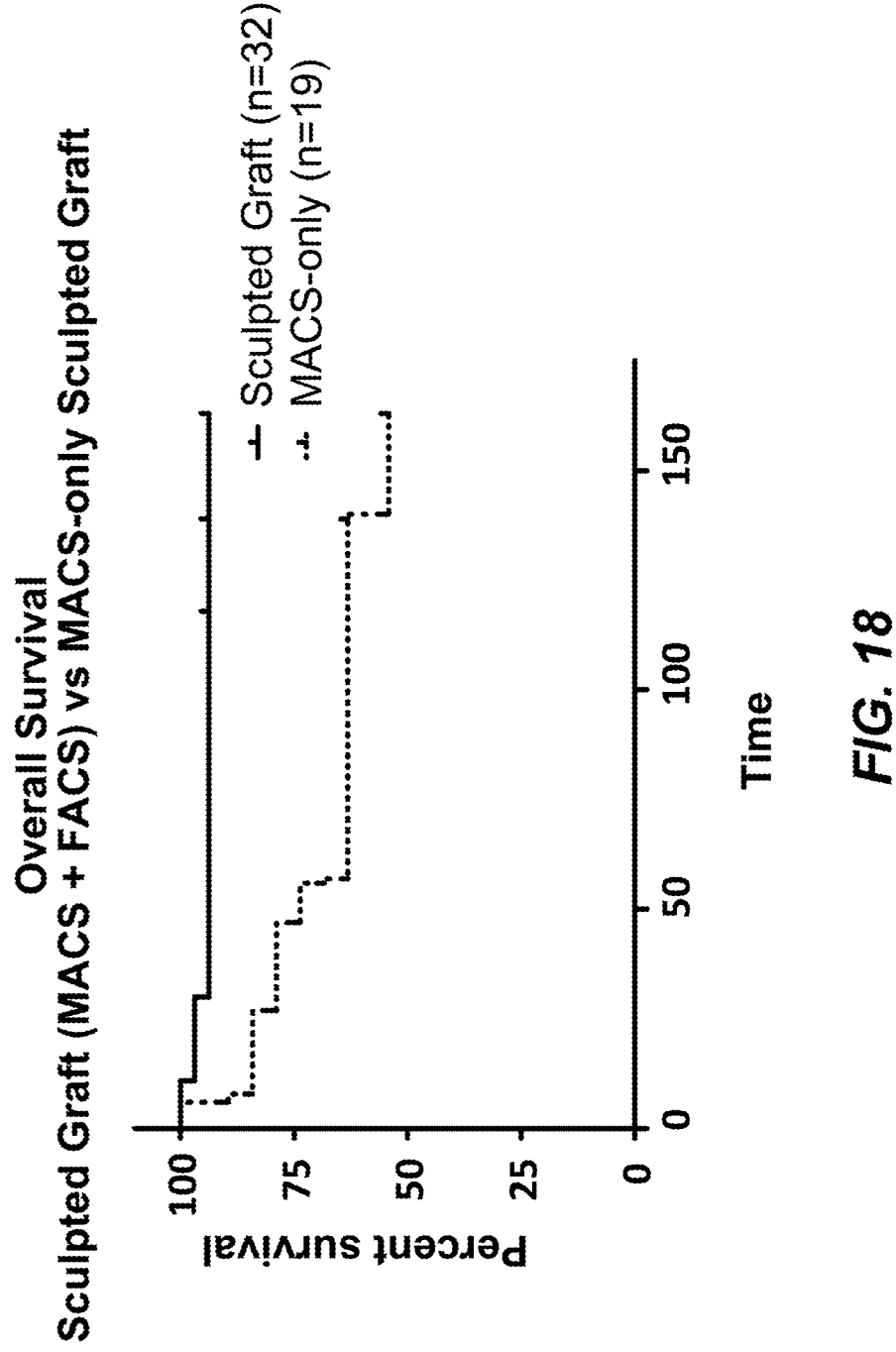
FIG. 18 depicts Kaplan-Meier curves of percent survival of mice treated with a sculpted cellular graft produced with magnetic sorting (MACS) and fluorescence activated sorting (FACS) in comparison to a sculpted cellular graft produced with MACS-only.

The MACS/FACS sculpted cellular graft mice were prepared using a combination of MACS and FACS as described in Example 3. FACS purities are typically greater than 95%. In comparison, the purity of MACS-only enriched samples is typically 20%-80%. The allogeneic lymphocytes of the MACS-only mice were not further purified by FACS, and the therapeutic benefit of this composition was severely impaired. Only 54% of MACS-only mice were alive by day +175 compared to 94% survival of MACS/FACS sculpted cellular graft mice (see FIG. 18). All fatal cases exhibited body weights <70% of the starting weight, indicating GVHD as the cause of death. None of these mice showed post-mortem evidence of relapse. The high levels of lethal GVHD in the MACS-only manufacturing compared to the MACS/FACS method of manufacturing demonstrate the importance of purity for these cell populations in the context of graft-engineering of a myeloablative hematopoietic cell transplant (MA-HCT). While not wishing to be bound by theory, the prevalence GVHD in mice treated with the MACS only sculpted cellular graft is thought to be the result of contamination Tcon cells.

Example 5

Comparison of Sculpted Cellular Graft Vs BMT with T Cell Add-Back in a Murine Model of AlloMA-HCT A sculpted cellular graft composition was compared against cohorts that were administered BMT compositions with varying amounts of T cells added to the cKIT+ HSPC fraction (HSPC+T cell add-back). By way of background, T cell add-back is an experimental clinical approach to bone marrow transplant. As an example, clinical centers perform a T cell depletion (e.g., usually a CD34+ cell CLINIMACS isolation), and then add back some of the T cells to the graft or transplant them at a later date. Note that in the add-back procedure the T cells are bulk T cells, as T cells are provided from the collected $CD34^-$ fraction and are not further processed. T cells are typically reintroduced at levels 10-1000 times less than the naturally occurring level in a BMT graft.

In the instant example, each add-back cohort was administered a cKIT+ HSPC fraction that contained $1 \times 10^5$, $2 \times 10^5$, $4 \times 10^5$, or $2 \times 10^6$ add-back T cells from splenocytes. In comparison, the sculpted cellular graft contained a mean of $2.5 \times 10^5$ T cell. However, some sculpted cellular graft experiments employed as many as $5 \times 10^6$ sculpted T cells and others as few as $1 \times 10^5$ sculpted T cell.

Figure 19:
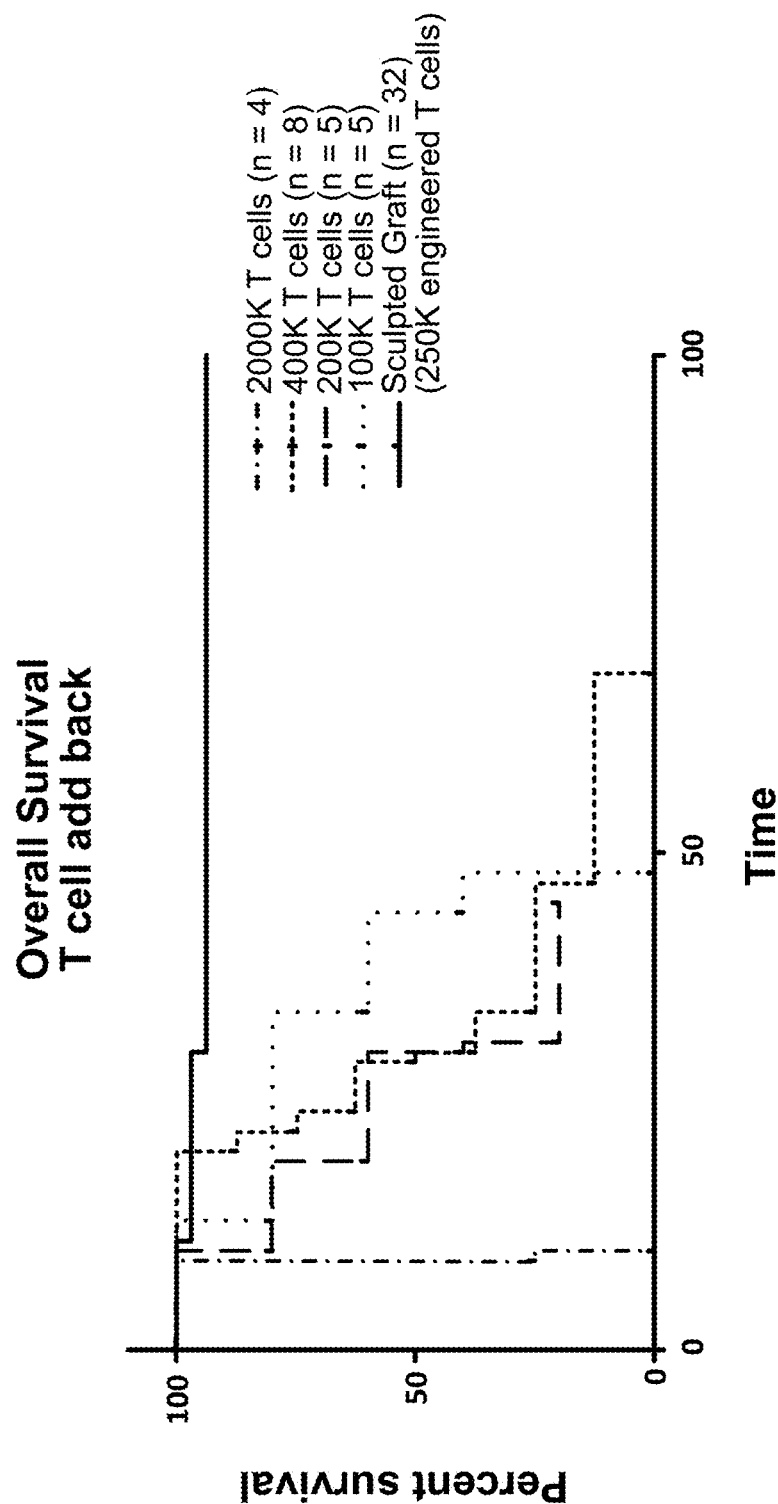
FIG. 19 depicts Kaplan-Meier curves showing survival of mice that were administered a sculpted cellular graft versus mice administered CD34$^+$ cellular compositions that include T cells added back after isolation.

In the context of fully mismatch C57Bl/6 lymphocytes adoptively transferred into BALB/c mice, even $1 \times 10^5$ T cells was sufficient to induce lethal GVHD in 100% of the recipients (FIG. 19). Note that the time to death was prolonged in mice that were administered between $1 \times 10^5$ and $4 \times 10^5$ add-back T cells, but no mouse survived long-term. In contrast, 94% (30/32) of the sculpted cellular graft treated mice demonstrated long term survival to day +175. None of the mice displayed post-mortem evidence of relapse. Therefore, the T cell component of the sculpted cellular graft composition both mitigates the GVHD response and imparts a GVL therapeutic benefit. A similar result is not observed by a simply adding back a reduced number of T cells to cKIT+ magnetically enriched bone marrow cells.

Example 6

Delayed Time to Onset of GVHD with Human-Derived Sculpted Cellular Grafts Vs Unprocessed PBMCs in a Xenograft Model of Allo-HCT White blood cell concentrate of TrimaAccel® LRS chamber were recovered after Plateletpheresis procedure from 4 human donors. Red blood cells were removed by a density gradient (Ficoll) and ACK lysis. The resulting PBMCs were washed and $2.5 \times 10^8$ cells from each donor were processed sculpted cellular graft lymphocyte fractions. More specifically, Tregs and iNKTs were initially processed using MACS (i.e., rough sorting). The samples were stained with anti-CD25 PE and the biotin conjugated anti-iNKT antibody, 6B11, and then washed; stained with Streptavidin PE-Cy7 and then washed again; and stained with anti-PE microbeads. The sample was then positively enriched using a Possel_S program on a Miltenyi AutoMACS. The positively enriched fraction was further stained with anti-CD127 APC and anti-CD4 PerCP and further purified on a BD FACSAriaII to >98% purity according to the parameters: Treg: $CD4^+CD25^+CD127^-$ and iNKT: $CD127^+6B11^+$.

The negative fraction from the AutoMACS column was further stained with anti-CD45RA microbeads and the Deplete_S program was used to deplete the naïve T cells in the CD45RA+ fraction. The remaining cells were CD45RA-CD45RO+, which is indicative of memory T cells.

Sculpted cellular grafts were formulated based on the final yield of each subtype which varied between donors. PBMC cohorts were formulated to match an equal number of $CD3^+$ T cells with the number of memory T cells in the sculpted cellular graft composition from the matched donor. The final formulations ranges are represented in Table 4.

TABLE 4

Lymphocyte formulations

| Sculpted Cellular Graft Lymphocytes/Mouse | PBMC/mouse |
|---|---|
| $7.5 \times 10^4$-$1.5 \times 10^5$ Treg | $2 \times 10^6$-$6 \times 10^6$ Total Nucleated Cell |
| $5 \times 10^3$-$1.5 \times 10^4$ iNKT | Count ($1 \times 10^6$-$3 \times 10^6$ $CD3^+$) |
| $1 \times 10^6$-$3 \times 10^6$ Memory T cells | |

Figure 20:
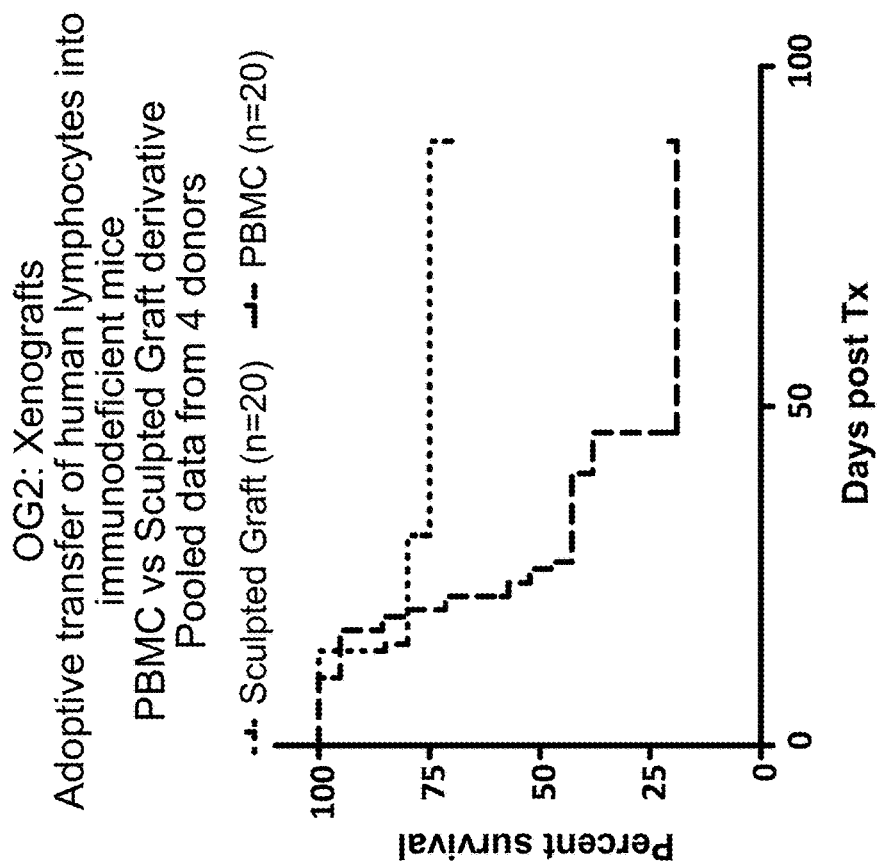
FIG. 20 depicts Kaplan-Meier curves showing survival mice in a xenograft model of adoptive transfer wherein the cohorts of mice were administer either a human PBMCs or a sculpted cellular graft composition derived from human tissue.

For the Xenograft experiments, immunodeficient (NSG) mice were used because a functional murine immune system would quickly reject the incoming human tissue based on species-specific differences. NSG mice lack B, T, and NK cells making it a suitable host for xenograft experiments. To further prepare the host to engraft lymphocytes, the mice are given a non-lethal dose of radiation. NSG were irradiated with 250 rad from a Rad-Source RS2000 irradiator at 160 KeV filtered through 0.5 mm Cu and switched to antibiotic feed. On the same day the formulated cells were injected into 5 mice per cohort for each donor and tracked as described above. In this context, human PBMCs are known to elicit a robust GVHD response. The results demonstrate that 70% of the mice receiving the sculpted cellular graft lymphocytes survive to day +90, compared to only 15% of mice receiving an equal dose of CD3+ cells in the PBMCs (see FIG. 20). GVHD was scored as the cause of death in all cases of death. The xenogeneic response of human lymphocytes against murine tissue is robust; however, the sculpted cellular graft does not only delay the onset of lethal GVHD (which would have clinical value), but rather it results in durable survival for a significant fraction of the mice.

Example 7

Isolation of Regulatory T Cells and iNKTs

The following experiments demonstrate methods for producing Treg and iNKT cell fractions for use in a sculpted cellular graft composition and therapy. Peripheral blood monocytes (PBMCs) were isolated from buffy coat LRS chambers as in Example 6 from 3 donors. The PBMCs were pooled and then resuspended and stained at a concentration of $2 \times 10^8$ cells/ml. Tregs were stained with anti-CD25 PE and iNKT cells were stained the biotin conjugated 6B11 antibody (anti-iNKT) for 30 minutes at room temperature, washed, and then stained with Streptavidin PE-Cy7 for 10 minutes at room temperature. Excess antibody was removed by washing the cells with buffer before staining with anti-PE microbeads at $2 \times 10^8$ cells/mL. Cells were stained with the anti-PE microbeads for 30 minutes at room temperature. After staining, cells were washed with buffer and filtered through a 40 micron pore mesh to remove clumps before separation. A CLINIMACS LS TS tubing set was used to sort the cells using the manufacturer's CD133 enrichment protocol (loading speed: 10 mL per min, 3 re-loads). The Treg and iNKT enriched cells were collected in the positive fraction and the remaining cells were collected in the negative fraction. A fraction of known volume relative to the measured volume of the sample of each sample was removed and counted on a Beckman Coulter Cytoflex using reference beads and used to calculate yields.

The performance of the separation of Tregs and iNKT cells from PBMCs was assessed by calculating the purity and yield of Treg and iNKT cells in the enriched fraction relative to the pre-enriched cells. In a representative experiment using anti-PE beads, the purity of Tregs increased from about 5% to 60%, (FIG. 21A and Table 5). The anti-PE beads tested increased the purity of the NKT cells from 0.02% to 0.04% (FIG. 21B and Table 6).

TABLE 5

Percent purity and yield of Treg cells.

| CliniMACS Enrichment | anti PE bead/ million cells | Purity (%) | Yield (%) |
|---|---|---|---|
| Expt 1 | 0.1 µl | 57.4 | 31.3 |
| Expt 2 | 0.2 µl | 38.9 | 39.2 |
| Expt 3 | 0.5 µl | 32.3 | 37.4 |

TABLE 6

Percent purity and yield of iNKT cells

| Enrichment Program | anti PE bead/ million cells | Purity (%) |
|---|---|---|
| Expt 1 | 0.1 ul | 0.04 |
| Expt 2 | 0.2 ul | 0.03 |
| Expt 3 | 0.5 ul | 0.04 |

These data demonstrate that by carefully titrating the magnetic selection reagent, higher purities of enriched cells can be obtained without adversely compromising the yield. In addition, that the negative fraction can be re-processed with similar or identical conditions as the crude PBMC product to recover more target cell. This unexpected finding enables a process that meets the target specifications for the post-CLINIMACS Treg/iNKT fraction.

Example 8

Isolation of Memory T Cells

Figure 22A:
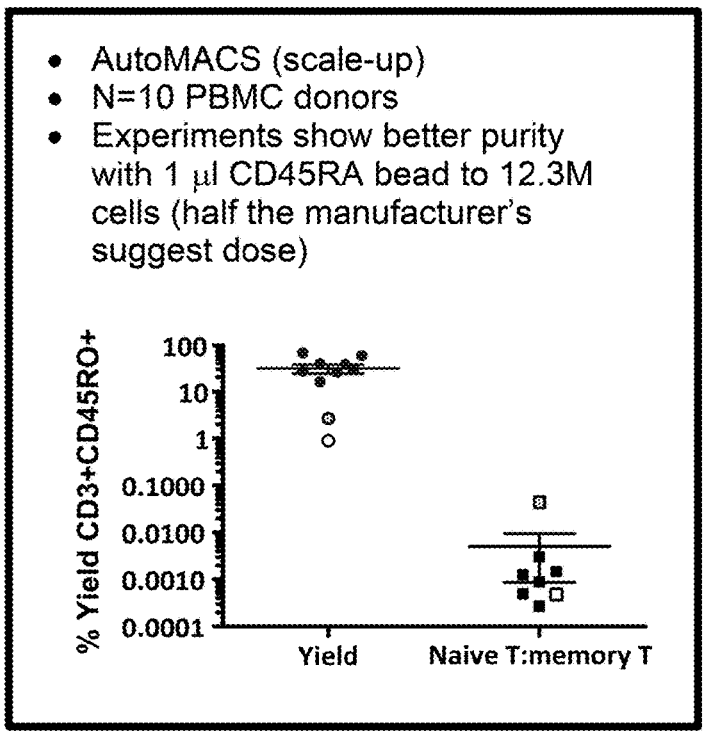
FIG. 22A-B depicts enrichment of memory T cells from PBMCs using magnetic sorting.
Figure 22B:
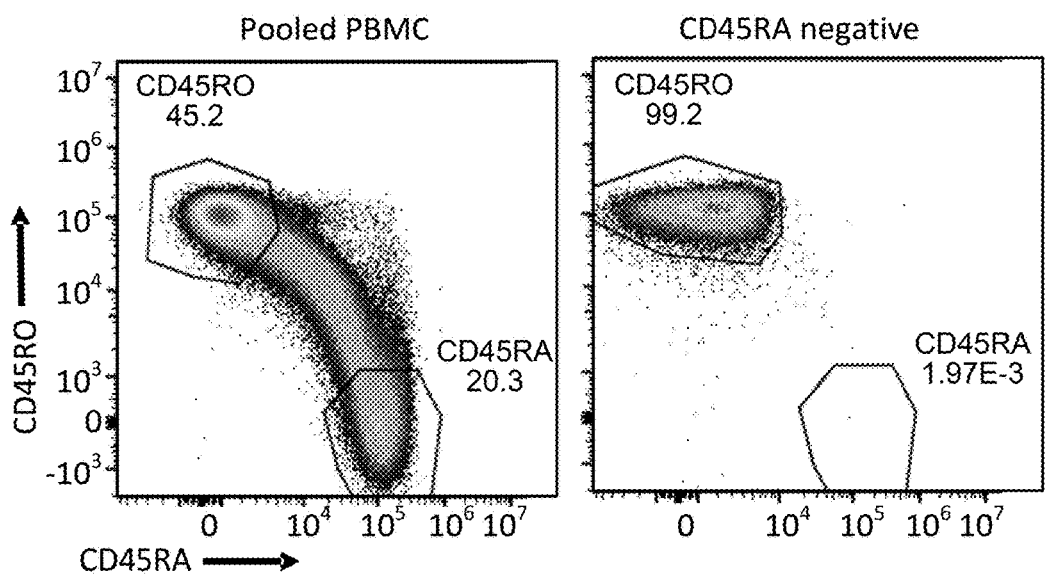

PBMCs were isolated from buffy coat LRS chambers as in Example 6 from 3 donors. The PBMCs were pooled and then $1 \times 10^9$ cells were resuspended at $2 \times 10^8$ cells/mL. The cells were stained with half of the manufacturer's recommended usage of CD45RA microbeads (0.5 µL anti-CD45RA per $6.6 \times 10^6$ PBMCs rather than 1.0 µL anti-CD45RA per $6.6 \times 10^6$ PBMCs). The cells were washed and run on CLINIMACS Depletion 2.1 (6 mL/min flow rate). Both positive and negative fractions were harvested and analyzed. A fraction of known volume relative to the measured volume of the sample fraction of each sample was removed and stained with fluorescently conjugated monoclonal antibodies against CD3, CD45RA, and CD45RO, washed, and counted on a Beckman Coulter CYTOFLEX flow cytometer using reference beads to calculate purity and yields (FIG. 22).

The performance of the separation of naïve T cells (Tn) and memory T cells was assessed by calculating the purity and yield of $CD3^+CD45RA^+$ and $CD3^+CD45RO^+$ cells in the enriched fraction relative to the pre-enriched cells. Using half the manufacturer recommended dosage of CD45RA microbeads, the ratio of Tmem to Tn went from 2.25:1 in the starting PBMC sample to 50298:1 in the processed sample (Table 7). Furthermore, the yield of Tmem after this process was 27.5%. These studies demonstrate the feasibility of manufacture of a sculpted cellular graft with a reduced amount of CD45RA microbeads.

TABLE 7

Performance of memory T cell enrichment using magnetic sorting to depleted $CD45RA^+$ cells

| CD45RA depletion | Tmem:Tn | Yield |
| --- | --- | --- |
| 1 µl reagent per 12.3M | 50298 | 27.5% |
| Target | 10000 | 66.0% |
| Min | 10000 | 22.0% |

Example 9

Isolation of Regulatory T Cells and Naïve Regulatory T Cells

The following experiment characterizes Treg populations produce an exemplary method disclosed herein. PBMCs were isolated from buffy coat LRS chambers as in Example 6 from 2 donors. The PBMCs were pooled and then resuspended and stained at a concentration of $2 \times 10^8$ cells/ml. Tregs sorted using anti-CD25 magnetic microbeads. A CLINIMACS LS TS tubing set was used to sort the cells using the manufacturer's CD133 Depletion protocol (loading speed: 10 mL per min, 3 re-loads). The Treg enriched cells were collected in the positive fraction and the remaining cells were collected in the negative fraction.

The Treg enriched fraction was stained with anti-CD25 PE, CD4PerCP, CD127APC, CD45RA-FITC, and CD45RO-APC-Cy7 according to the manufacturer's instructions. Excess antibody was removed by washing the cells with buffer. The Treg enriched fraction was counted on a Beckman Coulter Cytoflex using reference beads and used to calculate percent purity and yield. The performance of the separation of Tregs from PBMCs was assessed by calculating the purity and yield of Treg cells in the enriched fraction relative to the pre-enriched cells.

Figure 23A:
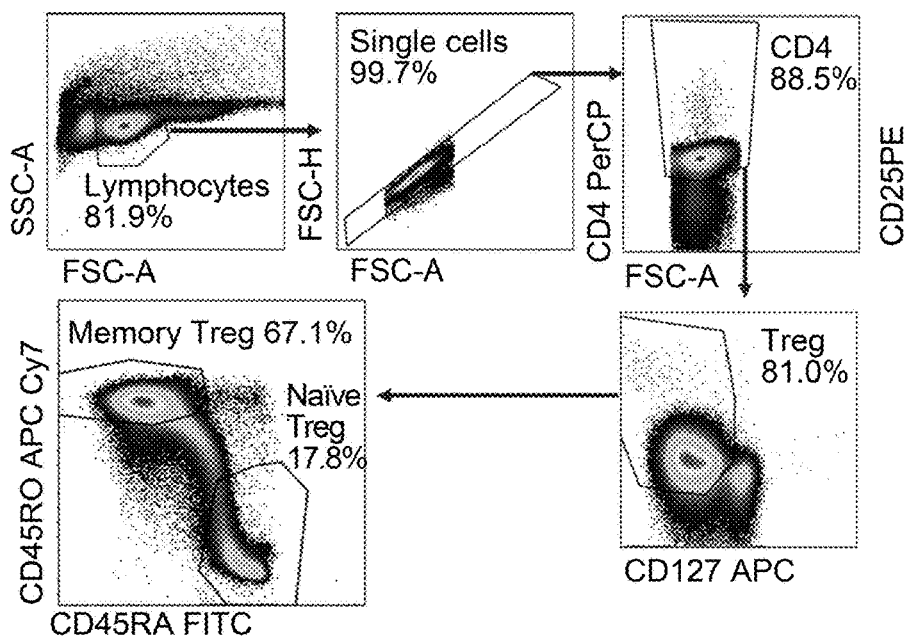
FIG. 23A-B depicts magnetic separation of CD25$^+$ cells.
Figure 23B:
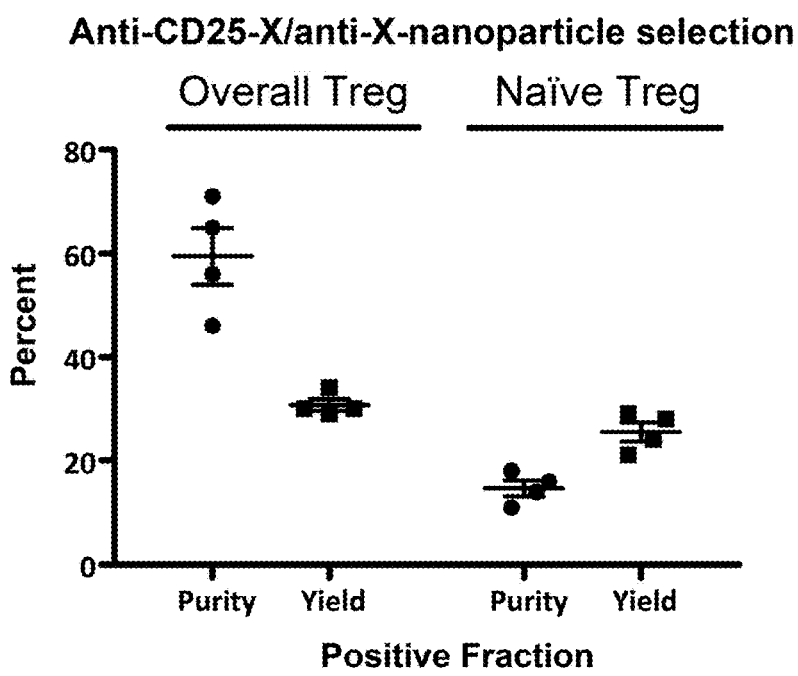

FIG. 23A demonstrates that the Treg positive fraction comprised 88.5% $CD4^+CD25^+$ cells, of which 81.0% were $CD127^+$. In addition, FIG. 23A demonstrates that the $CD4^+CD25^+CD127^+$ cell population (Tregs) comprise 67.1% memory Treg ($CD45RO^+$) and 17.8% naïve Treg ($CD45RA^+$). FIG. 23B provides a summary of the purity and yield of overall Tregs and Naïve Tregs in the Treg positive fraction.

This data demonstrates that the methods described herein provide a population of Tregs that include a significant number of naïve Tregs that would otherwise be lost during a CD45RA depletion step.

Example 9

Biotinylation of 6B11

6B11 is an antibody that binds to the invariant TCR Va24Ja18. However, the potency and specificity of this reagent when conjugated to secondary fluorophores or other molecular handles is of poor performance in general. However, when biotinylation conditions are varied using an unexpectedly good performance can be achieved.

Figure 24A:
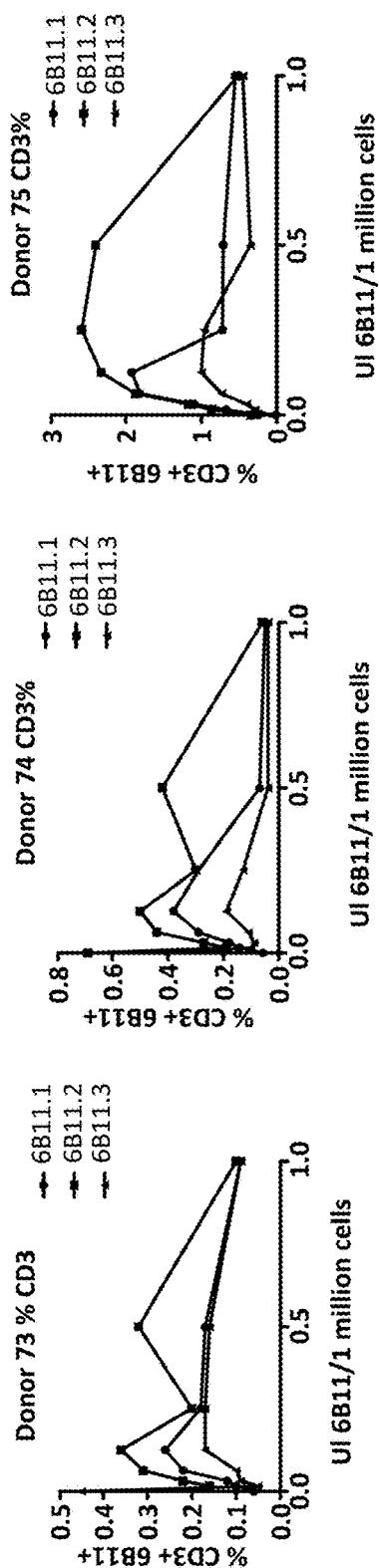
FIG. 24A-B depicts biotinylation titration of 6B11 antibodies.
Figure 24B:
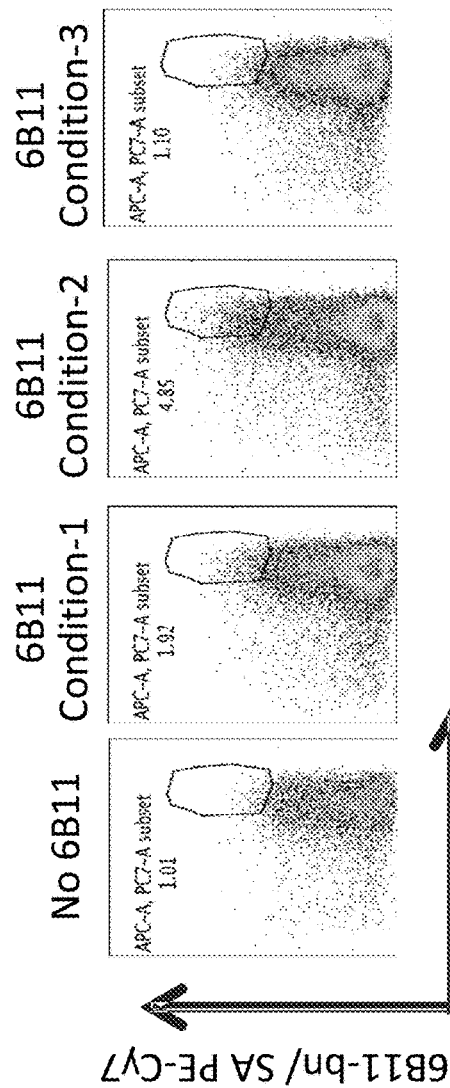

A 6B11 hybridoma was modified at pH 7.5 in PBS for 2 hours with EZ-LINK Sulfo-NHS-Biotin (ThermoFisher) at three different concentrations 1 hour and then desalted. The biotinylated antibodies and conditions are as follows: 6B11.1=100 µM (condition 1); 6B11.2=250 µM (condition 2); and 6B11.3=1 mM (condition 3).

iNKT cells were analyzed with 6B11.1 (condition 1), 6B11.2 (condition 2), or 6B11.3 (condition 3) antibodies to assess binding to cell samples from three different donors (Donor 73, Donor 74, and Donor 75) at increasing concentrations of 6B11 antibody (0 µg/µL, 0.015 µg/µL, 0.032 µg/µL, 0.062 µg/µL, 0.0125, 0.25 µg/µL, 0.5 µg/µL, and 1 µg/µL). FIG. 24A shows that the 6B11.2 biotinylated antibody had superior performance.

iNKT cells were analyzed with 6B11.1 (condition 1), 6B11.2 (condition 2), or 6B11.3 (condition 3) antibodies, in conjunction with CD127 and streptavidin PE-Cy7. FIG. 24B shows that condition 2 provided the clearest separation of iNKT cells (4.85%). The scatter plots depicted were pre-gated on CD3+ single cell lymphocytes.

The various embodiments described above can be combined to provide further embodiments. All of the U.S. patents, U.S. patent application publications, U.S. patent applications, foreign patents, foreign patent applications and non-patent publications referred to in this specification, including but not limited to U.S. Provisional Patent Application No. 62/421,979, filed on Nov. 14, 2016, are incorporated herein by reference, in their entirety except where incorporation of a reference or a portion thereof contradicts with the present disclosure. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A pharmaceutical composition comprising one or more unit doses of a cellular graft, wherein each unit dose of the cellular graft comprises populations of therapeutic cells for each kilogram (kg) of body weight of a subject receiving the cellular graft, and wherein the populations of therapeutic cells of each unit dose comprise:
more than $3 \times 10^5$ hematopoietic stem/progenitor cells (HSPC) per kilogram of body weight of the subject receiving the cellular graft,
more than $3 \times 10^5$ memory T cells (Tmem) per kilogram of body weight of the subject receiving the cellular graft,
more than $5 \times 10^5$ regulatory T cells (Treg) per kilogram of body weight of the subject receiving the cellular graft, and less than 3×10$^5$ naïve conventional αβ-T cells per kilogram of body weight of the subject receiving the cellular graft.

2. The pharmaceutical composition of claim 1, wherein the unit dose further comprises 0.5×10$^3$ to 2000×10$^3$ invariant natural killer T (iNKT) cells per kilogram of body weight of the subject receiving the cellular graft.

3. The pharmaceutical composition of claim 1, wherein the HSPC are CD34$^+$, the Tmem are CD3$^+$CD45RA$^-$CD45RO$^+$, the Treg are CD4$^+$CD25$^+$CD127$^{-/lo}$, CD45RA$^+$, or a combination thereof, and the naïve conventional αβ-T cells are CD3$^+$CD45RA$^+$CD25$^-$TCR Vα24Jα18$^-$.

4. The pharmaceutical composition of claim 2, wherein the iNKT are CD3$^+$Vα24Jα18$^+$.

5. The pharmaceutical composition of claim 1, wherein the populations of therapeutic cells of each unit dose comprise:
   1.0×10$^6$ to 50×10$^6$ HSPC per kilogram of body weight of the subject receiving the cellular graft,
   0.3×10$^6$ to 1000×10$^6$ Tmem per kilogram of body weight of the subject receiving the cellular graft,
   0.5×10$^6$ to 1000×10$^6$ Treg per kilogram of body weight of the subject receiving the cellular graft, and
   less than 3×10$^5$ naïve conventional αβ-T cells per kilogram of body weight of the subject receiving the cellular graft.

6. The pharmaceutical composition of claim 1, wherein the unit dose further comprises iNKT cells, wherein the populations of therapeutic cells of each unit dose comprise:
   1.0×10$^6$ to 50×10$^6$ HSPC per kilogram of body weight of the subject receiving the cellular graft,
   0.3×10$^6$ to 1000×10$^6$ Tmem per kilogram of body weight of the subject receiving the cellular graft,
   0.5×10$^6$ to 1000×10$^6$ Treg per kilogram of body weight of the subject receiving the cellular graft,
   0.5×10$^3$ to 2000×10$^3$ iNKT per kilogram of body weight of the subject receiving the cellular graft, and
   less than 3×10$^5$ naïve conventional αβ-T cells per kilogram of body weight of the subject receiving the cellular graft.

7. The pharmaceutical composition of claim 1, wherein the populations of therapeutic cells of each unit dose comprises 0.2×10$^6$ to 500×10$^6$ naive Treg cells per kilogram of body weight of the subject receiving the cellular graft.

8. The pharmaceutical composition of claim 2, wherein the populations of therapeutic cells of each unit dose comprises 0.2×10$^6$ to 500×10$^6$ naive Treg cells per kilogram of body weight of the subject receiving the cellular graft.

9. The pharmaceutical composition of claim 1, wherein the populations of therapeutic cells of each unit dose comprises 1.0×10$^6$ to 50×10$^6$ HSPC per kilogram of body weight of the subject receiving the cellular graft.

10. The pharmaceutical composition of claim 1, wherein the populations of therapeutic cells of each unit dose comprises 1.0×10$^6$ to 250×10$^6$ Tmem per kilogram of body weight of the subject receiving the cellular graft.

11. The pharmaceutical composition of claim 1, wherein the populations of therapeutic cells of each unit dose comprises less than 1×10$^5$ naïve conventional αβ-T cells per kilogram of body weight of the subject receiving the cellular graft.

12. The pharmaceutical composition of claim 1, wherein the populations of therapeutic cells of each unit dose comprises 1×10$^6$ to 2.5×10$^6$ Treg cells per kilogram of body weight of the subject receiving the cellular graft.

13. The pharmaceutical composition of claim 1, wherein the unit dose further comprises 1×10$^4$ to 200×10$^4$ iNKT per kilogram of body weight of the subject receiving the cellular graft.

14. The pharmaceutical composition of claim 1, wherein the pharmaceutical composition is suitable for administration to the subject receiving the cellular graft.

15. The pharmaceutical composition of claim 14, further comprising an excipient.

16. The pharmaceutical composition of claim 15, wherein the excipient is Normosol-R.

17. The pharmaceutical composition of claim 15, wherein the excipient is human serum.

18. The pharmaceutical composition of claim 14, wherein the HSPC are haploidentical to the subject receiving the cellular graft.

19. The pharmaceutical composition of claim 14, wherein the Treg, Tmem, or a combination thereof are HLA matched with the subject receiving the cellular graft.

20. The pharmaceutical composition of claim 14, wherein at least a portion of the populations of therapeutic cells are autologous to the subject receiving the cellular graft.

21. A pharmaceutical composition comprising a population of therapeutic cells that is enriched for hematopoietic stem/progenitor cells (HSPC), memory T cells (Tmem), and regulatory T cells (Treg), and wherein the population of cells is depleted of naïve conventional αβ-T cells, wherein the population of therapeutic cells comprises a ratio of naive conventional αβ-T cells to HSPC that is less than 1:400, a ratio of naïve conventional αβ-T cells to Tmem less than 1:800, and a ratio of naïve conventional αβ-T cells to Treg less than 1:5.

22. The pharmaceutical composition of claim 21, wherein the population of therapeutic cells further comprises invariant Natural Killer T cells (iNKT) and the population of therapeutic cells comprises a ratio of naïve conventional αβ-T cells to iNKT less than 100:1.

23. The pharmaceutical composition of claim 21, wherein the ratio of naïve conventional αβ-T cells to Tmem is less than 1:3.

24. The pharmaceutical composition of claim 21, wherein the population of therapeutic cells comprises a ratio of naïve conventional αβ-T cells to naïve Treg less than 1:2.

* * * * *

UNITED STATES PATENT AND TRADEMARK OFFICE
CERTIFICATE OF CORRECTION

PATENT NO. : 10,300,090 B2
APPLICATION NO. : 15/922709
DATED : May 28, 2019
INVENTOR(S) : Ivan K. Dimov, Nathaniel Fernhoff and Kevin Sheehan It is certified that error appears in the above-identified patent and that said Letters Patent is hereby corrected as shown below:

In the Claims

Column 49, Line 1, Claim 1:
Replace "less than $3\times10^5$ nave conventional αβ-T cells" with --less than $3 \times 10^5$ naïve conventional αβ-T cells--

Column 49, Line 6, Claim 2:
Replace "invariant natural killer T (iNKT) cells per" with --invariant natural killer T cells (iNKT) per--

Column 49, Line 11, Claim 3:
Replace "the nave conventional" with --the naïve conventional--

Column 49, Line 29, Claim 6:
Replace "comprises iNKT cells, wherein" with --comprises iNKT, wherein--

Column 49, Line 44, Claim 7:
Replace "$500\times10^6$ naive Treg cells per" with --$500 \times 10^6$ naïve Treg per--

Column 49, Line 48, Claim 8:
Replace "$500\times10^6$ naive Treg cells per" with --$500 \times 10^6$ naïve Treg per--

Column 50, Line 10, Claim 12:
Replace "$2.5\times10^6$ Treg cells per" with --$2.5 \times 10^6$ Treg per--

Column 50, Line 38, Claim 21:
Replace "comprises a ratio of naive" with --comprises a ratio of naïve--

Column 50, Line 40, Claim 21:
Replace "Tmem less than 1:800" with --Tmem that is less than 1:800--

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*

Column 50, Line 41, Claim 21:
Replace "Treg less than 1:5" with --Treg that is less than 1:5--

Column 50, Line 47, Claim 22:
Replace "iNKT less than 100:1" with --iNKT that is less than 100:1--

Column 50, Line 53, Claim 24:
Replace "Treg less than 1:2." with --Treg that is less than 1:2.--